(12) United States Patent
Hasegawa et al.

(10) Patent No.: US 8,420,290 B2
(45) Date of Patent: Apr. 16, 2013

(54) ACETAL COMPOUNDS AND THEIR PREPARATION, POLYMERS, RESIST COMPOSITIONS AND PATTERNING PROCESS

(75) Inventors: Koji Hasegawa, Joetsu (JP); Masaki Ohashi, Joetsu (JP); Takeshi Kinsho, Joetsu (JP); Tsunehiro Nishi, Joetsu (JP); Masayoshi Sagehashi, Joetsu (JP)

(73) Assignee: Shin-Etsu Chemical Co., Ltd, Tokyo (JP)

( * ) Notice: Subject to any disclaimer, the term of this patent is extended or adjusted under 35 U.S.C. 154(b) by 443 days.

(21) Appl. No.: 12/625,711

(22) Filed: Nov. 25, 2009

(65) Prior Publication Data

US 2010/0136485 A1 Jun. 3, 2010

(30) Foreign Application Priority Data

Nov. 28, 2008 (JP) ................. 2008-304123

(51) Int. Cl.
| | |
|---|---|
| G03F 7/039 | (2006.01) |
| G03F 7/20 | (2006.01) |
| G03F 7/30 | (2006.01) |
| G03F 7/38 | (2006.01) |
| G03F 7/11 | (2006.01) |

(52) U.S. Cl.
USPC ........ 430/270.1; 430/325; 430/326; 430/330; 430/907; 430/910; 430/942; 560/220; 568/591; 568/665; 568/579; 526/282; 526/328; 526/332

(58) Field of Classification Search .......... None
See application file for complete search history.

(56) References Cited

U.S. PATENT DOCUMENTS

| | | | |
|---|---|---|---|
| 4,491,628 A | 1/1985 | Ito et al. | |
| 4,603,101 A | 7/1986 | Crivello | |
| 5,118,585 A | 6/1992 | Schwalm et al. | |
| 5,650,483 A | 7/1997 | Malik et al. | |
| 6,312,867 B1 | 11/2001 | Kinsho et al. | |
| 6,329,125 B2 | 12/2001 | Takechi et al. | |
| 6,673,518 B2 | 1/2004 | Nishi et al. | |
| 6,830,866 B2 | 12/2004 | Kobayashi et al. | |
| 7,015,363 B2 | 3/2006 | Shimizu et al. | |
| 2005/0004391 A1* | 1/2005 | Hatakeyama et al. | 560/220 |
| 2005/0147920 A1* | 7/2005 | Lin et al. | 430/311 |
| 2007/0148592 A1* | 6/2007 | Wada et al. | 430/270.1 |

FOREIGN PATENT DOCUMENTS

| | | | |
|---|---|---|---|
| JP | 62-115440 A | 5/1987 | |
| JP | 2-19847 A | 1/1990 | |
| JP | 2-80515 A | 3/1990 | |
| JP | 2-27660 B2 | 6/1990 | |
| JP | 4-215661 A | 8/1992 | |
| JP | 5-88367 A | 4/1993 | |
| JP | 9-73173 A | 3/1997 | |
| JP | 2000-336121 A | 12/2000 | |
| JP | 2003-64134 A | 3/2003 | |
| JP | 2003-66612 A | 3/2003 | |
| WO | WO 03/006407 A1 | 1/2003 | |

OTHER PUBLICATIONS

Allen et al., "Single Layer Resists With Enhanced Etch Resistance for 193 nm Lithography", Journal of Photopolymer Science and Technology, 1994, vol. 7, No. 3, pp. 507-516.
Arimitsu et al., "Effect of Phenolic Hydroxyl Residues on the Improvement of Acid-Proliferation-Type Photoimaging Materials", Journal of Photopolymer Science and Technology, 1996, vol. 9, No. 1, pp. 29-30.
Arimitsu et al., "Sensitivity Enhancement of Chemical-Amplification-Type Photoimaging Materials by Acetoacetic Acid Derivatives", Journal of Photopolymer Science and Technology, 1995, vol. 8, No. 1, pp. 43-44.
Kudo et al., "Enhancement of the Sensitivity of Chemical-Amplification-Type Photoimaging Materials by β-Tosyloxyketone Acetals", Journal of Photopolymer Science and Technology, 1995, vol. 8, No. 1, pp. 45-46.

* cited by examiner

Primary Examiner — Sin J. Lee
(74) Attorney, Agent, or Firm — Birch, Stewart, Kolasch & Birch, LLP

(57) ABSTRACT

An acetal compound of formula (1) is provided wherein $R^1$ is H, methyl or trifluoromethyl, $R^2$ is a monovalent $C_1$-$C_{10}$ hydrocarbon group, $R^3$ and $R^4$ are H or a monovalent $C_1$-$C_{10}$ hydrocarbon group, $R^2$ and $R^3$ may together form an aliphatic hydrocarbon ring, and $X^1$ is a single bond or a divalent $C_1$-$C_4$ hydrocarbon group. A polymer comprising recurring units derived from the acetal compound is used as a base resin to formulate a resist composition which exhibits a high resolution when processed by micropatterning technology, especially ArF lithography.

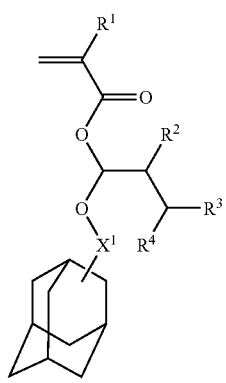

(1)

17 Claims, No Drawings

ACETAL COMPOUNDS AND THEIR PREPARATION, POLYMERS, RESIST COMPOSITIONS AND PATTERNING PROCESS

CROSS-REFERENCE TO RELATED APPLICATION

This non-provisional application claims priority under 35 U.S.C. §119(a) on Patent Application No. 2008-304123 filed in Japan on Nov. 28, 2008, the entire contents of which are hereby incorporated by reference.

TECHNICAL FIELD

This invention relates to (1) novel acetal compounds useful as raw materials for the synthesis of functional materials, pharmaceutical and agricultural chemicals, and a method for preparing the same. The acetal compounds are useful as monomers to form polymers which have high transparency to radiation of wavelength up to 500 nm, especially up to 300 nm, for example, KrF laser, ArF laser or $F_2$ laser radiation, and improved development properties, when used as a base resin in radiation-sensitive resist compositions. The invention also relates to (2) polymers comprising recurring units derived from the acetal compounds, (3) photoresist compositions comprising the polymers, and (4) a patterning process using the photoresist compositions.

BACKGROUND OF THE INVENTION

In the recent drive for higher integration and operating speeds in LSI devices, it is desired to miniaturize the pattern rule. Great efforts have been devoted for the development of the micropatterning technology using deep-ultraviolet (deep-UV) or vacuum-ultraviolet (VUV) lithography. The photolithography using KrF excimer laser (wavelength 248 nm) as the light source has already established the main role in the commercial manufacture of semiconductor devices. The lithography using ArF excimer laser (wavelength 193 nm) is at the start of its application to commercial fabrication by the advanced micropatterning technology. For the ArF excimer laser lithography, however, partly because the succeeding technology has not been established, it is strongly desired to improve the performance of resist material in order to gain a further stretch of resolution. Efforts are also made to develop the immersion lithography process that intends to gain a stretch of resolution by interposing a high refractive index liquid between a resist coating film and a projection lens. There is a need for a resist material meeting such requirements.

For resist materials adapted to the ArF excimer laser lithography, polyacrylic or polymethacrylic acid derivatives and polymers comprising cycloaliphatic compounds in the backbone are under investigation. In either case, the basic concept is that some or all of alkali soluble sites of an alkali soluble resin are protected with acid labile groups. The overall performance of resist material is adjusted by a choice of an adequate protecting group from among numerous acid labile protecting groups.

Exemplary acid labile protecting groups include tert-butoxycarbonyl (JP-B H02-27660), tert-butyl (JP-A S62-115440 and J. Photopolym. Sci. Technol. 7 [3], 507 (1994)), 2-tetrahydropyranyl (JP-A H02-80515 and JP-A H05-88367), 1-ethoxyethyl (JP-A H02-19847 and JP-A H04-215661), and adamantane structure-containing alkyl (JP-A H09-73173 and JP-A H15-64134). While it is desired to achieve a finer pattern rule, none of these acid labile protecting groups are deemed to exert satisfactory performance.

More particularly, since tert-butoxycarbonyl and tert-butyl are least reactive with acids, a substantial quantity of energy radiation must be irradiated to generate a sufficient amount of acid in order to establish a difference in dissolution rate before and after exposure. If a photoacid generator of the strong acid type is used, the exposure dose can be reduced to a relatively low level because reaction can proceed with a small amount of acid generated. In this event, however, the deactivation of the generated acid by air-borne basic substances has a relatively large influence, giving rise to such problems as T-top pattern profile. On the other hand, 2-tetrahydropyranyl and 1-ethoxyethyl are reactive with acids and advantageous from the standpoint of resolution. Where these groups are used as protective groups for carboxylic acid, thermal stability is poor and a concern about shelf stability is left.

The resist materials described above commonly suffer from noticeable line density dependency (or optical proximity effect) in that when a pattern including a high density (or grouped) region and a low density (or isolated) region is to be transferred, exposure at an identical dose fails to produce the desired pattern which is satisfactory in both the regions. Generally speaking, in the ArF excimer laser lithography, the acid generated upon exposure triggers deprotection reaction on the base resin which proceeds during heat treatment following exposure (post-exposure bake or PEB). Migration of the acid occurs during PEB. Since chemically amplified resist materials depend on the function of the acid to act as a catalyst to promote deprotection reaction, moderate acid migration is necessary. However, acid migration degrades an optical image, indicating that excess acid migration detracts from resolution. To comply with the outstanding demands for a further size reduction in the ArF excimer laser lithography and a higher resolution due to a good command of the immersion lithography, there is a need for a resist material featuring controlled acid migration and higher resolution capability.

CITATION LIST

Patent Document 1: JP-B H02-27660
Patent Document 2: JP-A S62-115440
Patent Document 3: JP-A H02-80515
Patent Document 4: JP-A H05-88367
Patent Document 5: JP-A H02-19847
Patent Document 6: JP-A H04-215661
Patent Document 7: JP-A H09-73173
Patent Document 8: JP-A 2003-64134
Non-Patent Document 1: J. Photopolym. Sci. Technol. 7 [3], 507 (1994)

DISCLOSURE OF THE INVENTION

An object of the present invention is to provide acetal compounds useful as monomers for the synthesis of polymers, polymers comprising recurring units derived from the acetal compounds, and resist compositions comprising the polymers, which compositions exhibit a high resolution, minimized pattern density dependency, and improved mask fidelity when processed by photolithography, especially immersion photolithography, using high-energy radiation such as ArF excimer laser radiation as a light source. Another object is to provide a patterning process using the resist compositions.

The inventors have found that using two compounds of the general formulae (2) and (3) as starting reactants, an acetal compound of the general formula (1) can be readily synthesized, which is useful as a raw material to resist materials; and that a resist composition comprising a polymer derived from the acetal compound as a base resin has very high resolution property and is advantageously used in precise micropatterning.

Accordingly, the present invention provides an acetal compound, polymer, resist composition, and patterning process, as defined below.

In a first aspect, the invention provides an acetal compound having the general formula (1).

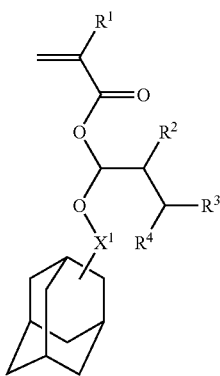

(1)

Herein $R^1$ is hydrogen, methyl or trifluoromethyl, $R^2$ is a straight, branched or cyclic monovalent $C_1$-$C_{10}$ hydrocarbon group, $R^3$ and $R^4$ are each independently hydrogen or a straight, branched or cyclic monovalent $C_1$-$C_{10}$ hydrocarbon group, $R^2$ and $R^3$ may bond together to form an aliphatic hydrocarbon ring with the carbon atoms to which they are attached, and $X^1$ is a single bond or a straight or branched divalent $C_1$-$C_4$ hydrocarbon group.

In a second aspect, the invention provides a method for preparing a vinyl ether compound having the general formula (5), comprising the steps of etherifying an adamantane compound having the general formula (2) and an alkenyl compound having the general formula (3) to form an allyl ether compound having the general formula (4) and isomerizing the double bond in the allyl ether compound.

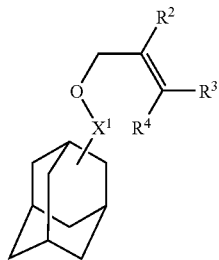

(2)

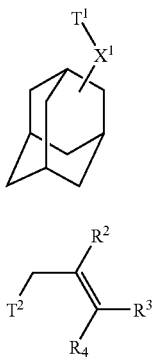

(3)

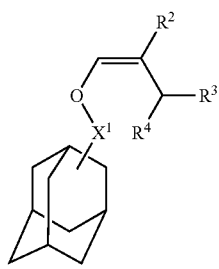

(4)

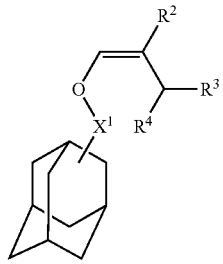

(5)

Herein $R^2$, $R^3$, $R^4$ and $X^1$ are as defined above, $T^1$ and $T^2$ are each independently a hydroxyl group, halogen atom, alkanesulfonyloxy or arenesulfonyloxy group.

The invention also provides a method for preparing an acetal compound having the general formula (1), comprising the steps of effecting addition reaction of a hydrogen halide to a vinyl ether compound having the general formula (5) to form a halogenated alkyl ether compound having the general formula (6), and esterifying the halogenated alkyl ether compound with a corresponding carboxylic acid salt having the general formula (7).

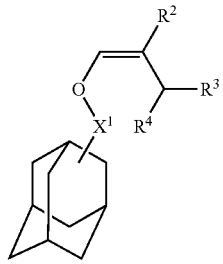

(5)

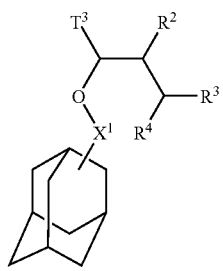

(6)

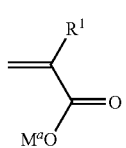

(7)

-continued

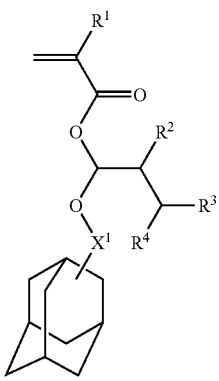
(1)

Herein $R^1$, $R^2$, $R^3$, $R^4$ and $X^1$ are as defined above, $T^3$ is a halogen atom, and $M^a$ is Li, Na, K, $Mg_{1/2}$, $Ca_{1/2}$ or substituted or unsubstituted ammonium.

In a fourth aspect, the invention provides a polymer comprising recurring units of the general formula (8).

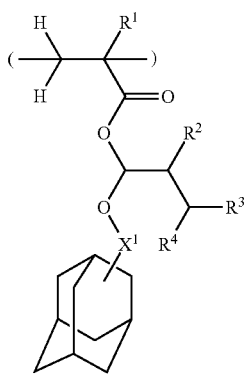
(8)

Herein $R^1$, $R^2$, $R^3$, $R^4$ and $X^1$ are as defined above.

In a preferred embodiment, the polymer may further comprise recurring units of at least one type selected from the general formulae (9) to (12).

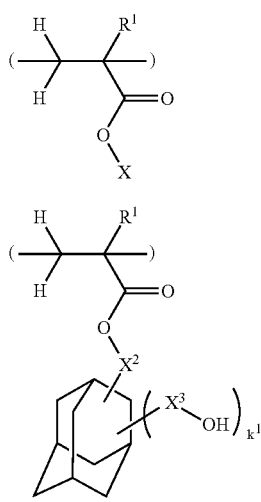
(9)
(10)

-continued

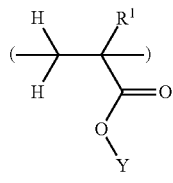
(11)

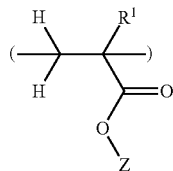
(12)

Herein $R^2$ is as defined above, X is an acid labile group different from formula (8), Y is a substituent group having lactone structure, Z is hydrogen, $C_1$-$C_{15}$ fluoroalkyl or $C_1$-$C_{15}$ fluoroalcohol-containing substituent group, $X^2$ and $X^3$ are each independently a single bond or a straight or branched divalent $C_1$-$C_4$ hydrocarbon group, and $k^1$ is an integer of 1 to 3.

In a fifth aspect, there is provided a resist composition comprising the polymer as a base resin.

The invention further provides a process for forming a pattern, comprising the steps of applying the resist composition onto a substrate to form a resist coating; heat treating the resist coating and exposing to high-energy radiation or electron beam through a photomask; and heat treating the exposed coating and developing with a developer. In a preferred embodiment, the exposing step is performed by immersion lithography including holding a high refractive index liquid having a refractive index of at least 1.0 between the resist coating and a projection lens. In another preferred embodiment, a protective film is formed on the resist coating, and the exposing step is performed by immersion lithography including holding a high refractive index liquid having a refractive index of at least 1.0 between the protective film and a projection lens.

ADVANTAGEOUS EFFECT OF INVENTION

The resist compositions, typically chemically amplified positive resist compositions exhibit a very high resolution when processed by the micropatterning technology, especially the ArF lithography, and are useful in precise micropatterning.

DESCRIPTION OF EMBODIMENTS

In the disclosure, the singular forms "a," "an" and "the" include plural referents unless the context clearly dictates otherwise. The notation (Cn-Cm) means a group containing from n to m carbon atoms per group.

It is understood that for some structures represented by chemical formulae, there can exist enantiomers and diastereomers because of the presence of asymmetric carbon atoms. In such a case, a single formula collectively represents all such isomers. The isomers may be used alone or in admixture.

Acetal Compound

In the first embodiment, the invention provides an acetal compound having the general formula (1).

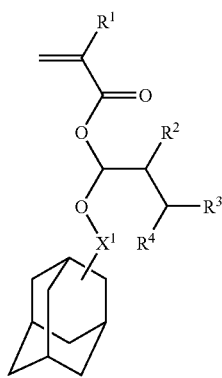

(1)

Herein $R^1$ is hydrogen, methyl or trifluoromethyl. $R^2$ is a straight, branched or cyclic monovalent $C_1$-$C_{10}$ hydrocarbon group. $R^3$ and $R^4$ are each independently hydrogen or a straight, branched or cyclic monovalent $C_1$-$C_{10}$ hydrocarbon group. $R^2$ and $R^3$ may bond together to form an aliphatic hydrocarbon ring with the carbon atoms to which they are attached. $X^1$ is a single bond or a straight or branched divalent $C_1$-$C_4$ hydrocarbon group.

Suitable straight, branched or cyclic monovalent $C_1$-$C_{10}$ hydrocarbon groups represented by $R^2$ to $R^4$ include methyl, ethyl, n-propyl, isopropyl, n-butyl, sec-butyl, isobutyl, tert-butyl, cyclopentyl, cyclohexyl, 2-ethylhexyl, and n-octyl.

Where $R^2$ and $R^3$ bond together to form an aliphatic hydrocarbon ring with the carbon atoms to which they are attached, suitable aliphatic hydrocarbon rings are those of 3 to 20 carbon atoms, preferably 4 to 15 carbon atoms, including cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

Suitable straight or branched divalent $C_1$-$C_4$ hydrocarbon groups represented by $X^1$ include methylene, ethylene, propane-1,1-diyl, propane-1,2-diyl, propane-1,3-diyl, butane-1,1-diyl, butane-1,2-diyl, butane-1,3-diyl, and butane-1,4-diyl.

Illustrative non-limiting examples of the compound having formula (1) are given below.

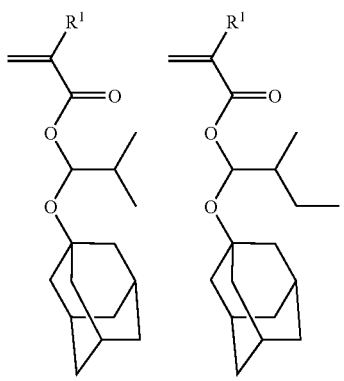

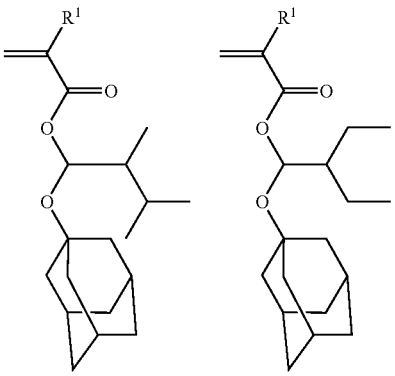

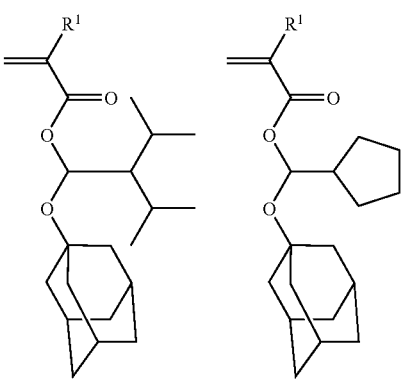

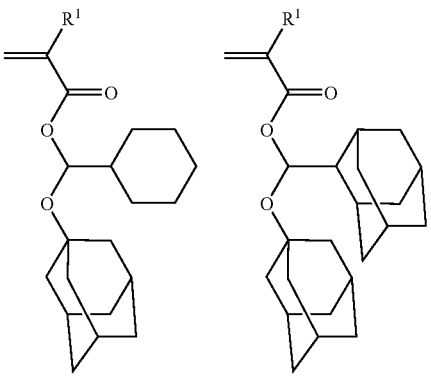

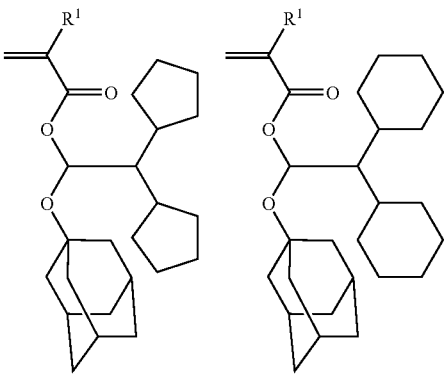

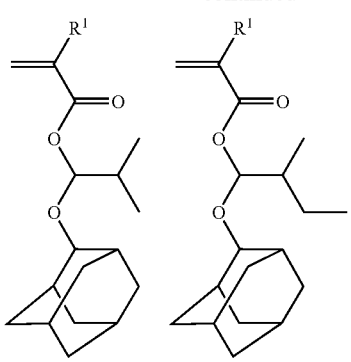
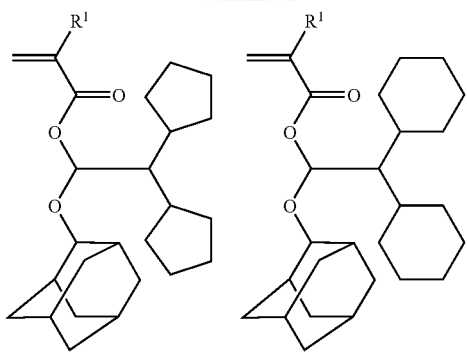
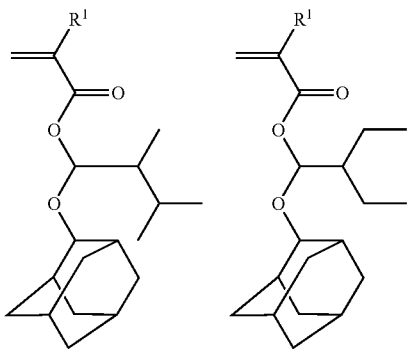
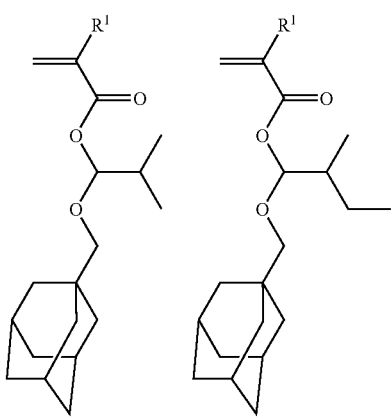
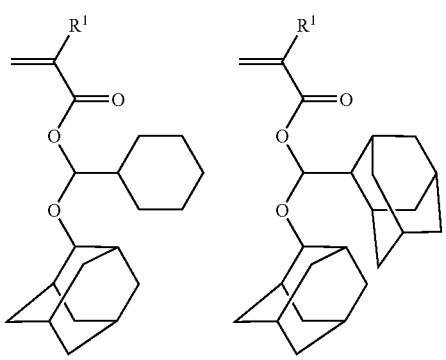

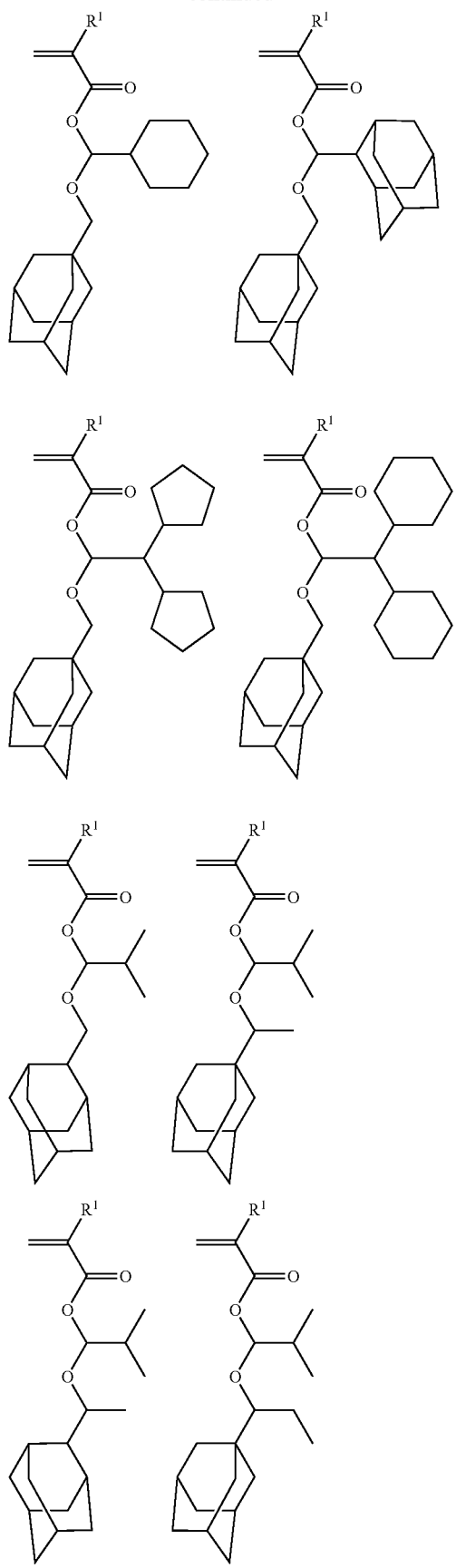
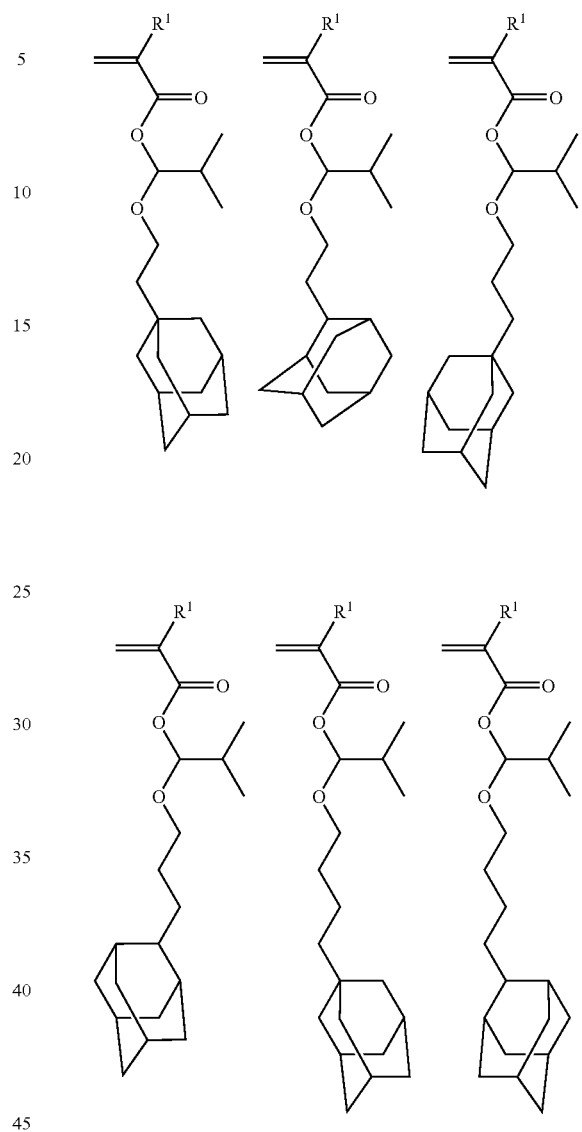

Herein R¹ is as defined above.

The second embodiment of the invention is a method for preparing a vinyl ether compound having the general formula (5), comprising the steps of etherifying an adamantane compound having the general formula (2) and an alkenyl compound having the general formula (3) to form an allyl ether compound having the general formula (4) and isomerizing the double bond in the allyl ether compound.

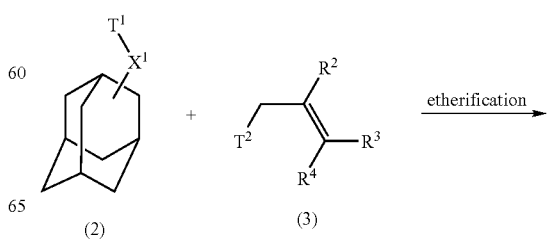

-continued

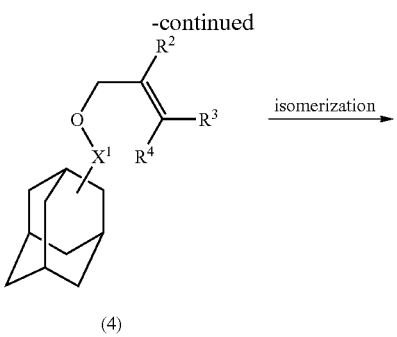

(4)

isomerization

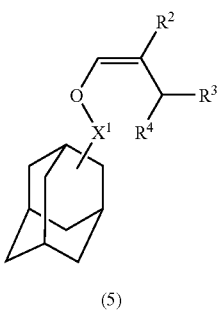

(5)

Herein $R^2$ to $R^4$ and $X^1$ are as defined above, $T^1$ and $T^2$ are each independently a hydroxyl group, halogen atom, alkanesulfonyloxy or arenesulfonyloxy group. Of the groups represented by $T^2$ and $T^2$, suitable halogen atoms include chlorine, bromine and iodine; and suitable alkanesulfonyloxy and arenesulfonyloxy groups include methanesulfonyloxy, trifluoromethanesulfonyloxy, benzenesulfonyloxy, and p-toluenesulfonyloxy. It is most preferred that $T^1$ be hydroxyl and $T^2$ be halogen, especially chlorine because the starting reactants are readily available.

The first step, i.e., synthesis of an allyl ether compound having formula (4) is described. The first step is an etherifying reaction of an adamantane compound (2) and an alkenyl compound (3) to form an allyl ether compound (4).

One exemplary etherifying method is by treating an adamantane compound (2) and an alkenyl compound (3) with a base to effect etherification. Examples of the base used herein include alkoxides such as sodium methoxide, sodium ethoxide, lithium methoxide, lithium ethoxide, lithium tert-butoxide, and potassium tert-butoxide; organic amines such as pyridine, triethylamine, N,N-dimethylaniline, and 4-dimethylaminopyridine; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate, and potassium carbonate; metal hydrides such as borane, alkylboranes, sodium hydride, lithium hydride, potassium hydride, and calcium hydride; alkyl metal compounds such as trityllithium, tritylsodium, tritylpotassium, methyllithium, phenyllithium, sec-butyllithium, tert-butyllithium, methylmagnesium chloride, ethylmagnesium chloride, and ethylmagnesium bromide; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrmethylsilyiamide, sodium bistrimethylsilylamide, potassium bistrimethylsilylamide, lithium isopropylcyclohexylamide, and magnesium bromide diisopropylamide. The base is preferably used in an amount of 0.9 to 10 moles, more preferably 1.0 to 3.0 moles per mole of adamantane compound (2).

Examples of the solvent include water or ethers such as tetrahydrofuran, diethyl ether, di-n-butyl ether, and 1,4-dioxane, hydrocarbons such as n-hexane, n-heptane, benzene, toluene, xylene and cumene, alcohols such as methanol, ethanol, isopropyl alcohol, and tert-butyl alcohol, aprotic polar solvents such as dimethyl sulfoxide (DMSO) and N,N-dimethylformamide (DMF), and chlorinated organic solvents such as methylene chloride, chloroform and carbon tetrachloride. Depending on reaction conditions, an appropriate one or more may be chosen from these solvents. In some cases, the abovementioned base itself may serve as a solvent.

The reaction temperature and time may widely vary with reagents and other reaction conditions. When the reaction uses compounds wherein $T^1$=hydroxyl and $T^2$=chlorine and sodium hydride as the base, for example, the reaction temperature is preferably in the range of room temperature to 80° C., and more preferably 30° C. to 70° C. for rapid progress of reaction to completion. The reaction time is determined as appropriate by monitoring the reaction process by gas chromatography (GC) or silica gel thin-layer chromatography (TLC) because it is desirable from the yield aspect to drive the reaction to completion. Usually the reaction time is about 1 to about 60 hours. The desired allyl ether compound (4) may be obtained from the reaction mixture by ordinary aqueous work-up. If necessary, the compound may be purified by standard techniques like distillation and chromatography.

Another exemplary etherifying method is etherification utilizing dehydration reaction between an adamantane compound (2) and an alkenyl compound (3) wherein both $T^1$ and $T^2$ are hydroxyl. Better results are obtained from this dehydration reaction when an acid, salt thereof or phosphorus reagent is used. Suitable acids used herein include mineral acids such as hydrochloric acid, hydrobromic acid, sulfuric acid, nitric acid, perchloric acid, and phosphoric acid, and salts thereof; organic acids such as formic acid, acetic acid, oxalic acid, benzoic acid, p-toluenesulfonic acid, and benzenesulfonic acid, and salts thereof; and cation-exchange resins. The acid is preferably used in a catalytic amount of 0.01 to 10 moles, and more preferably 0.01 to 0.5 mole per mole of adamantane compound (2). It is desirable to remove the water formed with the progress of reaction. Typically, water may be positively azeotroped off using a hydrocarbon such as n-hexane, n-heptane, benzene, toluene, xylene or cumene, thereby accelerating the reaction. The reaction may also be effected in vacuum.

Suitable phosphorus reagents include hexamethylphosphoric triamide (HMPA), dialkyl azodicarboxylate-triphenylphosphine, triethylphosphine, and potassium carbonate-triphenylphosphine. The phosphorus reagent is preferably used in an amount of 0.9 to 10 moles, and more preferably 1.0 to 1.2 moles per mole of adamantane compound (2).

The reaction temperature and time may widely vary with other reaction conditions. When triphenylphosphine and carbon tetrachloride are used, for example, the reaction temperature is preferably in the range of room temperature to reflux temperature, and more preferably 50° C. to reflux temperature for rapid progress of reaction to completion. The reaction time is determined as appropriate by monitoring the reaction process by GC or TLC because it is desirable from the yield aspect to drive the reaction to completion. Usually the reaction time is about 1 to about 30 hours.

The second step is to derive a vinyl ether compound (5) by isomerizing the double bond in the allyl ether compound (4). Isomerization may be done by any well-known techniques, for example, using a base as described in the first step or a transition metal catalyst such as rhodium, ruthenium or iridium, in a solventless system or in an aprotic polar solvent such as dimethyl sulfoxide (DMSO) or N,N-dimethylformamide (DMF). It is advantageous from the aspects of pot yield and cost to select DMSO as the solvent and potassium tert-butoxide as the base.

The third embodiment of the invention is a method for preparing an acetal compound having formula (1), comprising the steps of effecting addition reaction of a hydrogen halide to a vinyl ether compound having formula (5) to form a halogenated alkyl ether compound having formula (6), and esterifying the halogenated alkyl ether compound with a corresponding carboxylic acid salt having formula (7).

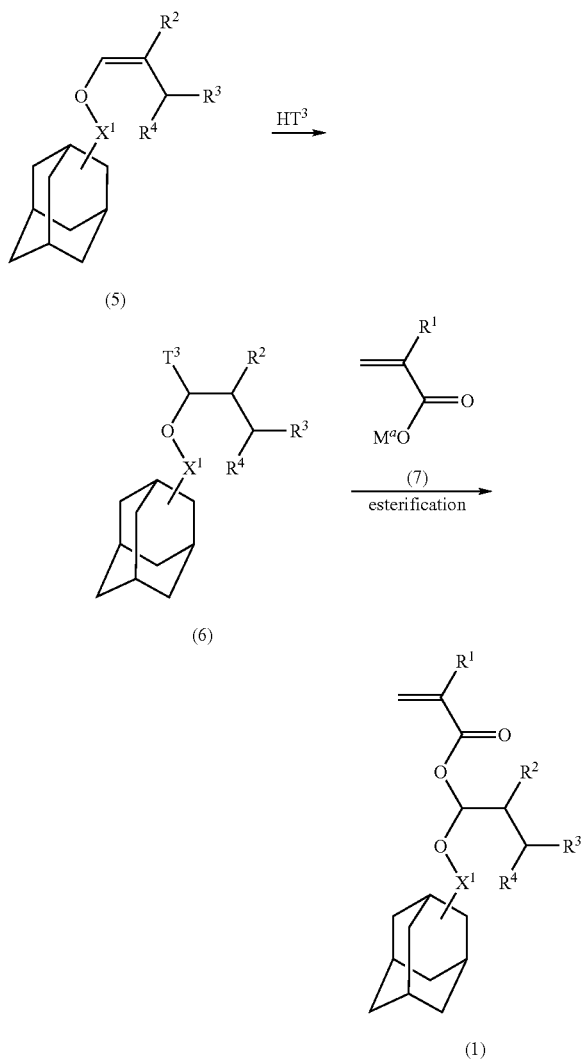

Herein $R^1$ to $R^4$, $X^1$, $T^3$ and $M^a$ are as defined above.

Described below is the first step or synthesis of a halogenated alkyl ether compound (6). The first step is by effecting addition reaction of a hydrogen halide to a vinyl ether compound (5) to form a halogenated alkyl ether compound (6). Suitable halogens represented by $T^3$ include chlorine, bromine and iodine. Inter alia, chlorine is most preferred for ease of handling. The addition reaction may be effected in a solventless system or in a solvent. Suitable solvents include ethers such as tetrahydrofuran, diethyl ether, di-n-butyl ether, and 1,4-dioxane, hydrocarbons such as n-hexane, n-heptane, benzene, toluene, xylene and cumene, aprotic polar solvents such as dimethyl sulfoxide (DMSO) and N,N-dimethylformamide (DMF), and chlorinated organic solvents such as methylene chloride, chloroform and carbon tetrachloride. Depending on reaction conditions, an appropriate one or more may be chosen from these solvents.

The reaction temperature and time may widely vary with other reaction conditions. Where $T^3$ is chlorine, for example, the reaction temperature is preferably in the range of −30° C. to 80° C., and more preferably −10° C. to 40° C. for rapid progress of reaction to completion. The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.1 to about 10 hours. If necessary, the compound may be purified from the reaction mixture by standard techniques like distillation, chromatography and recrystallization. Most often, the crude product has a sufficient purity as the reactant to the subsequent step and may be used in the subsequent step without purification.

Described below is the second step or synthesis of acetal compound (1). The second step is by esterifying the halogenated alkyl ether compound (6) with a corresponding carboxylic acid salt (7) to produce an acetal compound (1).

The esterifying reaction may be effected by a standard technique. The carboxylic acid salt (7) may be any of commercially available carboxylic acid salts such as carboxylic acid metal salts as purchased. Alternatively, a carboxylic acid salt may be formed within the reaction system from a corresponding carboxylic acid such as methacrylic acid or acrylic acid and a base. The amount of carboxylic acid salt (7) used is preferably 0.5 to 10 moles, and more preferably 1.0 to 3.0 moles per mole of the reactant, halogenated alkyl ether compound (6). If the amount of carboxylic acid salt (7) is less than 0.5 mole, a large fraction of the reactant may be left unreacted, leading to a substantial drop of percent yield. More than 10 moles of carboxylic acid salt (7) may be uneconomical due to increased material costs and reduced pot yields. In the embodiment where carboxylic acid salt is formed within the reaction system from a corresponding carboxylic acid and a base, examples of the base used herein include amines such as ammonia, triethylamine, pyridine, lutidine, collidine, and N,N-dimethylaniline; hydroxides such as sodium hydroxide, potassium hydroxide, and tetramethylammonium hydroxide; carbonates such as potassium carbonate and sodium hydrogen carbonate; metals such as sodium; metal hydrides such as sodium hydride; metal alkoxides such as sodium methoxide and potassium tert-butoxide; organometallics such as butyllithium and ethylmagnesium bromide; and metal amides such as lithium diisopropylamide. One or more bases may be selected from these examples. The amount of the base used is preferably 0.2 to 10 moles, and more preferably 0.5 to 2.0 moles per mole of the corresponding carboxylic acid. If the amount of the base is less than 0.2 mole, a large fraction of the carboxylic acid may become a waste, which is uneconomical. More than 10 moles of the base may lead to a substantial drop of yield due to increased side reactions.

Suitable solvents include hydrocarbons such as toluene, xylene, hexane and heptane; chlorinated solvents such as methylene chloride, chloroform and dichloroethane; ethers such as diethyl ether, tetrahydrofuran, dibutyl ether; ketones such as acetone and 2-butanone; esters such as ethyl acetate and butyl acetate; nitriles such as acetonitrile; alcohols such as methanol and ethanol; aprotic polar solvents such as N,N-dimethylformamide (DMF), N,N-dimethylacetamide, and dimethyl sulfoxide (DMSO); and water, which may be used alone or in admixture. To the reaction, a phase transition catalyst such as tetrabutylammonium hydrogensulfate may be added. The amount of phase transition catalyst added is preferably 0.0001 to 1.0 mole, and more preferably 0.001 to 0.5 mole per mole of the reactant, halogenated alkyl ether compound (6). Less than 0.0001 mole of the catalyst may fail to achieve the catalytic effect whereas more than 1.0 mole of the catalyst may be uneconimical due to increased material costs.

The reaction temperature is preferably in the range of −70° C. to the boiling point of the solvent used. An appropriate temperature may be selected in accordance with other reaction conditions, although it is most often in the range of 0° C. to 30° C. Since noticeable side reactions occur at higher temperatures, it is important for gaining higher yields that the reaction run at a temperature which is low, but enough to ensure a practically acceptable reaction rate. Also for higher yields, the reaction time is preferably determined by monitoring the reaction process by thin-layer chromatography (TLC) or gas chromatography (GC). Usually the reaction time is about 30 minutes to about 40 hours. The desired acetal compound (1) may be obtained from the reaction mixture by ordinary aqueous work-up. If necessary, the compound may be purified by standard techniques like distillation, recrystallization and chromatography.

An alternative method for the synthesis of acetal compound (1) is addition reaction between a corresponding carboxylic acid and vinyl ether compound (5) in the presence of an acid catalyst. This reaction may be effected by any well-known techniques. Typically, in a solventless system or in a solvent such as toluene or hexane, vinyl ether compound (5) and a corresponding carboxylic acid such as methacrylic acid or acrylic acid are reacted in the presence of an acid catalyst at a temperature of 0° C. to 50° C., while the water formed by reaction may be removed out of the system if necessary. Suitable acid catalysts used herein include mineral acids such as hydrochloric acid, sulfuric acid, nitric acid and perchloric acid and organic acids such as p-toluenesulfonic acid and benzenesulfonic acid.

Typical substituent groups in the form of carboxylic acid protected with acetal as in the present invention include ethoxyethyl (EOE) and tetrahydropyranyl (THP) groups. However, these groups are highly reactive to acid as previously pointed out, and thus impractical in the resist application because they may deprive the resist of shelf stability. In general, acid-assisted elimination reaction of methacrylic acid tertiary ester proceeds as E2 elimination reaction in accordance with the following scheme 1 to give olefin and methacrylic acid. In order for effective reaction to run, a hydrogen atom (=Ha) having a dihedral angle of 180° with respect to the methacryloyl group (i.e., at trans antiparallel position) is necessary.

Scheme 1

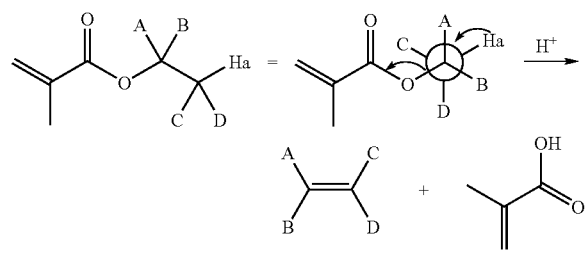

In order that the acetal compound of formula (1) take an advantageous conformation for the aforementioned elimination reaction, the sterically most disadvantageous conformation having the methacryloyl group ($R^1$ in the formula is methyl) vicinal to $R^2$ and $R^7$ as shown in formula (13) below is necessary. This conformation retards olefin formation as compared with common acetal compounds such as EOE and THP groups. As a consequence, it becomes possible to mitigate excessive acid reactivity, the drawback of acetal type leaving group. Accordingly, a polymer derived from the acetal compound of formula (1) may be used as a base resin to formulate a resist composition which has both sufficient reactivity (to provide a high sensitivity and high resolution) and practical stability.

(13)

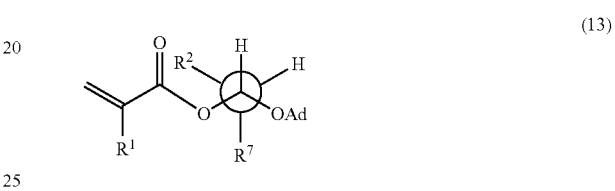

Herein $R^1$ and $R^2$ are as defined above, $R^7$ is a group of the formula:

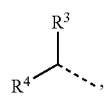

and Ad is a group of the formula:

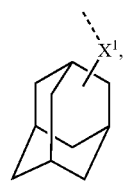

wherein $R^2$, $R^4$, and $X^1$ are as defined above, and the broken line denotes a valence bond.

The acetal compound of the invention has a robust adamantane ring in the alcohol moiety of acetal, which can reduce the free volume and control the acid migration in a resist film unlike other fused alicyclic groups such as norbornane and tricyclo[5.2.1.0$^{2,6}$]decane (TCD). As a result, a highly resolvable resist composition having improved mask fidelity can be formulated.

Reference is made to an example of acetal compound (14) having as the fused alicyclic group a TCD ring with a number of carbon atoms equal to adamantane. Since it has β-hydrogen (=Hb) in the alcohol moiety of acetal as shown by scheme 2 below, acid decomposition (deprotection) by β-elimination mechanism can take place. As used herein, the term "β-hydrogen" refers to a hydrogen atom which is bonded to a carbon atom (β-carbon) vicinal to a carbon atom (α-carbon) bonded to an oxygen atom.

Scheme 2

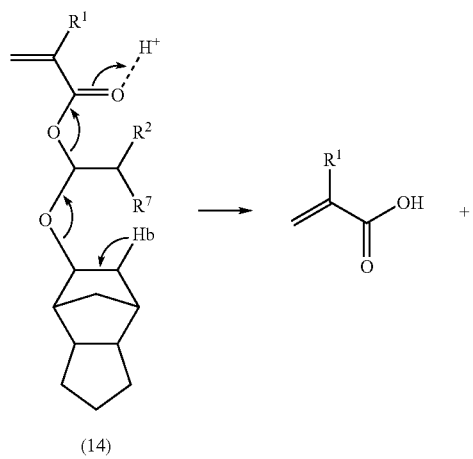

(14)

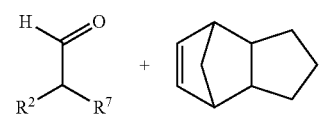

Herein R¹, R² and R⁷ are as defined above.

This is in contrast to the acetal compounds of the invention. In one exemplary compound (15), shown below, corresponding to formula (1) wherein X¹ is a single bond, although β-hydrogen (=Hb) is present in the alcohol moiety of acetal, no double bond can be formed within the adamantane ring due to Bredt's rule, and no acid decomposition by β-elimination in this route can occur. This, combined with the previous description, makes it possible to mitigate excessive acid reactivity, the drawback of acetal type leaving group.

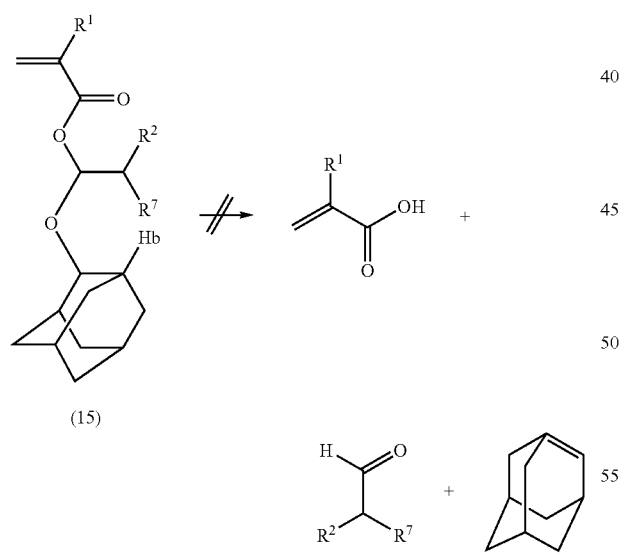

It is noted that WO 2003/006407 discloses conceptually a broad range of structure containing an acetal compound having formula (1) disclosed herein. Synthesis process is nowhere disclosed. It was uncertain for those skilled in the art at that time how to produce a compound having an adamantane ring in the alcohol moiety of acetal.

It is thus believed that the present invention first discloses in a substantial sense acetal compounds whose carbonyl moiety has a branched structure and whose alcohol moiety has an adamantane ring. Also synthesis of such acetal compounds is first disclosed herein.

Polymer

In the fourth embodiment, the invention provides a polymer or high-molecular-weight compound comprising recurring units derived from the acetal compound of formula (1).

Specifically, the recurring units derived from the acetal compound of formula (1) include units having the general formula (8).

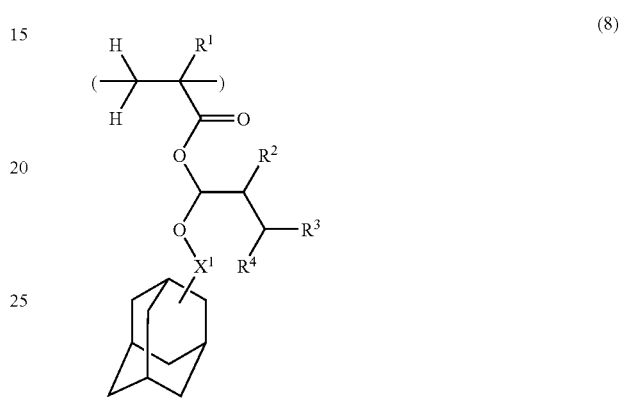

Herein R¹ to R⁴, and X¹ are as defined above.

In addition to the recurring units derived from the acetal compounds having formula (1), specifically recurring units having formula (8), the polymers of the invention may further comprise recurring units of at least one type selected from the general formulas (9) to (12).

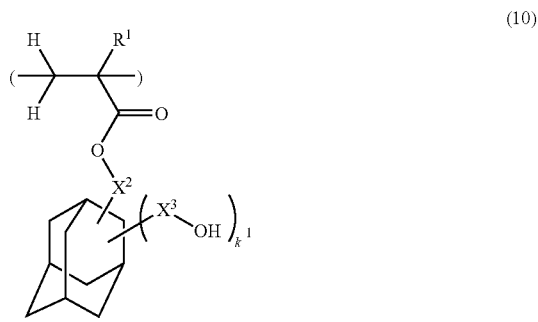

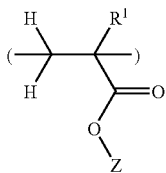

(12)

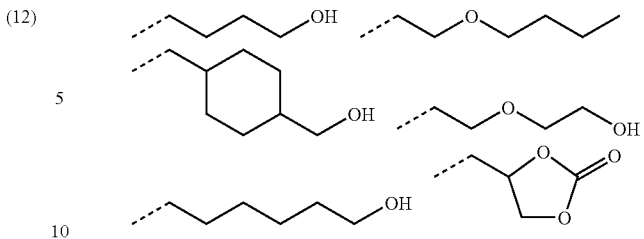

Herein $R^1$ is as defined above, X is an acid labile group different from formula (8), Y is a substituent group having a lactone structure, Z is hydrogen, a $C_1$-$C_{15}$ fluoroalkyl group or a $C_1$-$C_{15}$ fluoroalcohol-containing substituent group, $X^2$ and $X^3$ are each independently a single bond or a straight or branched divalent $C_1$-$C_4$ hydrocarbon group, typically alkylene, and $k^1$ is an integer of 1 to 3.

Under the action of acid, a polymer comprising recurring units of formula (9) is decomposed to generate carboxylic acid, turning to be an alkali soluble polymer. The acid labile group represented by X may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

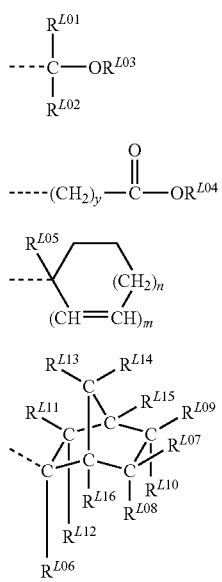

In these formulae, the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, n-propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the substituted alkyl groups are shown below.

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxy, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

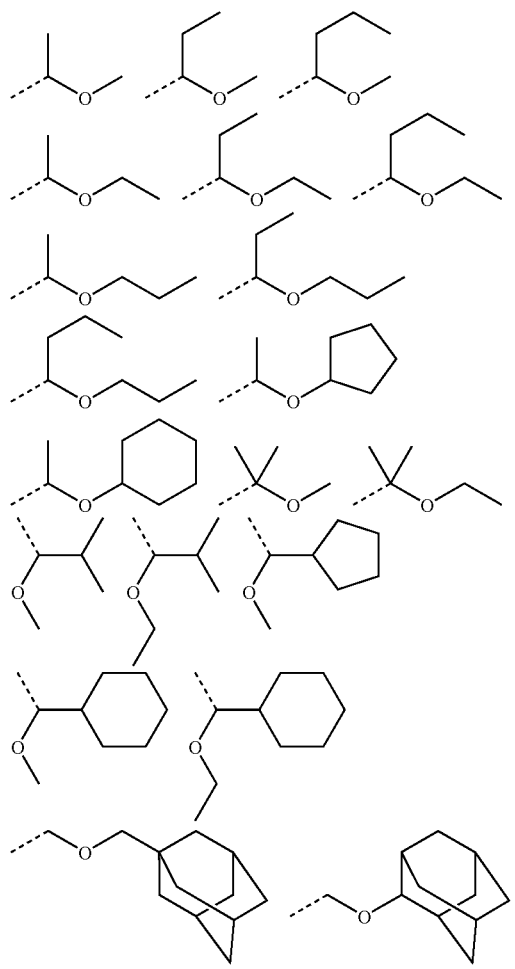

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

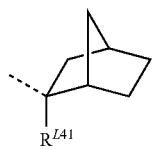

(L4-1)

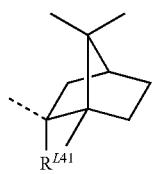

(L4-2)

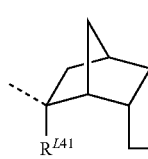

(L4-3)

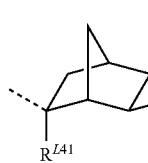

(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

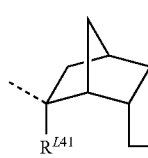

(L4-3-1)

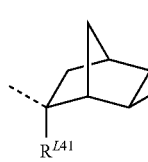

(L4-3-2)

Similarly, the general formula (L4-4) represents one or a mixture of two or more selected from groups having the following general formulas (L4-4-1) to (L4-4-4).

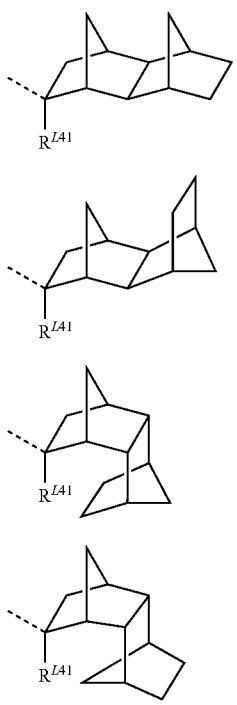

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1] heptane ring, which ensures high reactivity for acid catalyzed elimination reaction (see JP-A 2000-336121). In preparing these monomers having a tertiary exo-alkyl group of bicyclo [2.2.1]heptane skeleton as a substituent group, there may be contained monomers substituted with an endo-alkyl group as represented by the following formulas (L4-1-endo) to (L4-4-endo). For good reactivity, an exo proportion of at least 50% is preferred, with an exo proportion of at least 80% being more preferred.

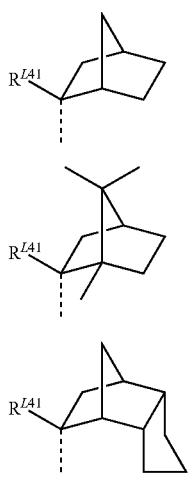

See JP-A 2000-336121.

Illustrative examples of the acid labile group of formula (L4) are given below.

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{L04}$.

Illustrative examples of the recurring units of formula (9) are given below, but not limited thereto.

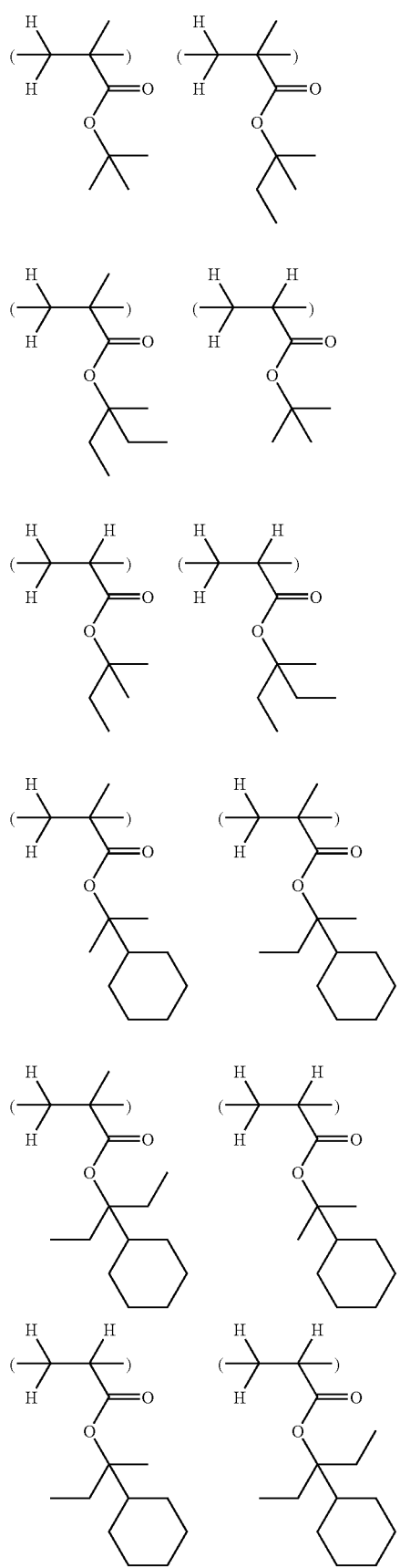
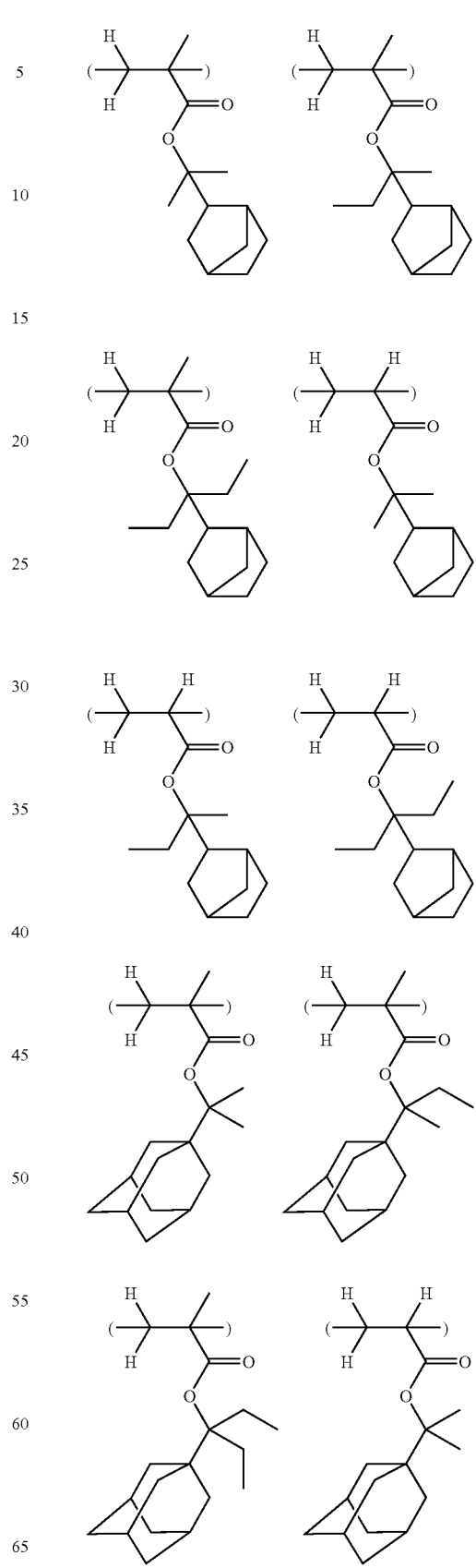

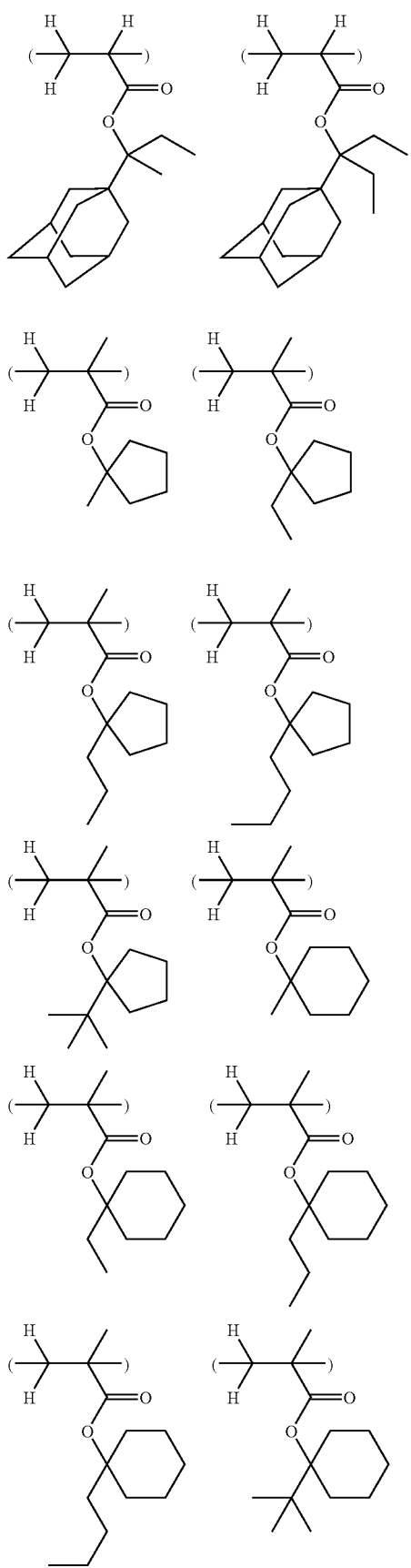
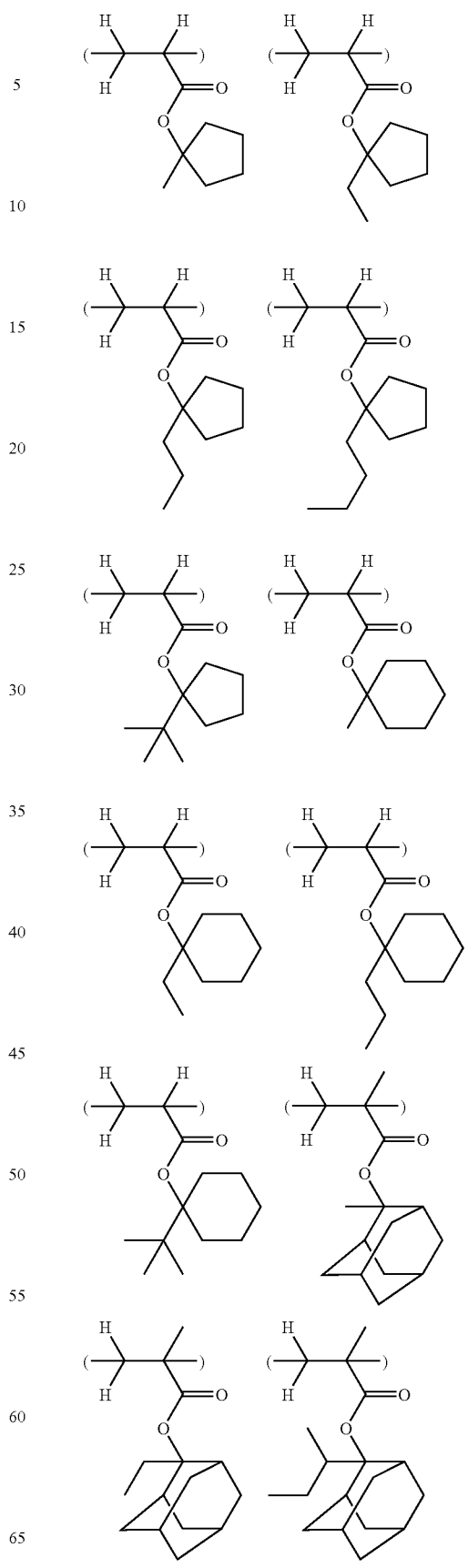

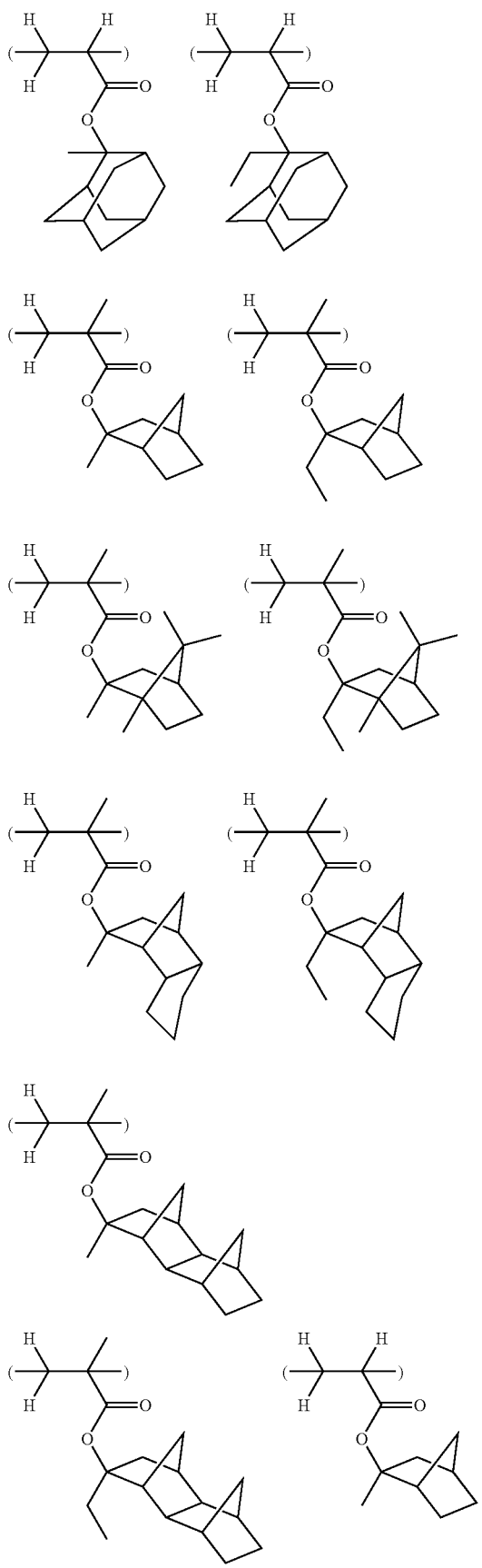
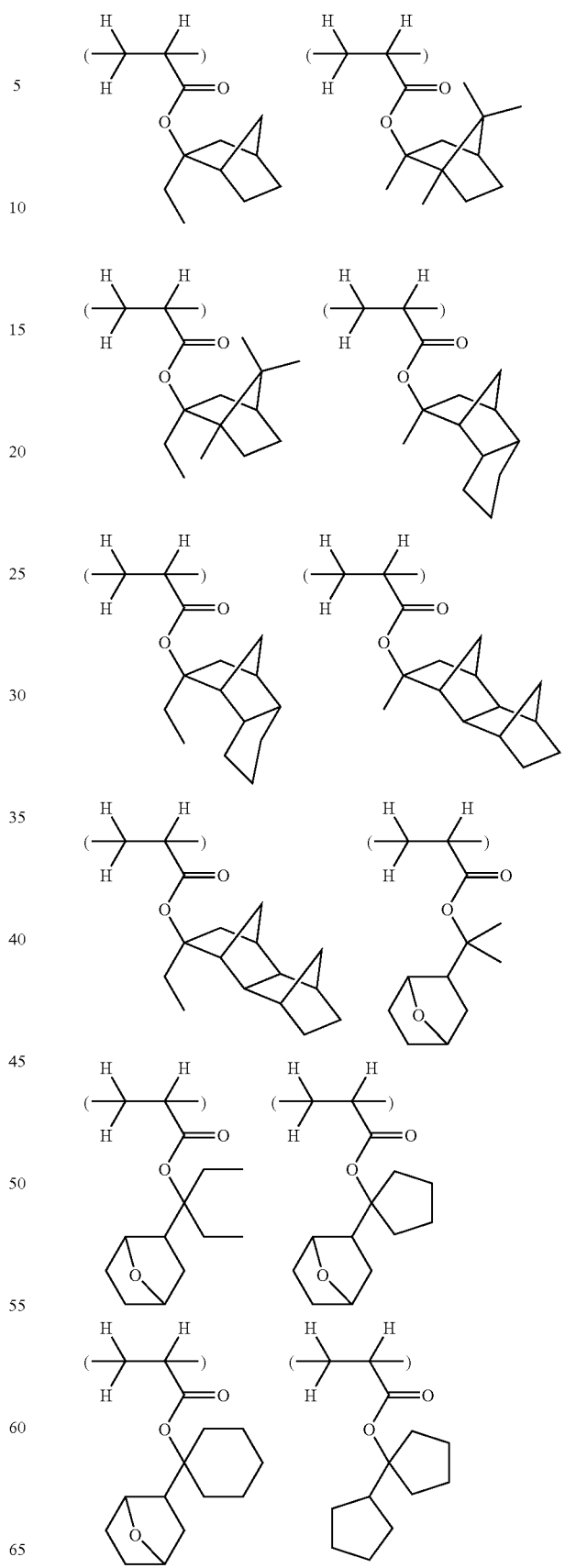

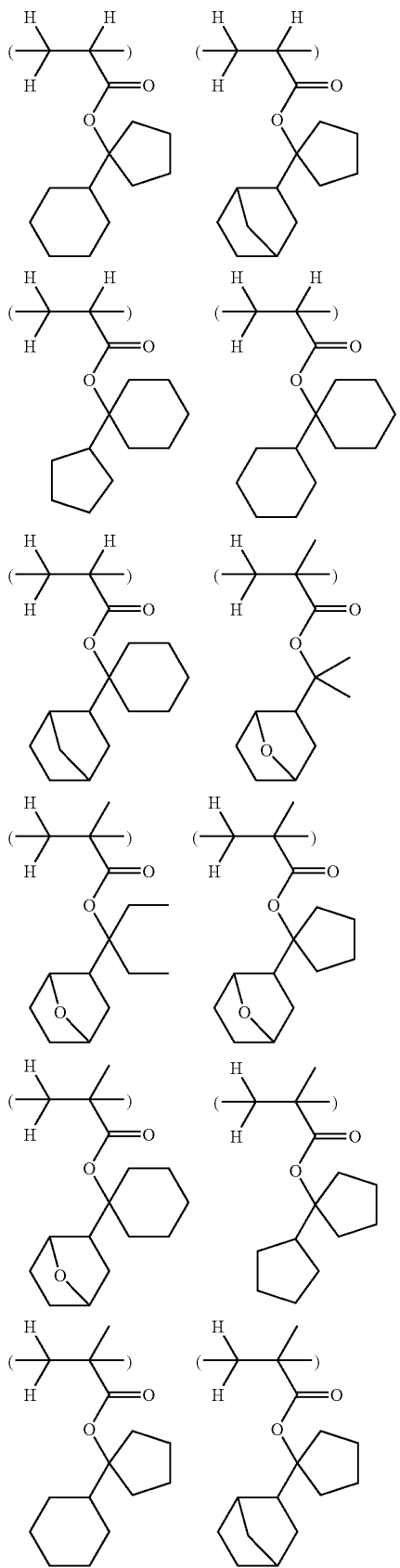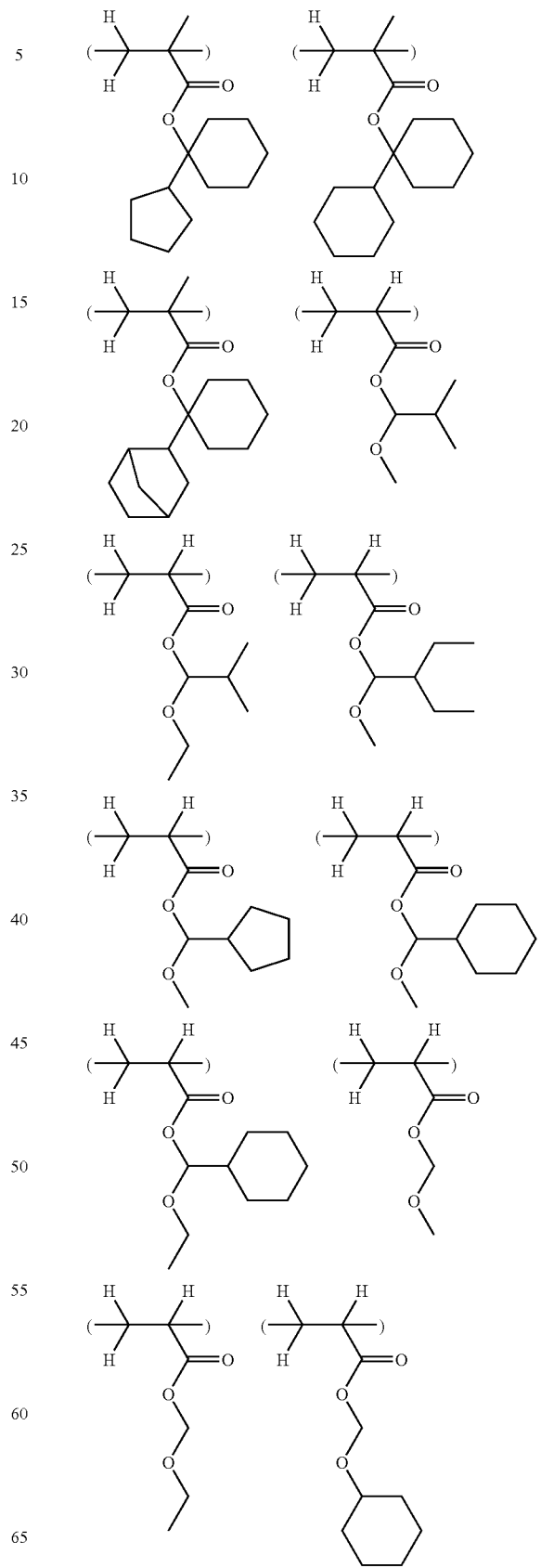

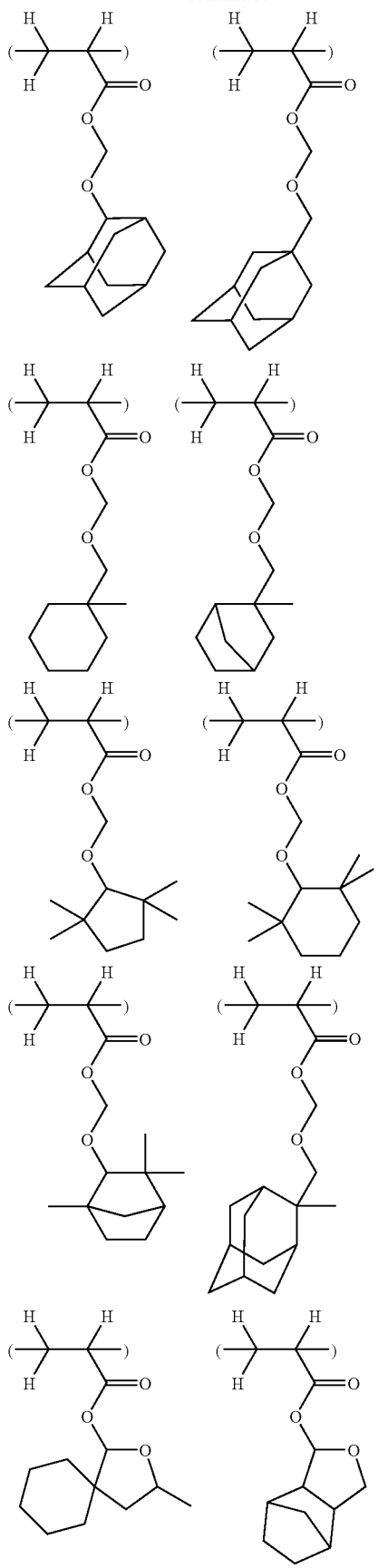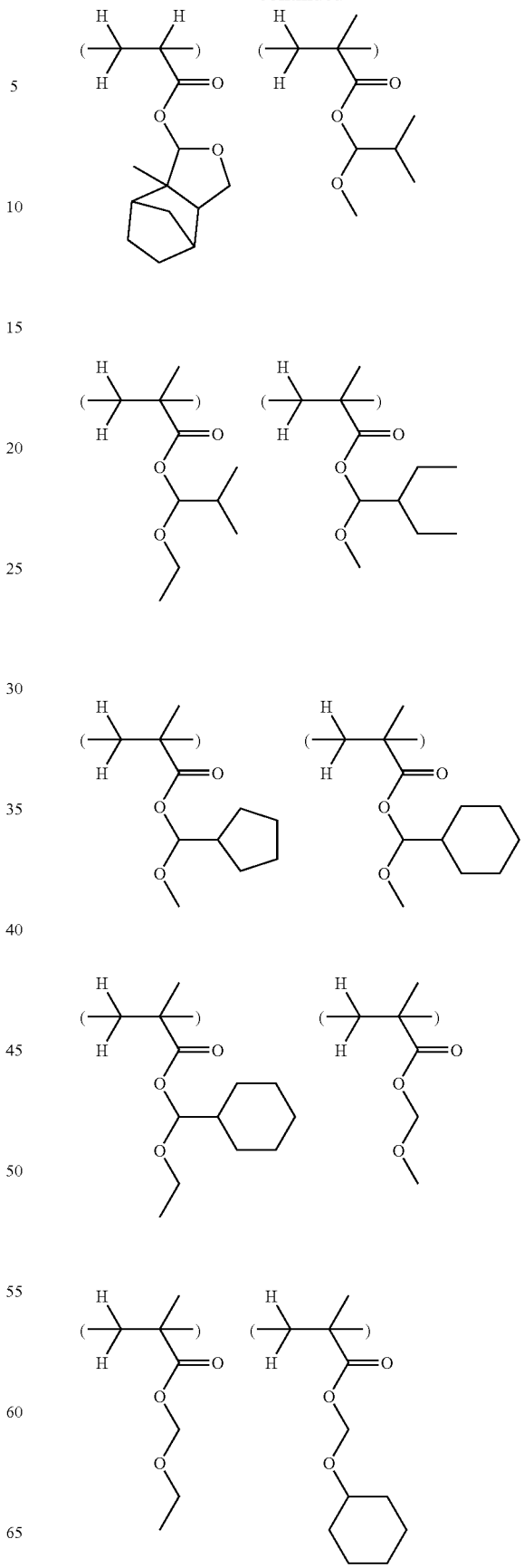

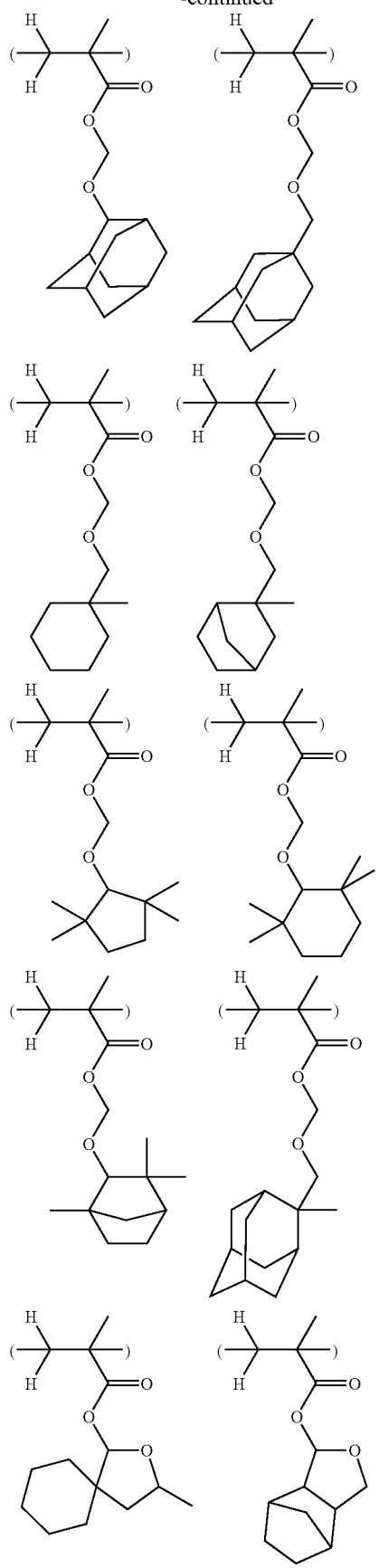
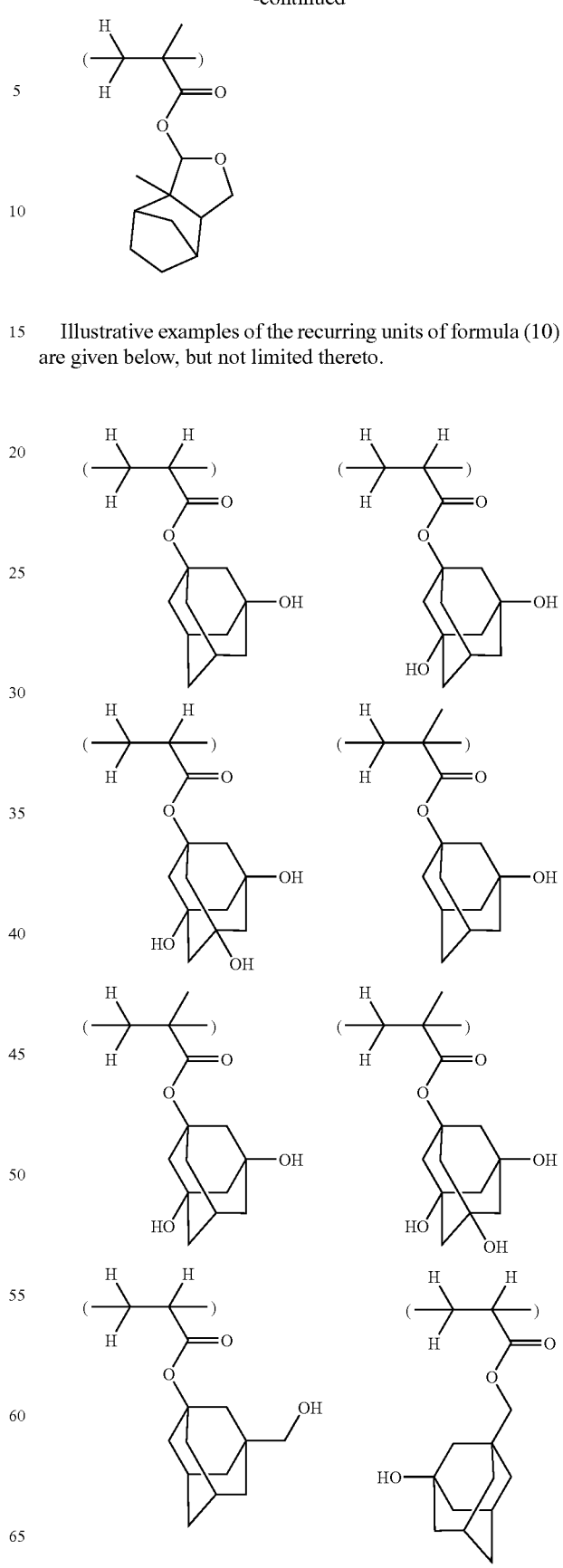
Illustrative examples of the recurring units of formula (10) are given below, but not limited thereto.

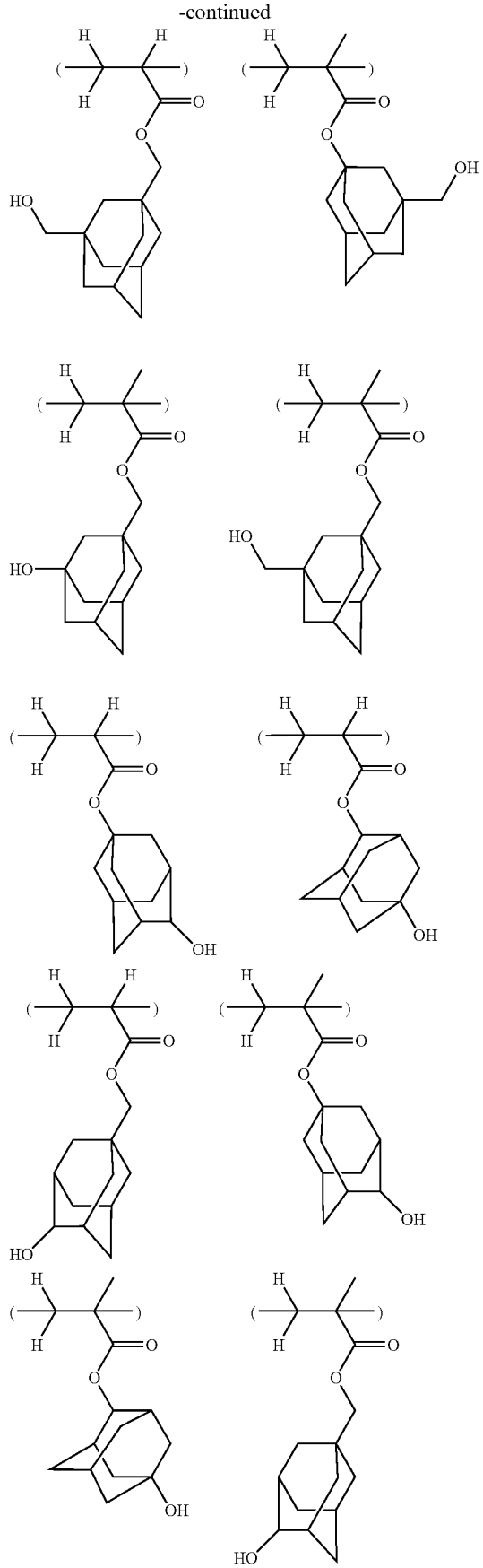
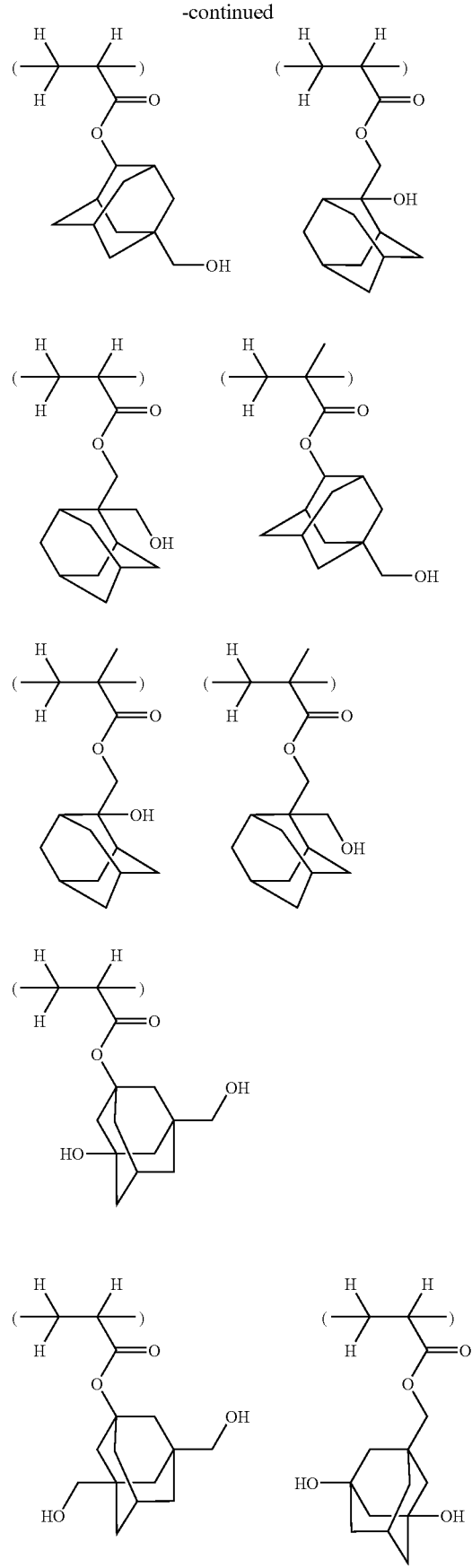

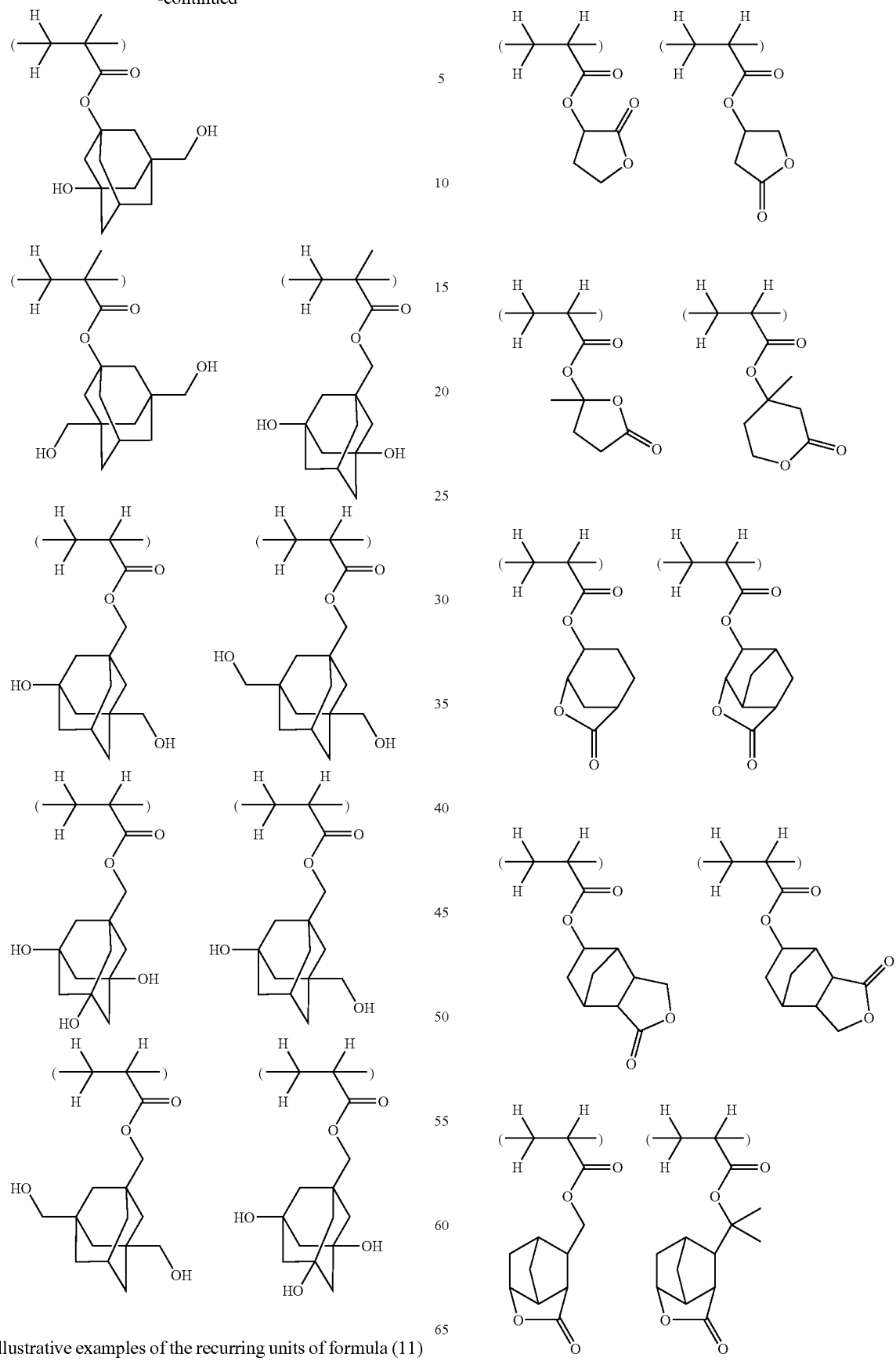
Illustrative examples of the recurring units of formula (11) are given below, but not limited thereto.

-continued
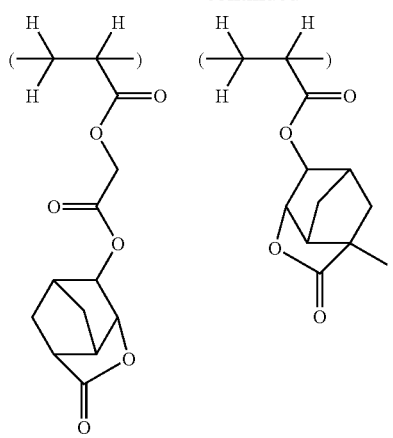
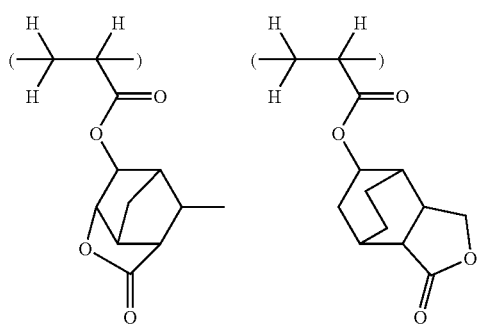
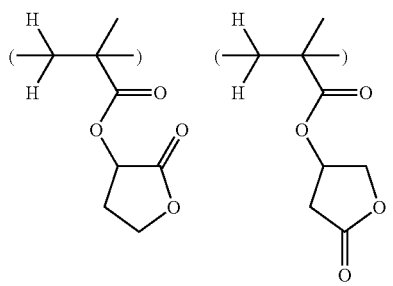
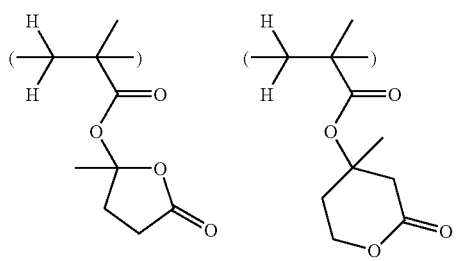
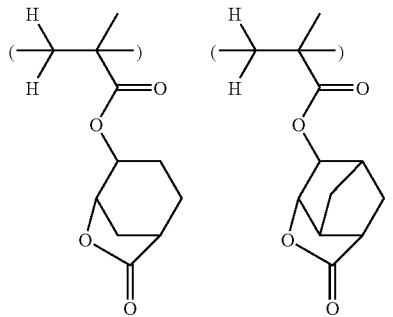
-continued
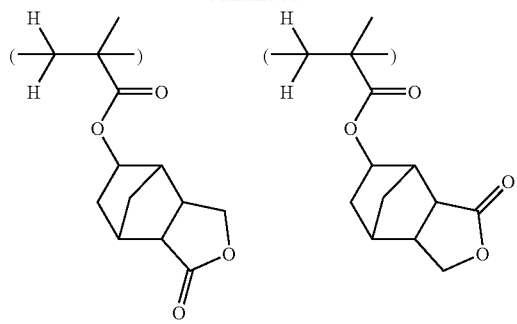
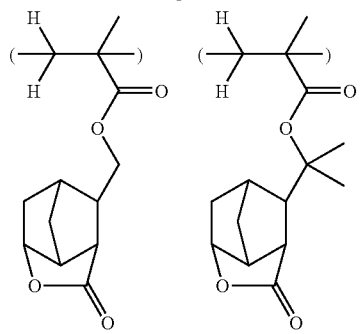
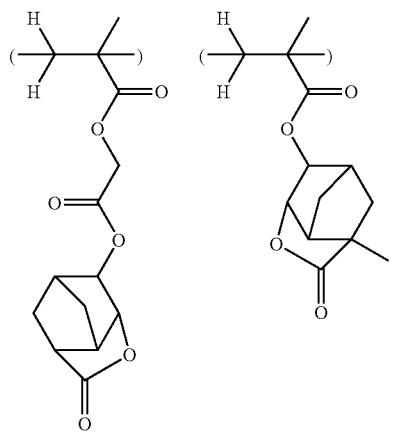
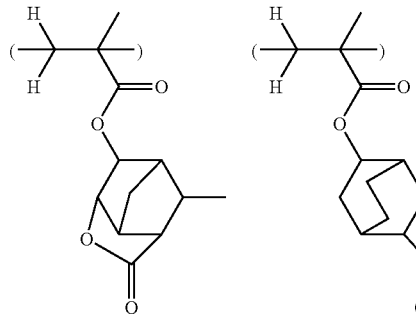
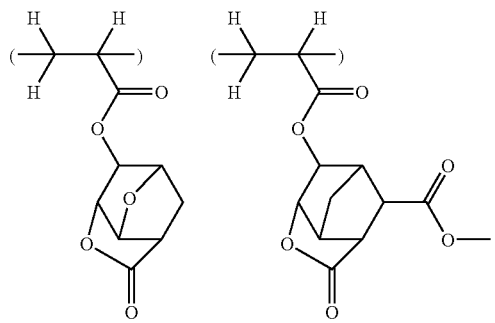

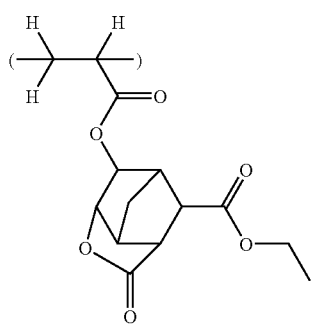
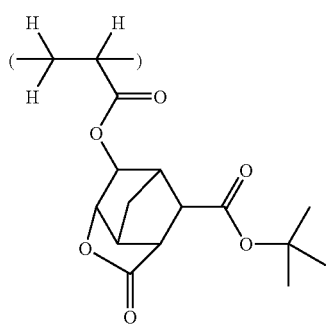
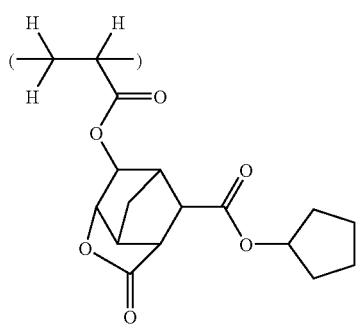
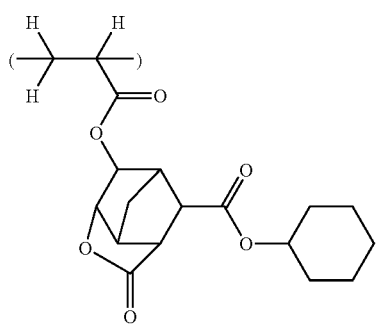
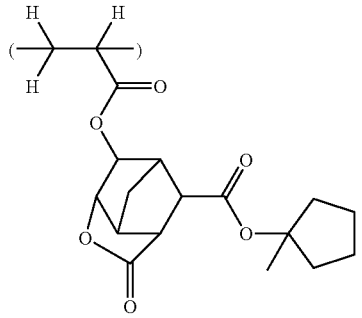
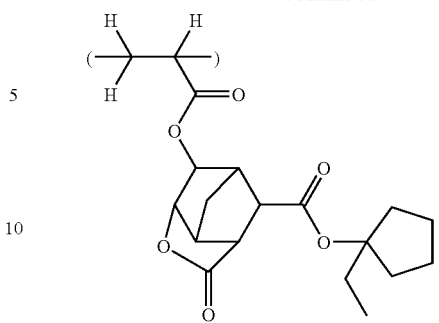
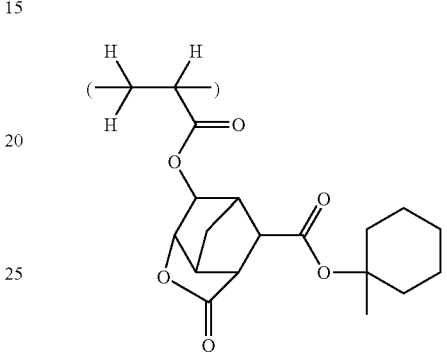
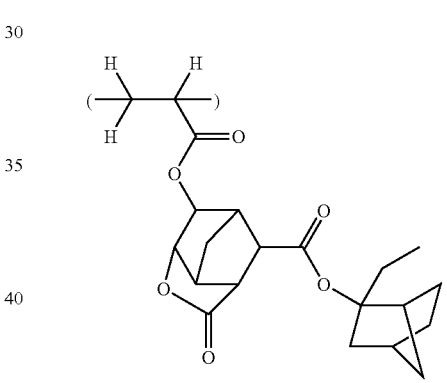
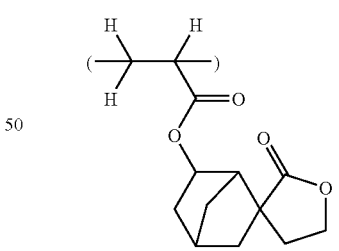
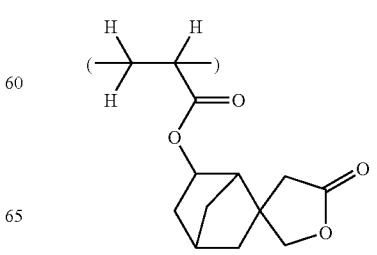

-continued
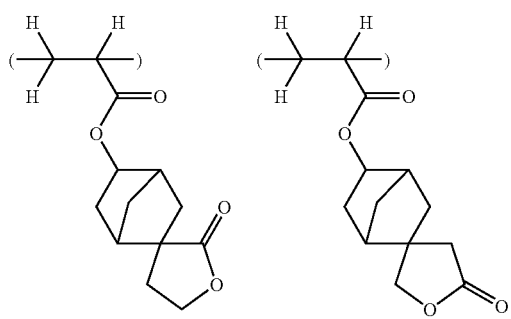
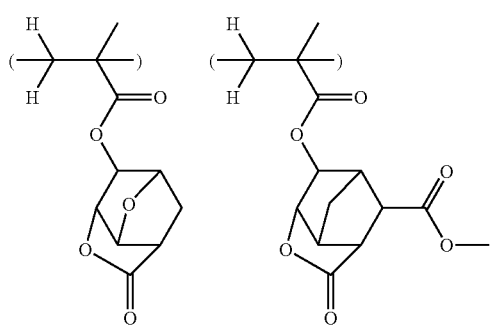
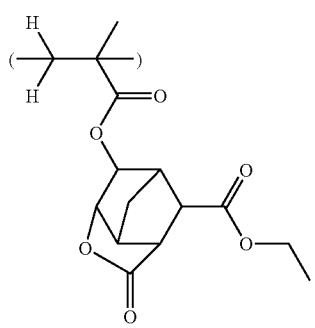
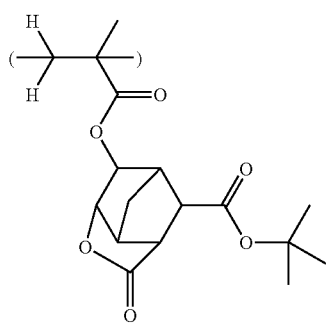
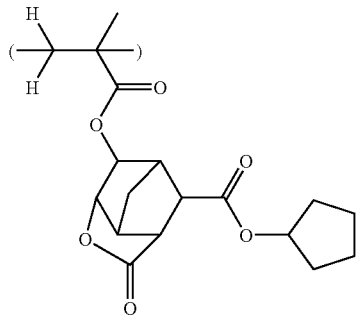
-continued
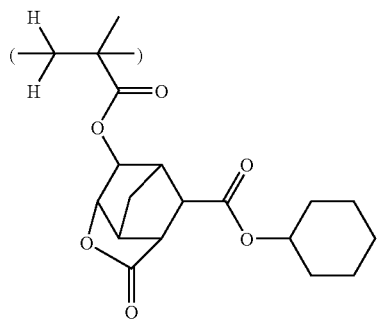
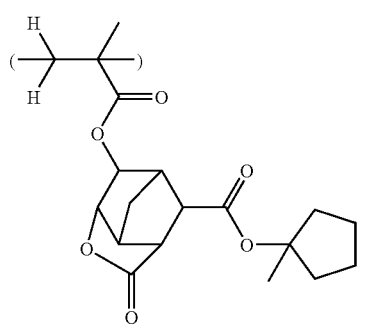
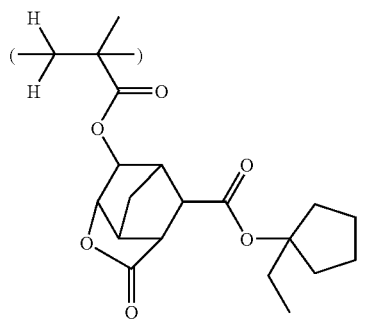
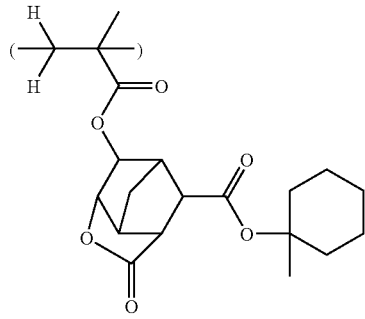
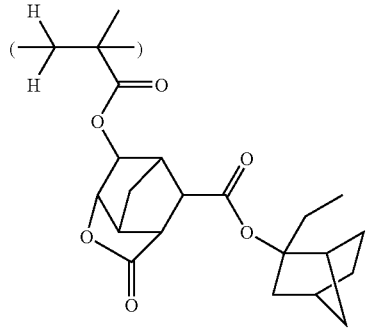

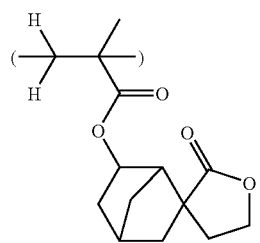
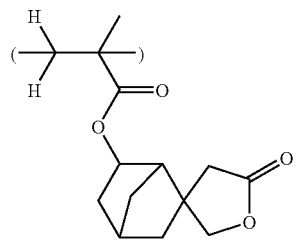
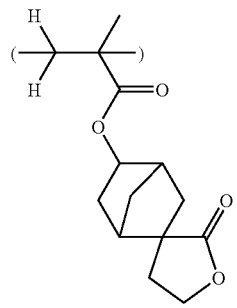
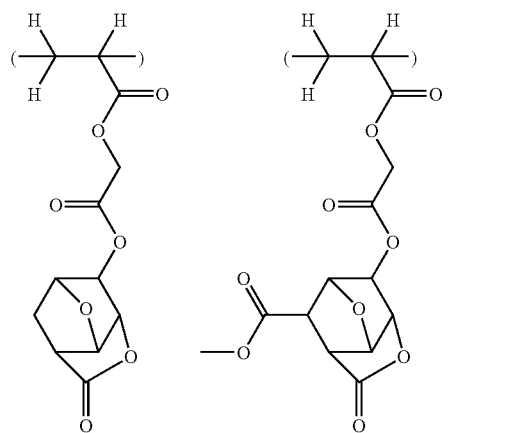
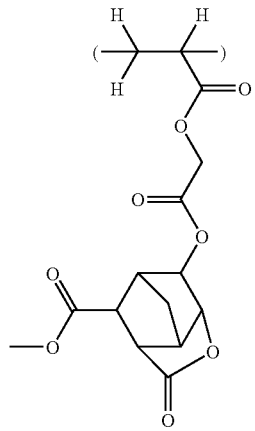
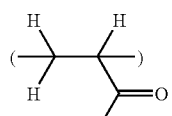
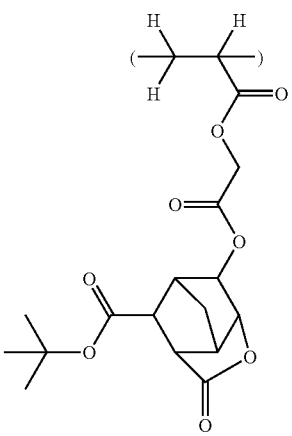
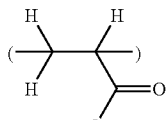
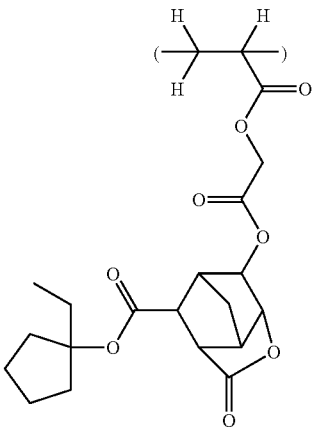
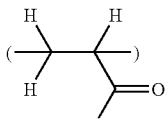
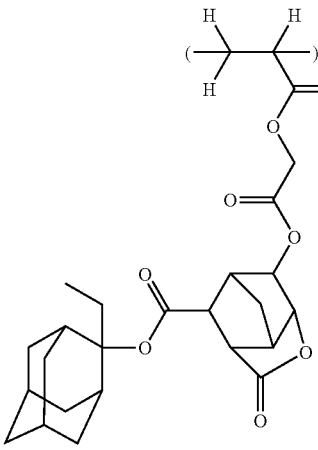

51
-continued
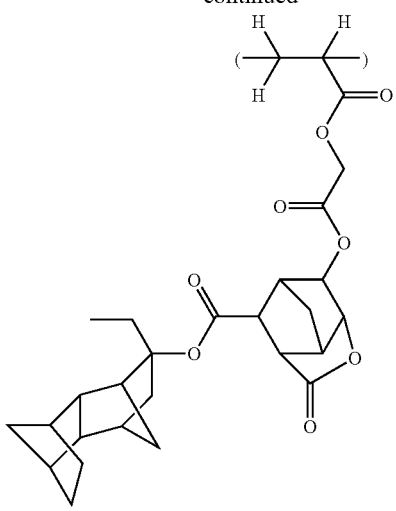
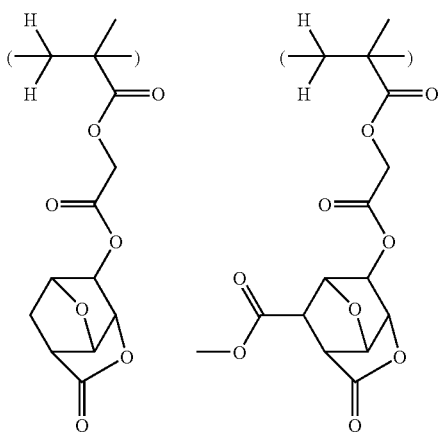
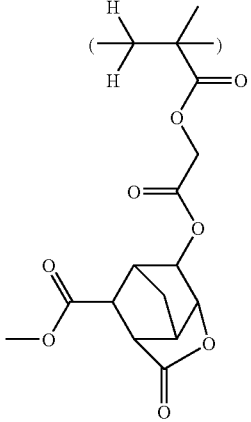
52
-continued
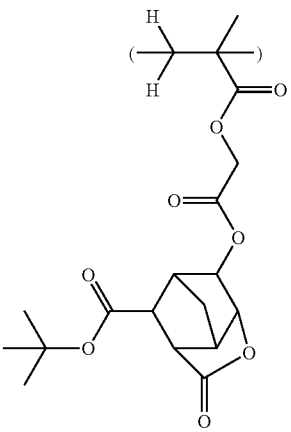
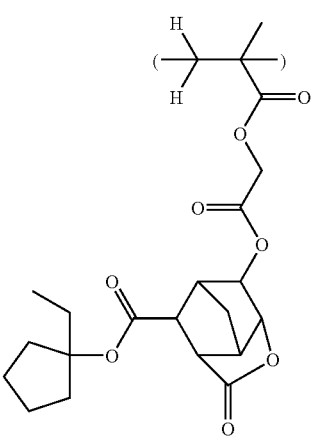
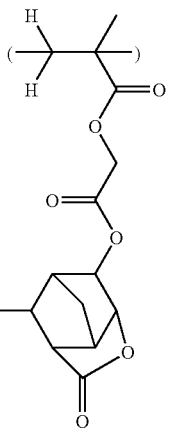

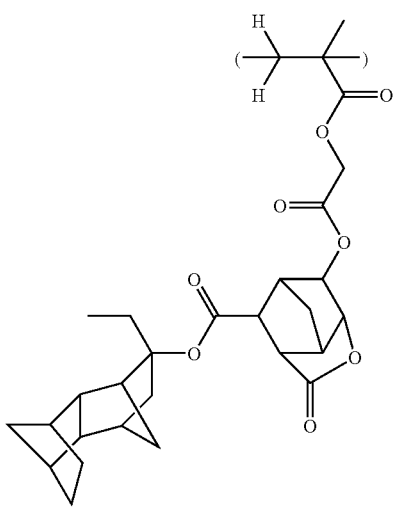
Illustrative examples of the recurring units of formula (12) are given below, but not limited thereto.
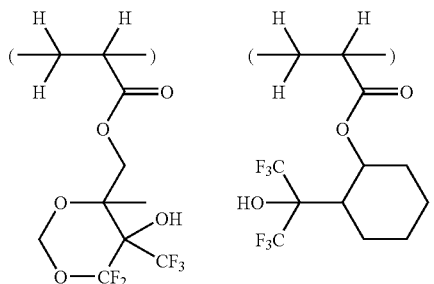
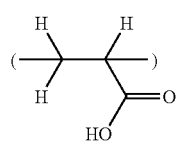
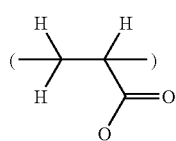
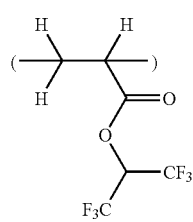
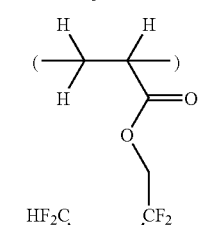
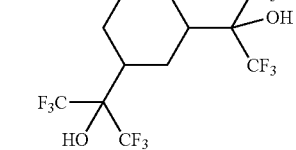
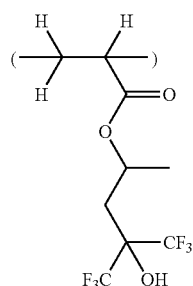
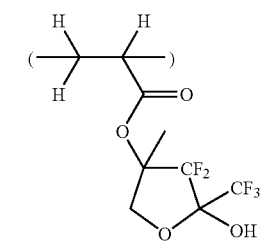
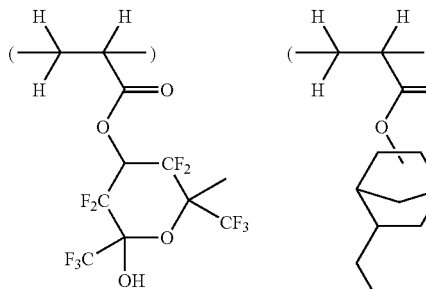
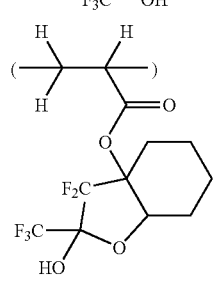
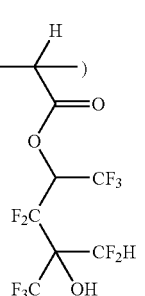
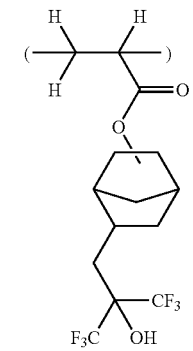
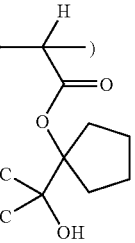
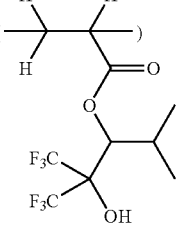
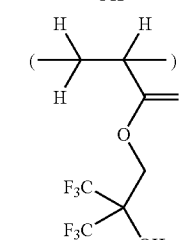

-continued

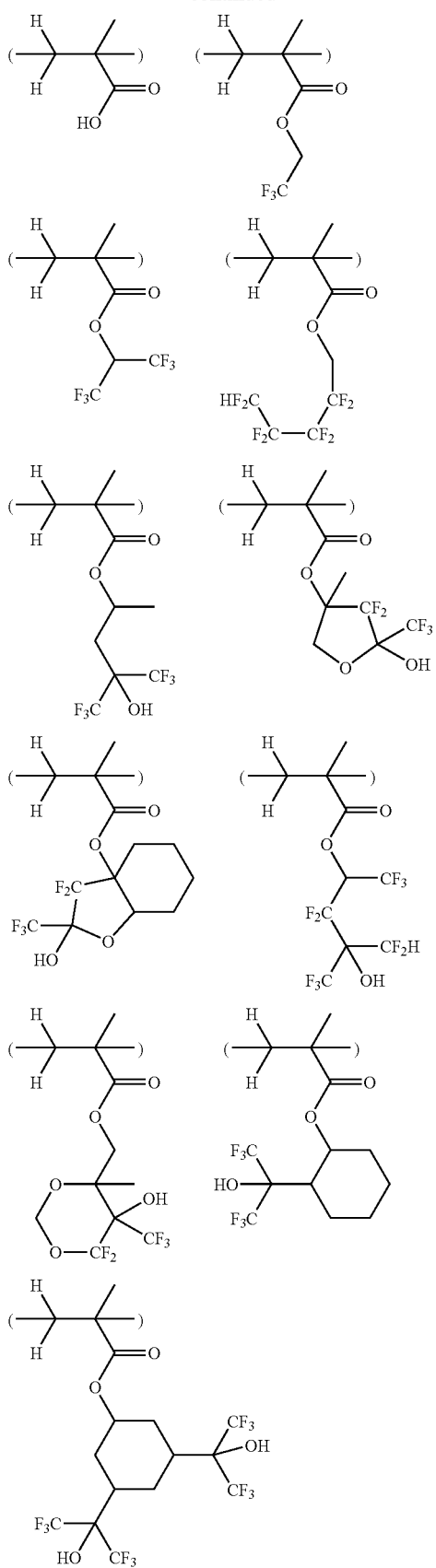
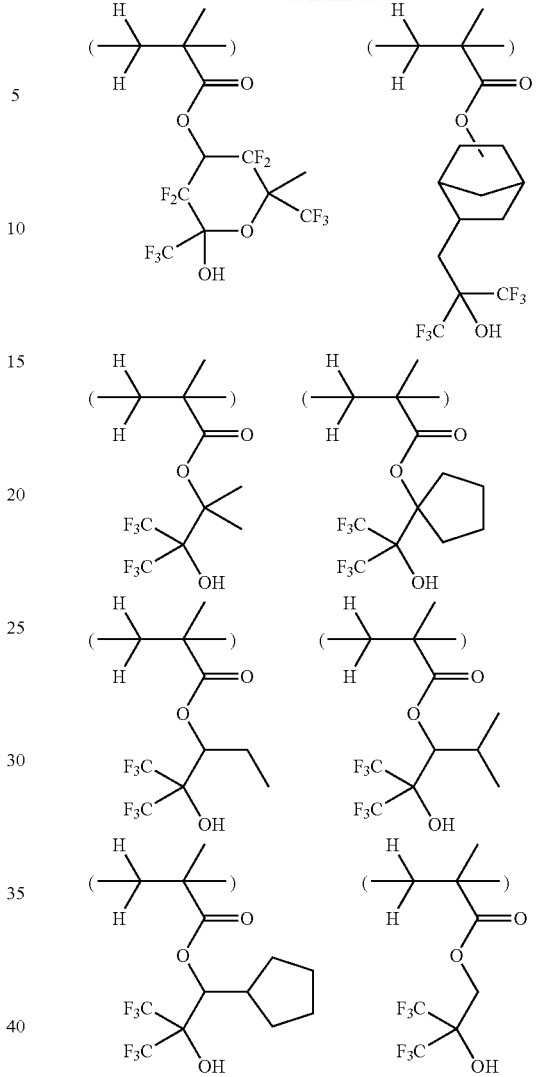

In addition to the foregoing units, the polymers of the invention may further comprise recurring units derived from carbon-to-carbon double bond-bearing monomers other than the above-described ones, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[4.4.0.1$^{2,5}$.17$^{7,10}$]dodecene derivatives, unsaturated acid anhydrides such as itaconic anhydride, and other monomers.

The polymers of the invention generally have a weight average molecular weight (Mw) of 1,000 to 500,000, and preferably 3,000 to 100,000, as measured by gel permeation chromatography (GPC) using polystyrene standards. Outside the range, there may result an extreme drop of etch resistance, and a drop of resolution due to difficulty to gain a dissolution rate difference before and after exposure.

In the inventive polymers, appropriate proportions of the respective recurring units derived from the monomers are given below although the invention is not limited thereto. The inventive polymers may contain:

(I) constituent units of one or more types having formula (8) derived from monomers of formula (1) in a proportion of more than 0 mol % to 100 mol %, preferably 5 to 70 mol %, and more preferably 10 to 50 mol %,
(II) constituent units of one or more types having formulas (9) to (12) in a proportion of 0 mol % to less than 100 mol %, preferably 1 to 95 mol %, more preferably 20 to 90 mol %, even more preferably 30 to 90 mol %, and most preferably 50 to 90 mol %, and optionally,
(III) constituent units of one or more types derived from other monomers in a proportion of 0 to 80 mol %, preferably 0 to 70 mol %, and more preferably 0 to 50 mol %,
based on the total moles of constituent units.

The polymers of the invention are prepared by copolymerization reaction using the compound of formula (1) as a first monomer and polymerizable double bond-bearing compounds as second and subsequent monomers. The copolymerization reaction to produce the inventive polymers may be performed in various modes, preferably radical polymerization, anionic polymerization or coordination polymerization. Preferably the first monomer or compound of formula (1) and the second and subsequent monomers used in copolymerization have an oligomeric or polymeric content of up to 10%, more preferably up to 3%, and even more preferably up to 1%.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base resin of a resist composition, the other aspect of the invention provides a resist composition comprising the polymer and specifically a chemically amplified positive resist composition comprising the polymer. Typically, the positive resist composition contains (A) a base resin comprising the inventive polymer, (B) an acid generator, (C) an organic solvent, and optionally (D) a quencher or organic nitrogen-containing compound, (E) a surfactant, and (F) other components.

In addition to the inventive polymer, the base resin (A) may include another polymer having a dissolution rate in alkaline developer that increases under the action of acid, if necessary. Examples of the other polymer include, but are not limited to, (i) poly(meth)acrylic acid derivatives, (ii) norbornene derivative-maleic anhydride copolymers, (iii) hydrogenated products of ring-opening metathesis polymerization (ROMP) polymers, and (iv) vinyl ether-maleic anhydride-(meth)acrylic acid derivative copolymers.

Of these, the hydrogenated ROMP polymers are synthesized by the method illustrated in JP-A 2003-66612. Illustrative examples of such hydrogenated polymers include those polymers having the recurring units shown below, but are not limited thereto.

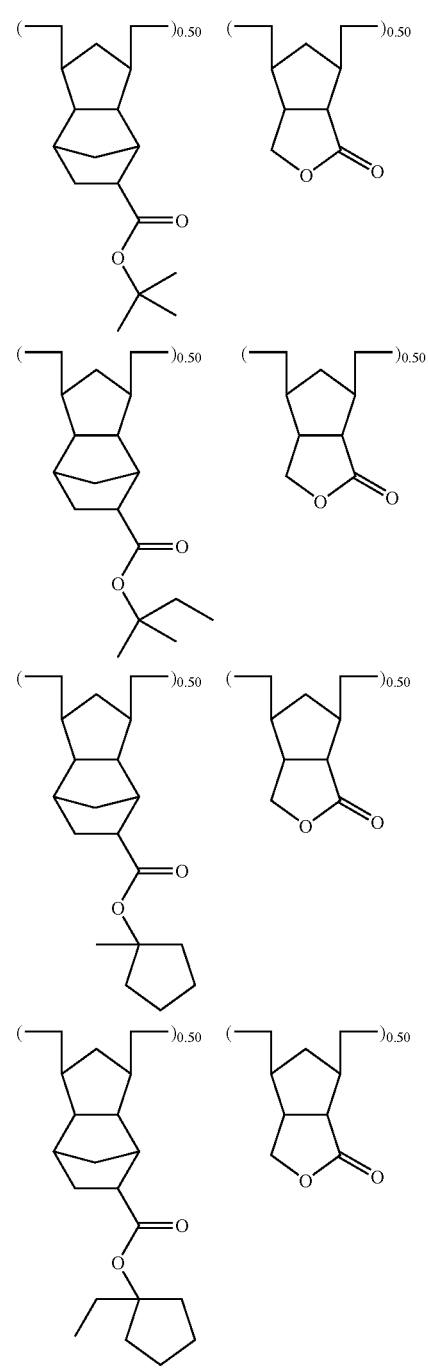

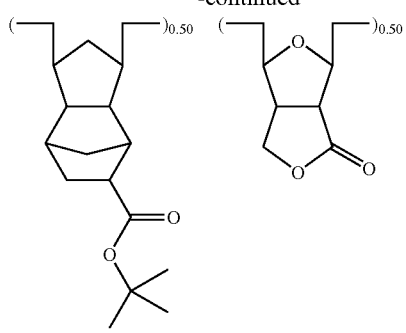
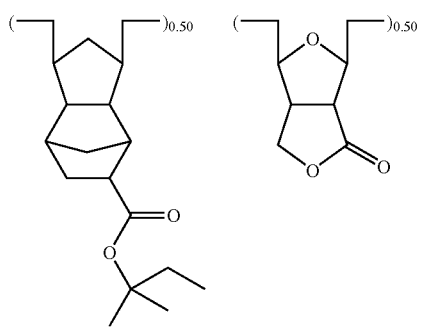
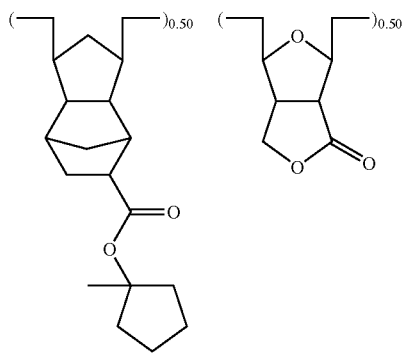
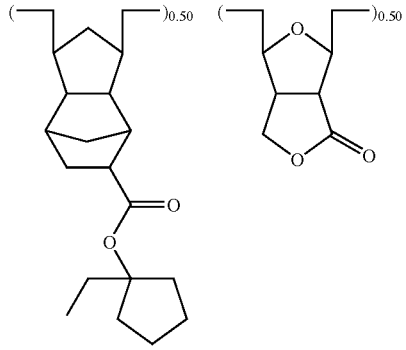
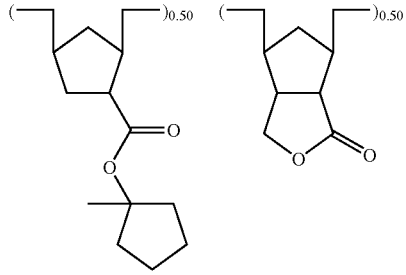
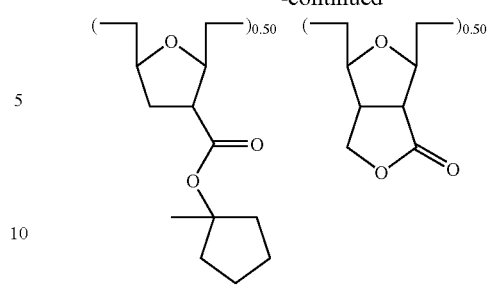
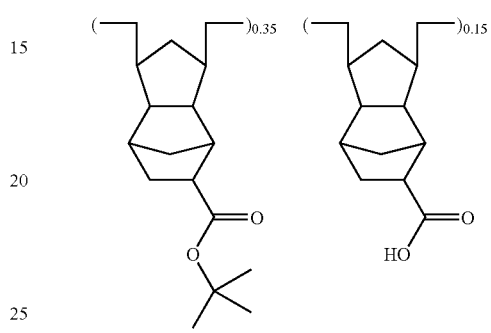
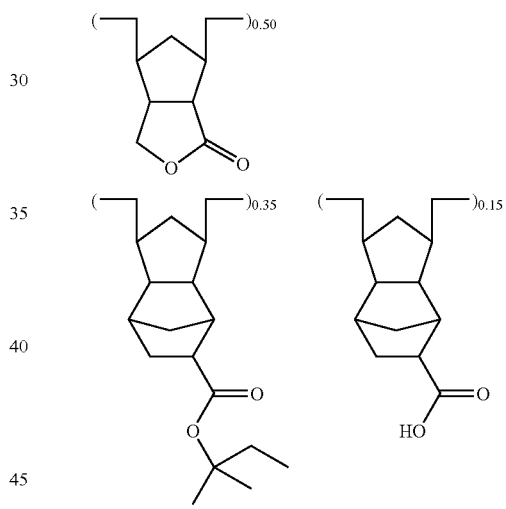
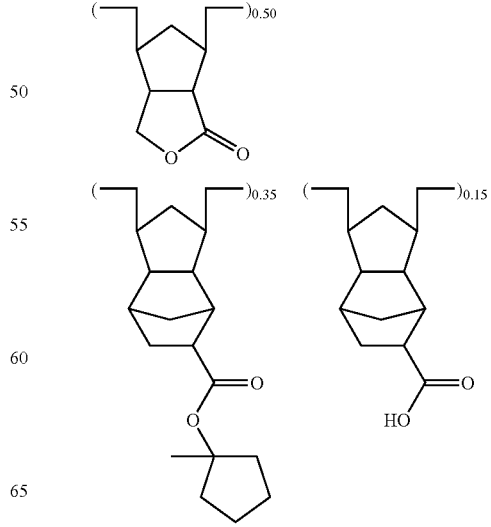

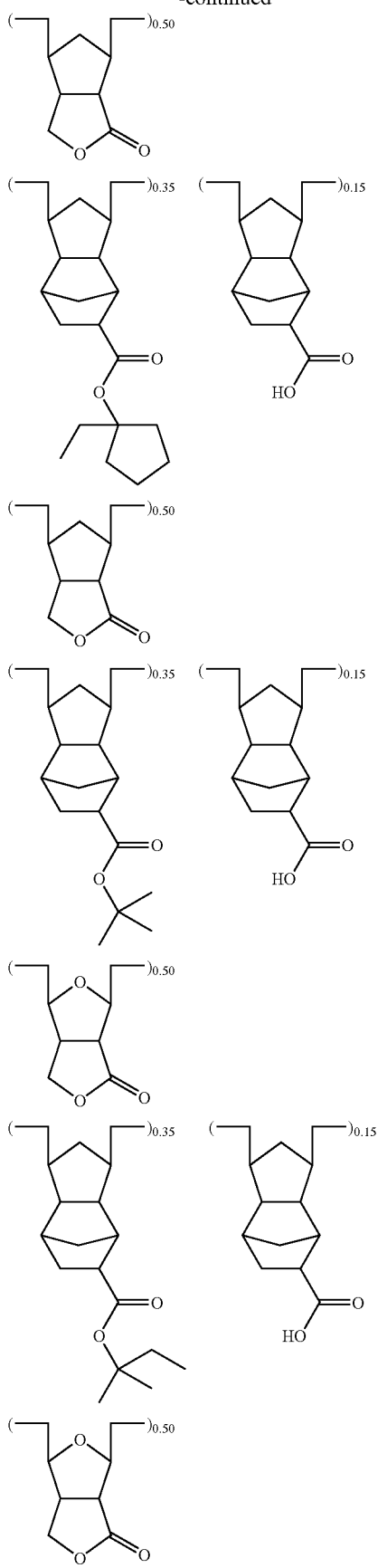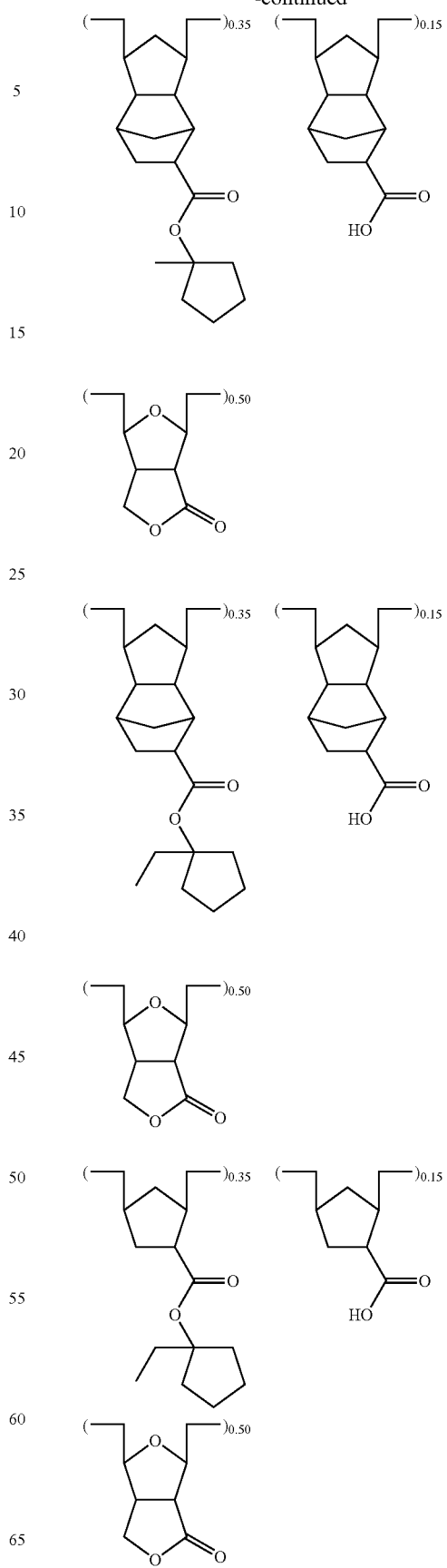

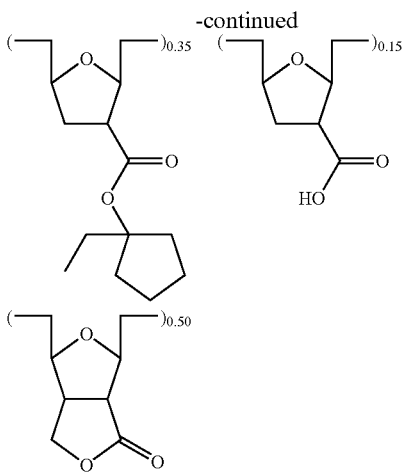

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The polymer is not limited to one type and a mixture of two or more polymers may be added. The use of plural polymers allows for adjustment of resist properties.

Acid Generator

As the acid generator (B), a photoacid generator is typically used. It is any compound capable of generating an acid upon exposure to high-energy radiation. Suitable photoacid generators include sulfonium salts, iodonium salts, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkanesulfonyl)imides and tris(substituted alkanesulfonyl)methides. Exemplary sulfonium cations include triphenylsulfonium, (4-tert-butoxyphenyl) diphenylsulfonium, bis(4-tert-butoxyphenyl) phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl) sulfonium, (4-tert-butoxycarbonylmethyloxyphenyl) diphenylsulfonium, tris(4-tert-butoxycarbonylmethyloxyphenyl)sulfonium, (4-tert-butoxyphenyl)bis(4-dimethylaminophenyl)sulfonium, tris (4-dimethylaminophenyl)sulfonium, 4-methylphenyldiphenylsulfonium, 4-tert-butylphenyldiphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy) naphthalene-2-sulfonate, 4-(p-toluenesulfonyloxy) naphthalene-1-sulfonate, 5-(p-toluenesulfonyloxy) naphthalene-1-sulfonate, 8-(p-toluenesulfonyloxy) naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Exemplary bis(substituted alkanesulfonyl)imides include bis (trifluoromethylsulfonyl)imide, bis(pentafluoroethylsulfonyl)imide, bis(heptafluoropropylsulfonyl)imide, and perfluoro(1,3-propylenebissulfonyl)imide. A typical tris (substituted alkanesulfonyl)methide is tris (trifluoromethylsulfonyl)methide. Sulfonium salts based on combination of the foregoing examples are included.

Iodonium salts are salts of iodonium cations with sulfonates, bis(substituted alkanesulfonyl)imides and tris(substituted alkanesulfonyl)methides. Exemplary iodonium cations include diphenyliodonium, bis(4-tert-butylphenyl) iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy) naphthalene-2-sulfonate, 4-(p-toluenesulfonyloxy) naphthalene-1-sulfonate, 5-(p-toluenesulfonyloxy) naphthalene-1-sulfonate, 8-(p-toluenesulfonyloxy) naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Exemplary bis(substituted alkanesulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkanesulfonyl)methide is tris(trifluoromethylsulfonyl)methide. Iodonium salts based on combination of the foregoing examples are included.

N-sulfonyloxydicarboxylmide photoacid generators include combinations of imide skeletons with sulfonates. Exemplary imide skeletons are succinimide, naphthalenedicarboxylmide, phthalimide, cyclohexyldicarboxylmide, 5-norbornene-2,3-dicarboxyimide, and 7-oxabicyclo[2.2.1]-5-heptene-2,3-dicarboxylmide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthyl-ethanesulfonate, 1,1,2,2-tetrafluoro-2-(norbornan-2-yl)ethanesulfonate, 1,1,2,2-tetrafluoro-2-(tetracyclo[6.2.1.1$^{3,6}$.0$^{2,7}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Suitable oxime sulfonate photoacid generators in the form of O-arenesulfonyloxime and O-alkanesulfonyloxime compounds include oxime sulfonates having an electron withdrawing group such as trifluoromethyl incorporated for increased stability, as represented by the formula (Ox-1).

$$Ar^{401}-\overset{OR^{401}}{\underset{\parallel}{\underset{C}{N}}}-R^{402} \quad \text{(Ox-1)}$$

Herein $R^{401}$ is a substituted or unsubstituted $C_1$-$C_{10}$ haloalkanesulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include
2-[2,2,3,3,4,4,5,5-octafluoro-1-(nonafluorobutylsulfonyloxy-imino)-pentyl]fluorene,
2-[2,2,3,3,4,4-pentafluoro-1-(nonafluorobutylsulfonyloxy-imino)butyl]fluorene,
2-[2,2,3,3,4,4,5,5,6,6-decafluoro-1-(nonafluorobutylsulfonyl-oxyimino)hexyl]fluorene,
2-[2,2,3,3,4,4,5,5-octafluoro-1-(nonafluorobutylsulfonyloxy-imino)pentyl]-4-biphenyl,
2-[2,2,3,3,4,4-pentafluoro-1-(nonafluorobutylsulfonyloxy-imino)butyl]-4-biphenyl, and
2-[2,2,3,3,4,4,5,5,6,6-decafluoro-1-(nonafluorobutylsulfonyl-oxyimino)hexyl]-4-biphenyl.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl) difluoromethanesulfonate, and 4-oxo-1-adamantyloxycarbonyldifluoromethanesulfonate.

Among others, acid generators having the general formula (16) are preferred.

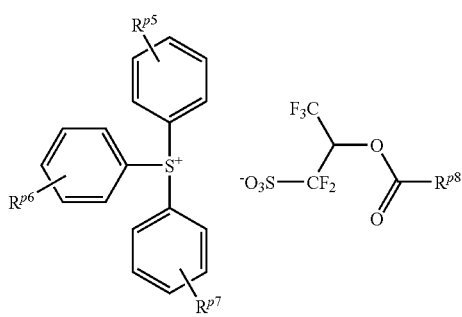

(16)

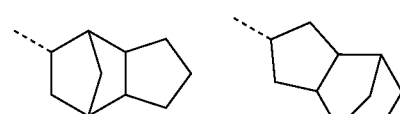

Herein $R^{p5}$, $R^{p6}$, and $R^{p7}$ are each independently hydrogen or a straight, branched or cyclic, monovalent $C_1$-$C_{20}$ hydrocarbon group which may contain a heteroatom. Examples of hydrocarbon groups optionally containing a heteroatom include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, butyladamantyl, and modified forms of the foregoing in which any carbon-to-carbon bond is separated by a hetero-atomic grouping such as —O—, —S—, —SO—, —SO$_2$—, —NH—, —C(=O)—, —C(=O)O—, or —C(=O)NH—, or any hydrogen atom is replaced by a functional group such as —OH, —NH$_2$, —CHO, or —CO$_2$H. $R^{p8}$ is a straight, branched or cyclic, monovalent $C_7$-$C_{30}$ hydrocarbon group which may contain a heteroatom, examples of which are exemplified below, but are not limited thereto.

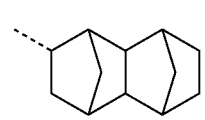

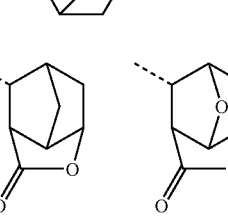

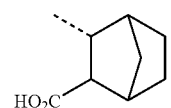

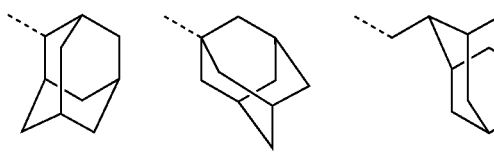

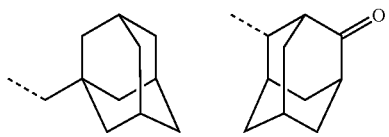

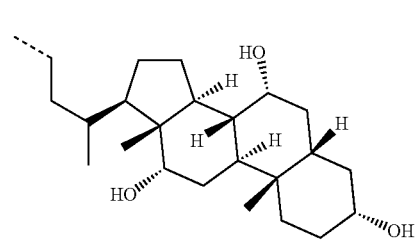

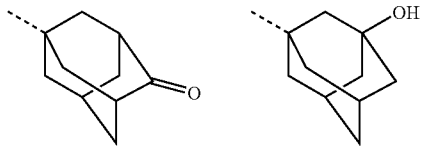

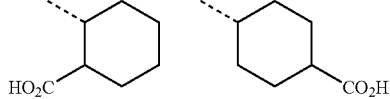

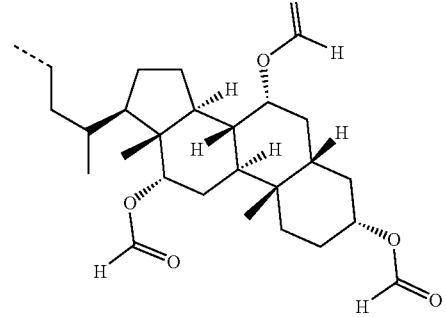

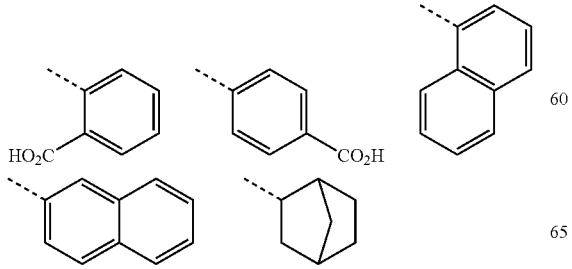

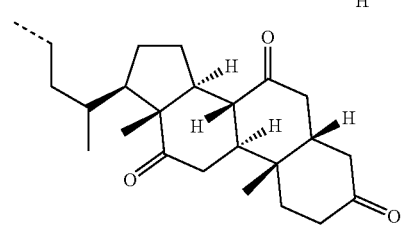

Illustrative examples of acid generators (16) are shown below.

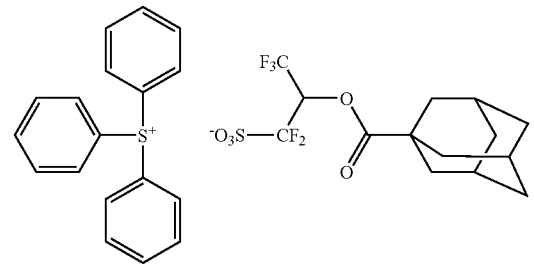

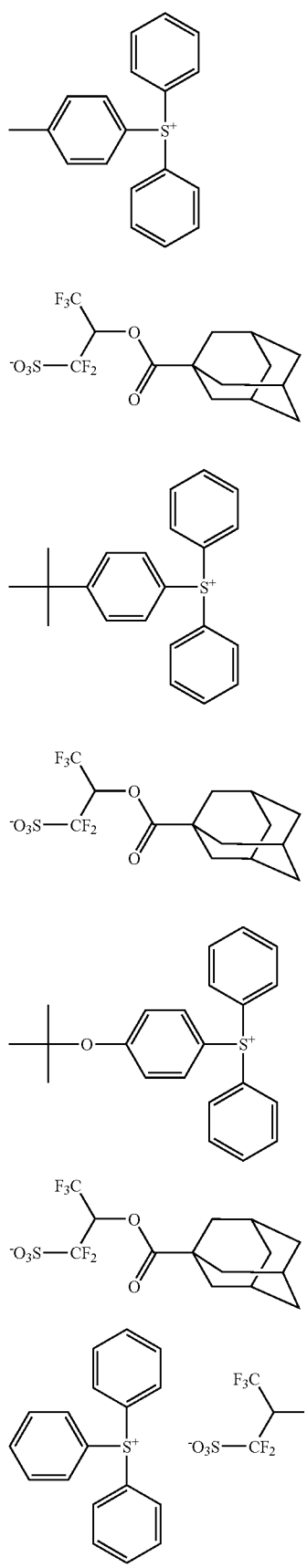
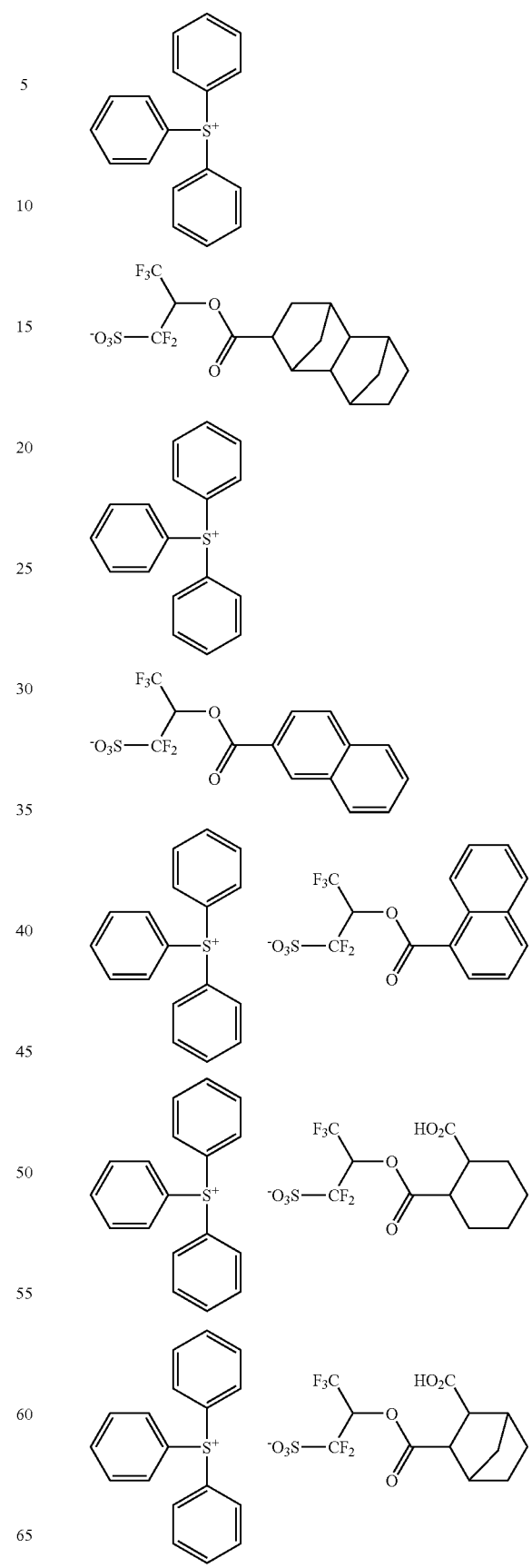

-continued

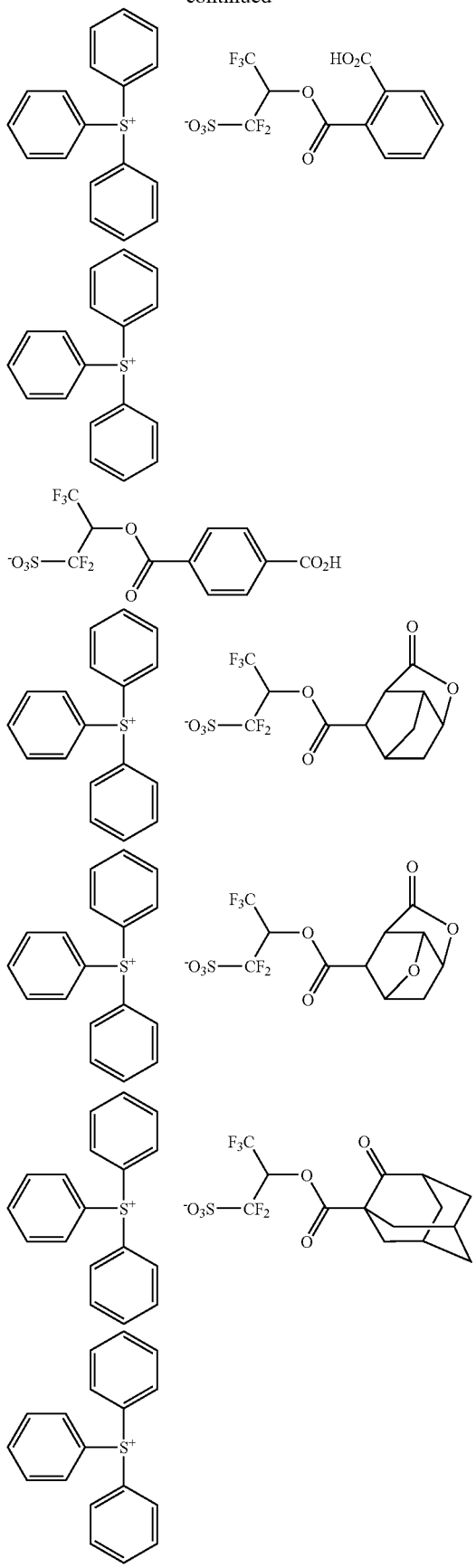
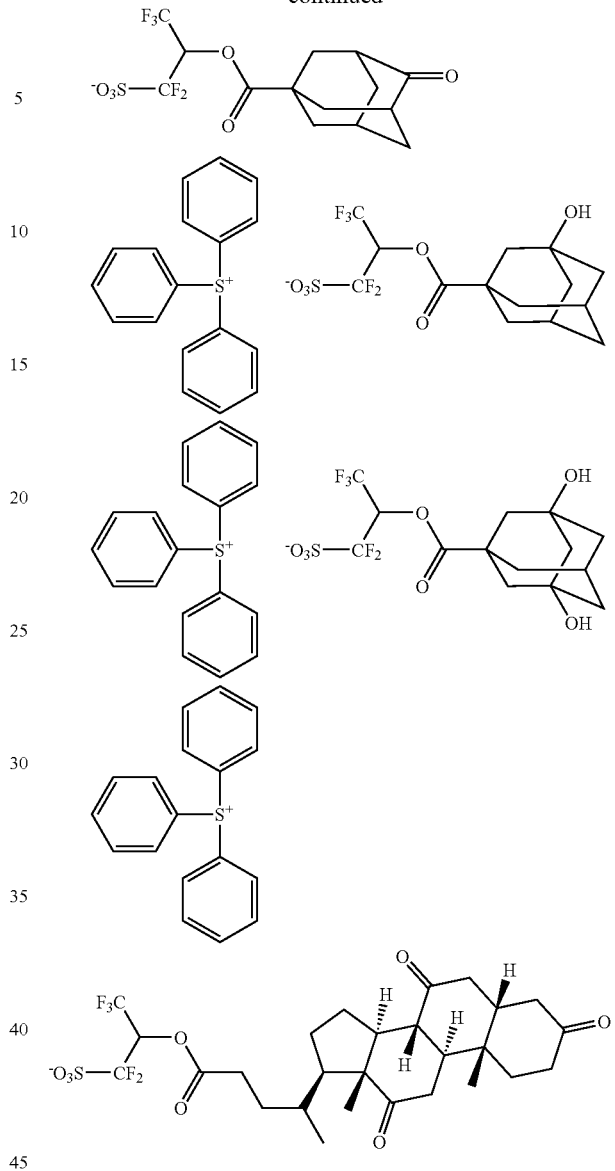

In the chemically amplified resist composition, the photoacid generator (B) may be added in any desired amount as long as the objects of the invention are not compromised. An appropriate amount of the photoacid generator (B) is 0.1 to 10 parts, and more preferably 0.1 to 5 parts by weight per 100 parts by weight of the base resin in the composition. Too high a proportion of the photoacid generator (B) may give rise to problems of degraded resolution and foreign matter upon development and resist film peeling. The photoacid generators may be used alone or in admixture of two or more. The transmittance of the resist film can be controlled by using an photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., nonfluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid is used, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Organic Solvent

The organic solvent (C) used herein may be any organic solvent in which the base resin, acid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, PGMEA, and mixtures thereof because the acid generator is most soluble therein.

An appropriate amount of the organic solvent used is 200 to 3,000 parts, especially 400 to 2,500 parts by weight per 100 parts by weight of the base resin.

Nitrogen-Containing Compound

In the resist composition, an organic nitrogen-containing compound or compounds (D) may be compounded. The organic nitrogen-containing compound used herein is preferably a compound capable of suppressing the rate of diffusion when the acid generated by the acid generator diffuses within the resist film. The inclusion of this type of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

The organic nitrogen-containing compound may be any of well-known organic nitrogen-containing compounds used in conventional resist compositions, typically chemically amplified resist compositions. Examples of organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, carbamate derivatives, and ammonium salts.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

Examples of suitable ammonium salts include pyridinium p-toluenesulfonate, triethylammonium p-toluenesulfonate, trioctylammonium p-toluenesulfonate, triethylammonium 2,4,6-triisopropylbenzenesulfonate, trioctylammonium 2,4,6-triisopropylbenzenesulfonate, triethylammonium camphorsulfonate, trioctylammonium camphorsulfonate, tetramethylammonium hydroxide, tetraethylammonium hydroxide, tetrabutylammonium hydroxide, benzyltrimethylammonium hydroxide, tetramethylammonium, p-toluenesulfonate, tetrabutylammonium p-toluenesulfonate, benzyltrimethylammonium p-toluenesulfonate, tetramethylammonium camphorsulfonate, tetrabutylammonium camphorsulfonate, benzyltrimethylammonium camphorsulfonate, tetramethylammonium 2,4,6-triisopropylbenzenesulfonate, tetrabutylammonium 2,4,6-triisopropylbenzenesulfonate, benzyltrimethylammonium 2,4,6-triisopropylbenzenesulfonate, tetramethylammonium acetate, tetrabutylammonium acetate, benzyltrimethylammonium acetate, tetramethylammonium benzoate, tetrabutylammonium benzoate, and benzyltrimethylammonium benzoate.

In addition, organic nitrogen-containing compounds of the following general formula (B)-1 may also be included alone or in admixture.

$$N(X)_n(Y)_{3-n} \quad (B)\text{-}1$$

In the formula, n is equal to 1, 2 or 3; side chain Y is independently hydrogen or a straight, branched or cyclic $C_1$-$C_{20}$ alkyl group which may contain an ether or hydroxyl group; and side chain X is independently selected from groups of the following general formulas (X1) to (X3), and two or three X's may bond together to form a ring.

(X1)

(X2)

(X3)

In the formulas, $R^{300}$, $R^{302}$ and $R_{305}$ are independently straight or branched $C_1$-$C_4$ alkylene groups; $R^{301}$ and $R^{304}$ are independently hydrogen, straight, branched or cyclic $C_1$-$C_{20}$ alkyl groups, which may contain one or more hydroxyl, ether, ester group or lactone ring; $R^{303}$ is a single bond or a straight or branched $C_1$-$C_4$ alkylene group; and $R^{306}$ is a straight, branched or cyclic $C_1$-$C_{20}$ alkyl group, which may contain one or more hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris (2-formyloxyethyl)amine, tris(2-acetoxyethyl)amine, tris(2-propionyloxyethyl)amine, tris(2-butyryloxyethyl)amine, tris (2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2- oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl) ethylamine, N,N-bis(2-acetoxyethyl)-2-(tetrahydrofurfuryloxycarbonyl)ethylamine, N,N-bis(2-hydroxyethyl)-2-[(2-oxotetrahydrofuran-3-yl)oxy-carbonyl] ethylamine, N,N-bis(2-acetoxyethyl)-2-[(2-oxotetrahydrofuran-3-yl)oxy-carbonyl]ethylamine, N,N-bis (2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis [2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl) amine, tris(ethoxycarbonylmethyl)amine, N-butyl-bis (methoxycarbonylmethyl)amine, N-hexyl-bis (methoxycarbonylmethyl)amine, and β-(diethylamino)-δ-valerolactone.

Also useful are one or more organic nitrogen-containing compounds having cyclic structure represented by the following general formula (B)-2.

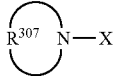

(B)-2

Herein X is as defined above, and $R^{307}$ is a straight or branched $C_2$-$C_{20}$ alkylene group which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy) ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy) ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

(B)-3

(B)-4

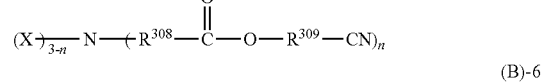

(B)-5

(B)-6

Herein, X, $R^{307}$ and n are as defined above, and $R^{308}$ and $R^{309}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy) ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds of imidazole structure having a polar functional group, represented by the general formula (B)-7.

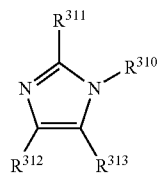

(B)-7

Herein, $R^{310}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic $C_1$-$C_{10}$ alkyl group, aryl group or aralkyl group.

Also included are organic nitrogen-containing compounds of benzimidazole structure having a polar functional group, represented by the general formula (B)-8.

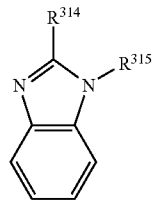

(B)-8

Herein, $R^{314}$ is a hydrogen atom, a straight, branched or cyclic $C_1$-$C_{10}$ alkyl group, aryl group or aralkyl group. $R^{315}$ is a polar functional group-bearing, straight, branched or cyclic $C_1$-$C_{20}$ alkyl group, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

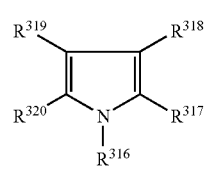

(B)-9

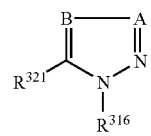

(B)-10

Herein, A is a nitrogen atom or =C—$R^{322}$, B is a nitrogen atom or =C—$R^{323}$, $R^{316}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic $C_1$-$C_{10}$ alkyl group or aryl group, or a pair of $R^{317}$ and $R^{318}$ and a pair of $R^{319}$ and $R^{320}$ may bond together to form a benzene, naphthalene or pyridine ring with the carbon atom to which they are attached; $R^{321}$ is a hydrogen atom, a straight, branched or cyclic $C_1$-$C_{10}$ alkyl group or aryl group; $R^{322}$ and $R^{323}$ each are a hydrogen atom, a straight, branched or cyclic $C_1$-$C_{10}$ alkyl group or aryl group, or a pair of $R^{321}$ and $R^{323}$ may bond together to form a benzene or naphthalene ring with the carbon atom to which they are attached.

Also included are organic nitrogen-containing compounds of aromatic carboxylic ester structure having the general formulae (B)-11 to (B)-14.

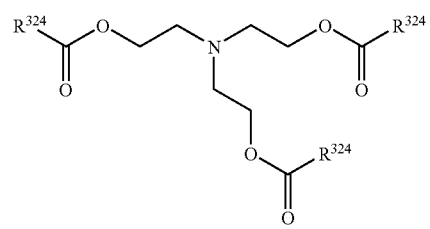

(B)-11

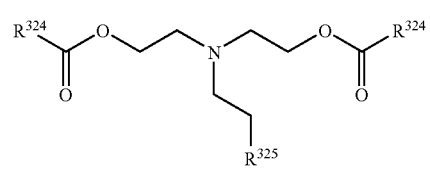

(B)-12

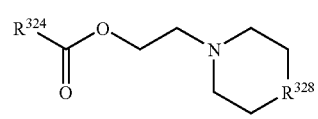

(B)-13

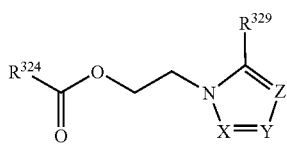

(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —$O(CH_2CH_2O)_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring with the carbon atom to which they are attached.

Further included are organic nitrogen-containing compounds of 7-oxanorbornane-2-carboxylic ester structure having the general formula (B)-15.

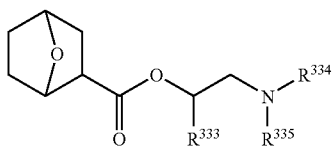

(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms with the nitrogen atom to which they are attached.

The organic nitrogen-containing compounds may be used alone or in admixture of two or more. The organic nitrogen-containing compound is preferably formulated in an amount of 0.001 to 4 parts, and especially 0.01 to 2 parts by weight, per 100 parts by weight of the entire base resin. Less than 0.001 part of the nitrogen-containing compound achieves no or little addition effect whereas more than 4 parts would result in too low a sensitivity.

Surfactant

Optionally, the resist composition of the invention may further comprise (E) a surfactant which is commonly used for facilitating the coating operation. The surfactant may be added in conventional amounts so long as this does not compromise the objects of the invention.

Illustrative, non-limiting examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (JEMCO Inc.), Megaface F171, F172, F173, R08, R30, R90 and R94 (DIC Corp.), Fluorad FC-430, FC-431, FC-4430 and FC-4432 (Sumitomo 3M Co., Ltd.), Asahiguard AG710, Surflon S-381, S-382, S-386, SC101, SC102, SC103, SC104, SC105, SC106, KH-10, KH-20, KH-30 and KH-40 (Asahi Glass Co., Ltd.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo Co., Ltd.). Additional useful surfactants include partially fluorinated oxetane ring-opened polymers having the structural formula (surf-1).

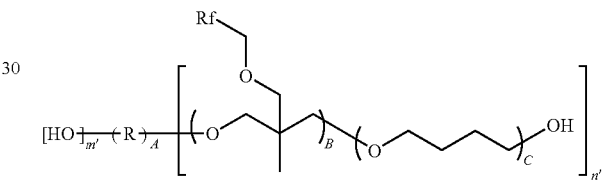

(surf-1)

It is provided herein that R, Rf, A, B, C, m', and n' are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

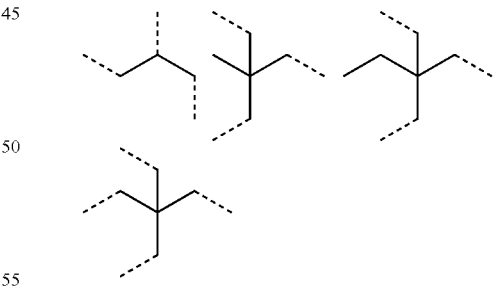

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m' is an integer of 0 to 3, n' is an integer of 1 to 4, and the sum of m' and n', which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either in blocks or randomly. For the preparation of surfactants in the form of partially fluorinated oxetane ring-opened polymers, reference should be made to U.S. Pat. No. 5,650,483, for example.

Of the foregoing surfactants, FC-4430, Surflon S-381, KH-20, KH-30, and oxetane ring-opened polymers of formula (surf-1) are preferred. These surfactants may be used alone or in admixture.

In the resist composition, the surfactant is preferably compounded in an amount of up to 2 parts, and especially up to 1 part by weight, per 100 parts by weight of the base resin. The amount of the surfactant, if added, is preferably at least 0.01 phr.

In the resist composition, an additive polymer may be added as another optional ingredient. This additive polymer tends to segregate in the sub-surface region of the resist film and has the functions of tailoring the hydrophilic/hydrophobic balance of the surface, enhancing water repellency, and/or preventing low-molecular-weight fractions from flowing into or out of the resist film when the resist film is in contact with water or another liquid. Such a segregating polymer may be added in conventional amounts as long as the objects of the invention are not compromised.

The segregating polymer is preferably selected from homopolymers and copolymers comprising fluorine-containing units of one or more types, and copolymers comprising fluorine-containing units and other units. Exemplary fluorine-containing units and other units are illustrated below, but not limited thereto.

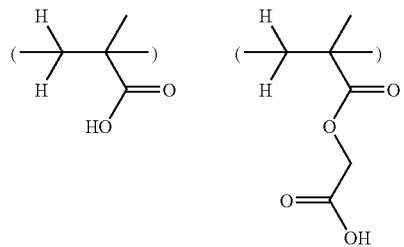

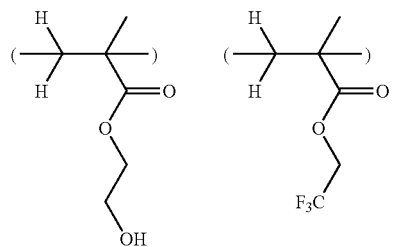

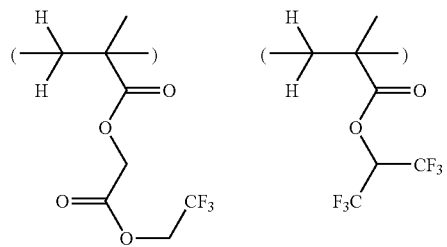

-continued

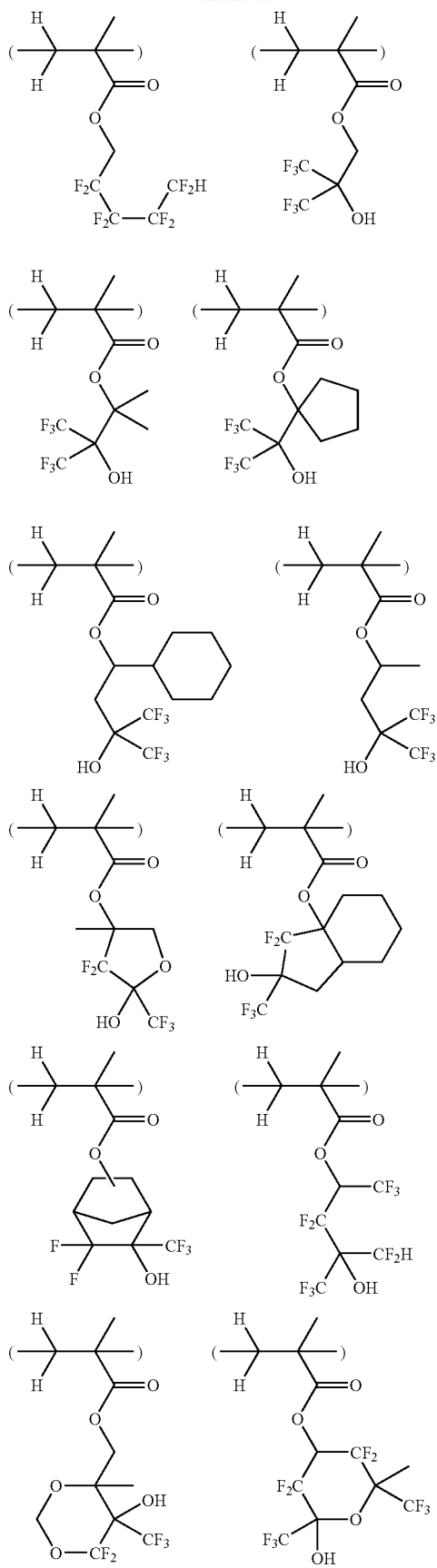

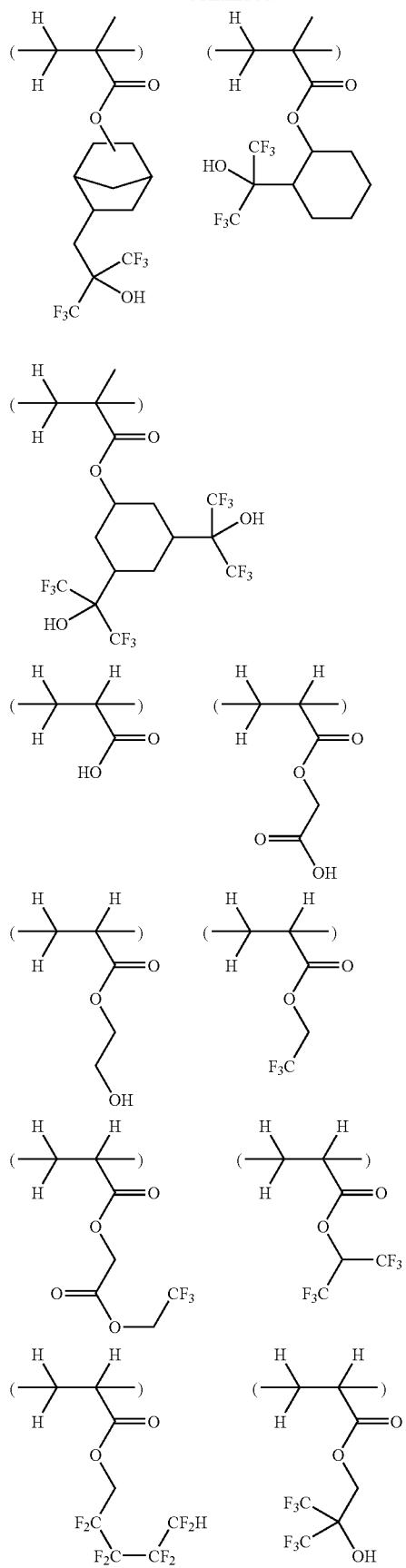
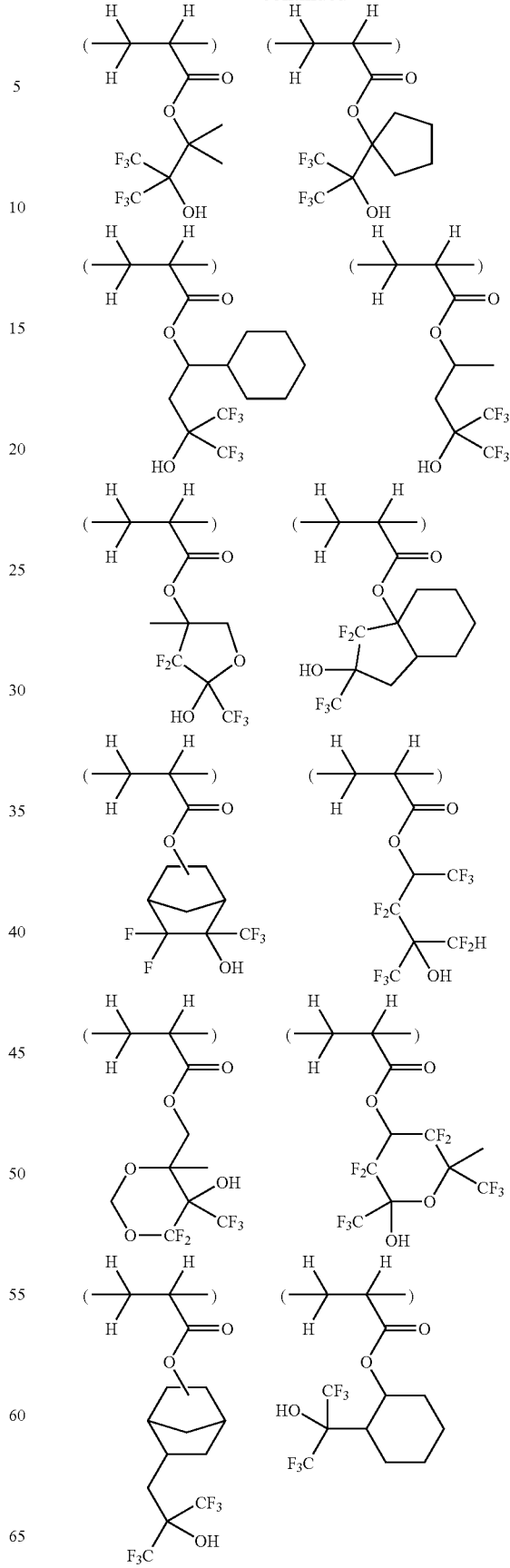

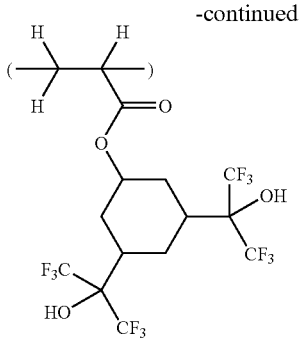

Preferably the segregating polymer has a weight average molecular weight of 1,000 to 50,000, and more preferably 2,000 to 20,000, as measured by GPC versus polystyrene standards. Outside the range, the surface modifying effect may be insufficient or development defects may form.

In the resist composition, the segregating polymer is preferably compounded in an amount of 0 to 10 parts, and especially 0 to 5 parts by weight, per 100 parts by weight of the base resin. The amount of the segregating polymer, if added, is preferably at least 1 phr.

While the resist composition of the invention typically comprises a base resin comprising the polymer, an acid generator, an organic solvent and an organic nitrogen-containing compound as described above, there may be added optional other ingredients such as dissolution regulators, carboxylic acids, and acetylene alcohol derivatives. Optional ingredients may be added in conventional amounts so long as this does not compromise the objects of the invention.

Dissolution Regulator

To the resist composition, a dissolution regulator may be added. The dissolution regulator is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 50 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

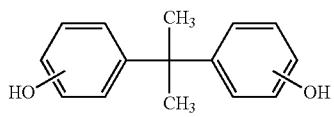
(D1)

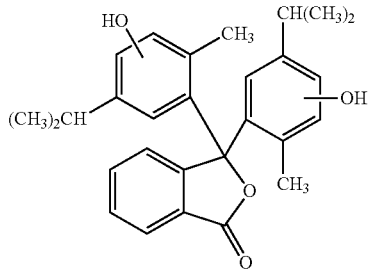
(D2)

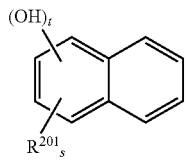
(D3)

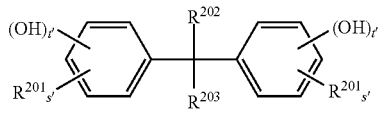
(D4)

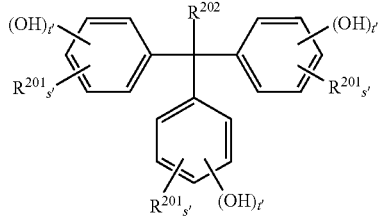
(D5)

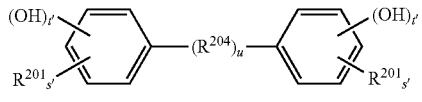
(D6)

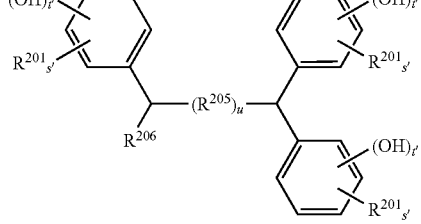
(D7)

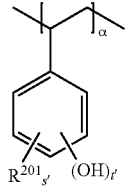
(D8)

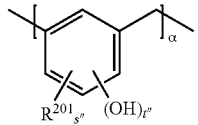
(D9)

-continued

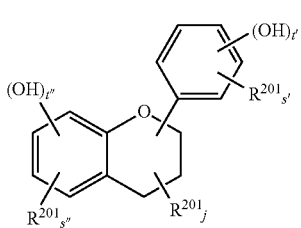
(D10)

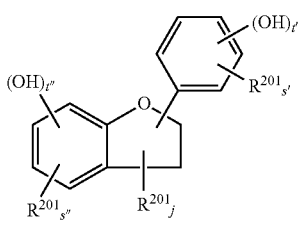
(D11)

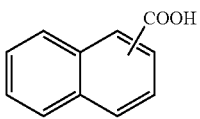
(D12)

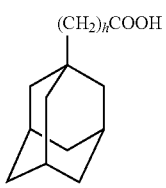
(D13)

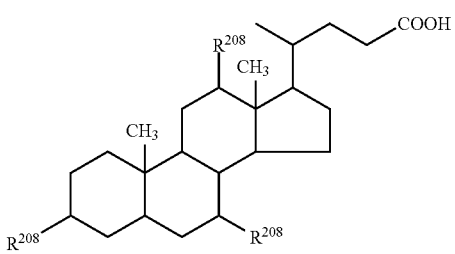
(D14)

In these formulas, $R^{202}$ and $R^{202}$ are each hydrogen or a straight or branched $C_1$-$C_8$ alkyl or alkenyl, for example, hydrogen, methyl, ethyl, butyl, propyl, ethynyl, and cyclohexyl. $R^{203}$ is hydrogen, a straight or branched $C_1$-$C_8$ alkyl or alkenyl, or —$(R^{207})_h$—COOH wherein $R^{207}$ is a straight or branched $C_1$-$C_{10}$ alkylene, for example, the same groups as exemplified for $R^{201}$ and $R^{202}$, and —COOH and —CH$_2$COOH. $R^{204}$ is —(CH$_2$)$_i$— (where i=2 to 10), a $C_6$-$C_{10}$ arylene, carbonyl, sulfonyl, an oxygen atom, or a sulfur atom, for example, ethylene, phenylene, carbonyl, sulfonyl, oxygen, and sulfur. $R^{205}$ is a $C_1$-$C_{10}$ alkylene, a $C_6$-$C_{10}$ arylene, carbonyl, sulfonyl, an oxygen atom, or a sulfur atom, for example, methylene and the same groups as exemplified for $R^{204}$. $R^{206}$ is hydrogen, a straight or branched $C_1$-$C_8$ alkyl or alkenyl, or a hydroxyl-substituted phenyl or naphthyl, for example, hydrogen, methyl, ethyl, butyl, propyl, ethynyl, cyclohexyl, and hydroxyl-substituted phenyl or naphthyl. $R^{208}$ is hydrogen or hydroxyl. The letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and α is a number such that the compounds of formula (D8) or (D9) have a weight average molecular weight of from 100 to 1,000.

The acid labile groups on the dissolution regulator may be selected from a variety of such groups and include groups of the general formulae (L1) to (L4) shown above, tertiary $C_4$-$C_{20}$ alkyl groups, trialkylsilyl groups in which each of the alkyls has 1 to 6 carbon atoms, and oxoalkyl groups of 4 to 20 carbon atoms. Examples of these groups are the same as described above.

The dissolution regulator may be formulated in an amount of 0 to 50 parts, preferably 0 to 40 parts, and more preferably 0 to 30 parts by weight, per 100 parts by weight of the base resin, and may be used singly or as a mixture of two or more thereof. More than 50 phr of the dissolution regulator would lead to slimming of the patterned film, and thus a decline in resolution.

The dissolution regulator can be synthesized by introducing acid labile groups into a compound having phenolic hydroxyl or carboxyl groups in accordance with an organic chemical formulation.

To the resist composition, a carboxylic acid compound may be added if necessary. The carboxylic acid compound which can be added to the resist composition is at least one compound selected from Groups I and II below, but not limited thereto. Inclusion of this compound improves the post-exposure delay (PED) stability of the resist and ameliorates edge roughness on nitride film substrates.

Group I:

Compounds of general formulas (A1) to (A10) below in which some or all of the hydrogen atoms on the phenolic hydroxyl groups are replaced by —$R^{401}$—COOH (wherein $R^{401}$ is a straight or branched $C_1$-$C_{10}$ alkylene group) and in which the molar ratio C/(C+D) of phenolic hydroxyl groups [C] to =C—C—COOH groups [D] in the molecule is from 0.1 to 1.0.

Group II:

Compounds of general formulas (A11) to (A15) below.

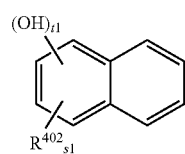
(A1)

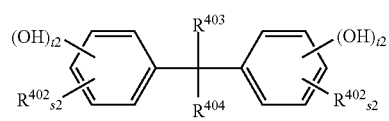
(A2)

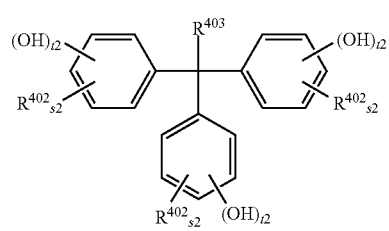
(A3)

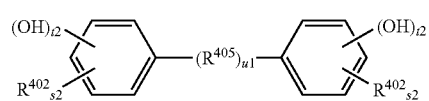
(A4)

-continued (A5) 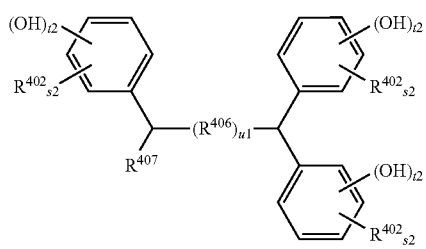

(A6) 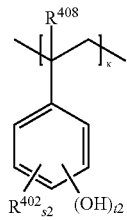

(A7) 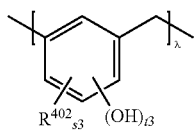

(A8) 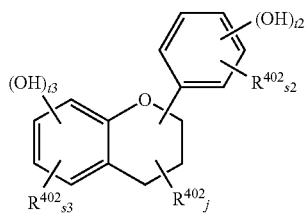

(A9) 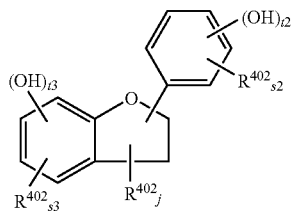

(A10) 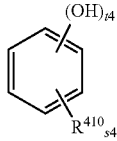

(A11) 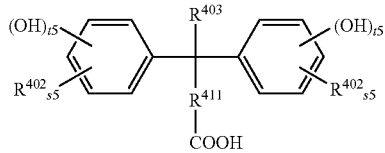

(A12) 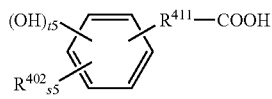

(A13) 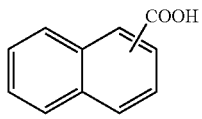

-continued (A14) 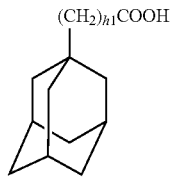

(A15) 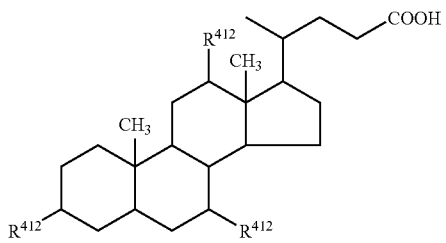

In these formulas, $R^{402}$ and $R^{403}$ are each hydrogen or a straight or branched $C_1$-$C_8$ alkyl or alkenyl; $R^{404}$ is hydrogen, a straight or branched $C_1$-$C_8$ alkyl or alkenyl, or a —$(R^{409})_h$—COOR' group (R' being hydrogen or —$R^{408}$—COOH); $R^{405}$ is —$(CH_2)_i$— (wherein i is 2 to 10), a $C_6$-$C_{10}$ arylene, carbonyl, sulfonyl, an oxygen atom, or a sulfur atom; $R^{406}$ is a $C_1$-$C_{10}$ alkylene, a $C_6$-$C_{10}$ arylene, carbonyl, sulfonyl, an oxygen atom, or a sulfur atom; $R^{407}$ is hydrogen, a straight or branched $C_1$-$C_8$ alkyl or alkenyl, or a hydroxyl-substituted phenyl or naphthyl; $R^{408}$ is hydrogen or methyl; $R^{409}$ is a straight or branched $C_1$-$C_{10}$ alkylene; $R^{410}$ is hydrogen, a straight or branched $C_1$-$C_8$ alkyl or alkenyl, or a —$R^{411}$—COOH group; $R^{411}$ is a straight or branched $C_1$-$C_{10}$ alkylene; $R^{412}$ is hydrogen or hydroxyl; the letter j is an integer from 0 to 3; s1, t1, s2, t2, s3, t3, s4, and t4 are each integers which satisfy s1+t1=8, s2+t2=5, s3+t3=4, and s4+t4=6, and are such that each phenyl structure has at least one hydroxyl group; s5 and t5 are numbers which satisfy s5≧0, t5≧0, and s5+t5=5; u1 is a number 1≦u1≦4; h1 is a number 0≦h1≦4; κ is a number such that the compound of formula (A6) may have a weight average molecular weight of 1,000 to 5,000; and λ is a number such that the compound of formula (A7) may have a weight average molecular weight of 1,000 to 10,000.

Illustrative, non-limiting examples of the compound having a carboxyl group include compounds of the general formulas AI-1 to AI-14 and AII-1 to AII-10 below.

(AI-1) 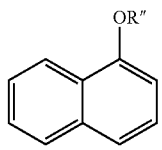

(AI-2) 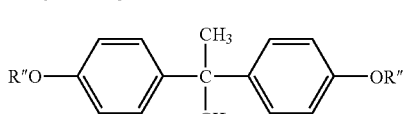

(AI-3) 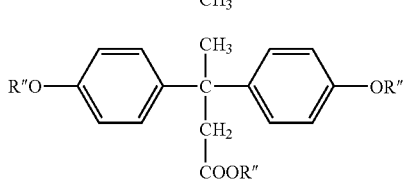

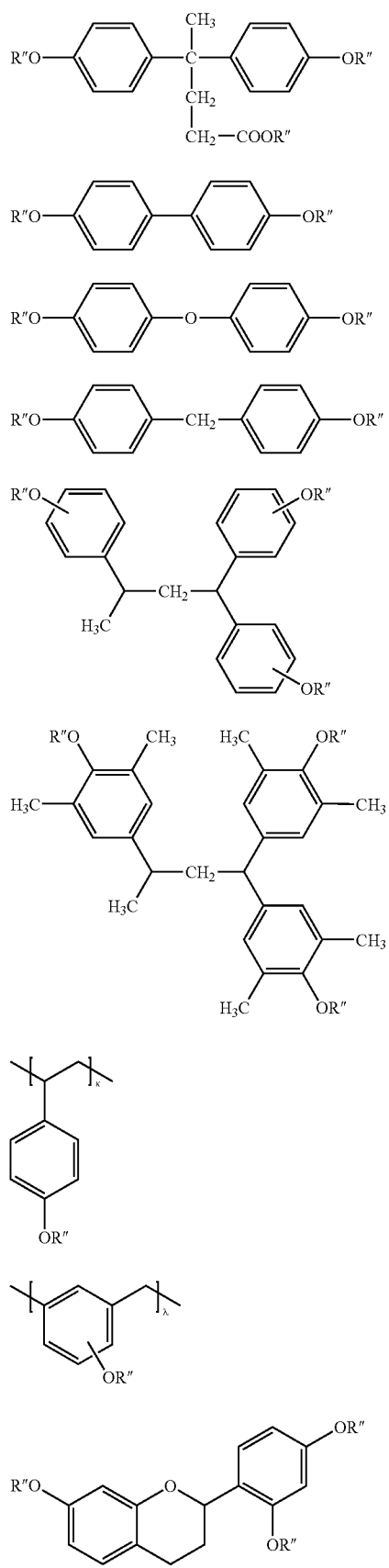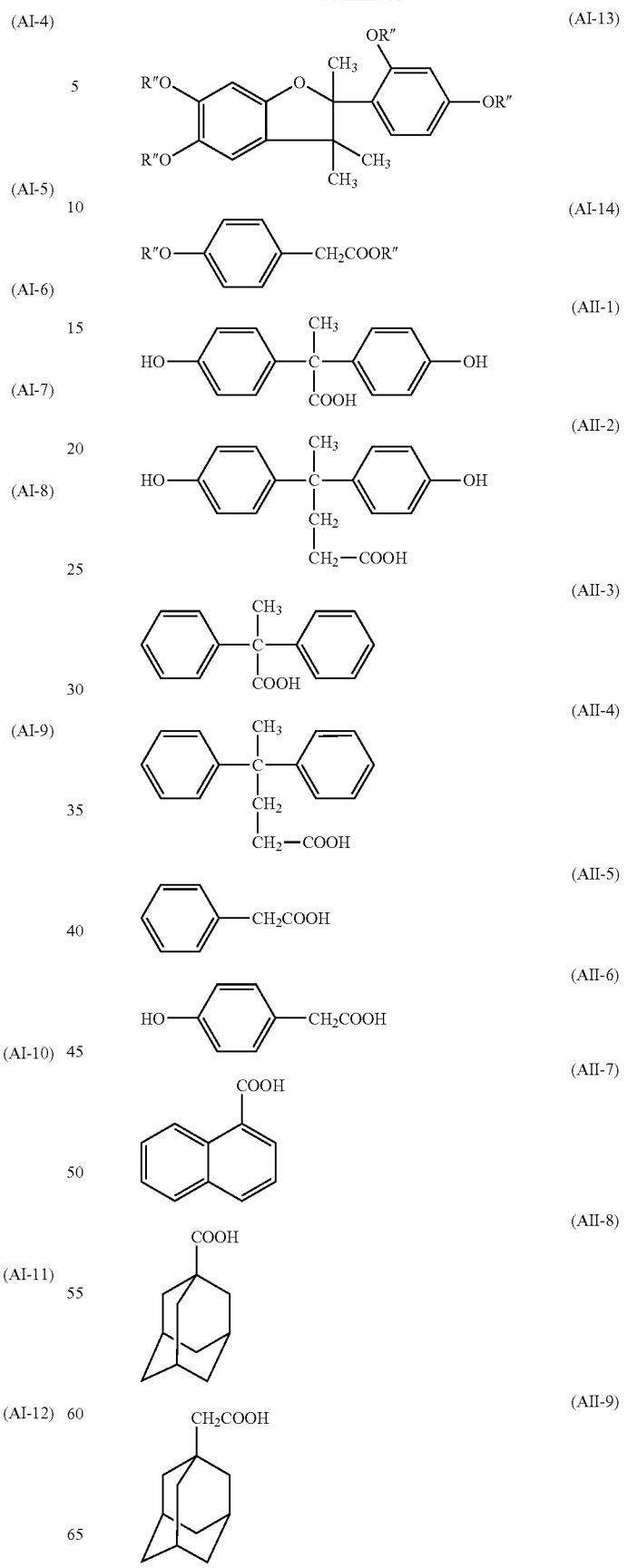

-continued

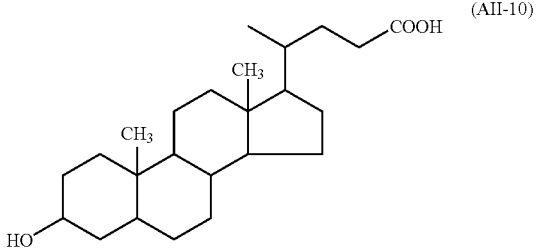
(AII-10)

In the above formulas, R'' is hydrogen or a —CH$_2$COOH group such that the —CH$_2$COOH group accounts for 10 to 100 mol % of R'' in each compound, κ and λ are as defined above.

The compound having a ≡C—COOH group may be used singly or as combinations of two or more thereof. The compound having a ≡C—COOH group is added in an amount ranging from 0 to 5 parts, preferably 0.1 to 5 parts, more preferably 0.1 to 3 parts, further preferably 0.1 to 2 parts by weight, per 100 parts by weight of the base resin. More than 5 phr of the compound may reduce the resolution of the resist composition.

To the resist composition, an acetylene alcohol derivative may be added. The preferred acetylene alcohol derivatives used herein include those having the general formulae (S1) and (S2).

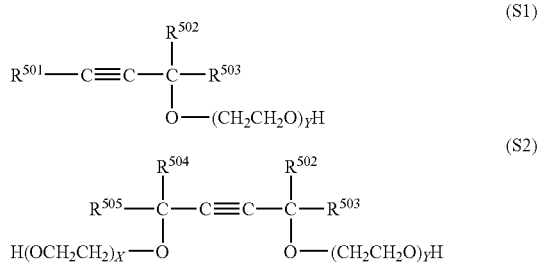

In the formulas, $R^{501}$, $R^{502}$, $R^{503}$, $R^{504}$, and $R^{505}$ are each hydrogen or a straight, branched or cyclic $C_1$-$C_8$ alkyl; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industries Ltd.

The acetylene alcohol derivative is preferably added in an amount of 0 to 2 parts, more preferably 0.01 to 2 parts, and even more preferably 0.02 to 1 part by weight per 100 parts by weight of the base resin. More than 2 phr of the derivative may reduce the resolution of the resist composition.

Process

Pattern formation using the resist composition of the invention may be performed by well-known lithography processes. The process generally involves coating, heat treatment (or prebaking), exposure, heat treatment (post-exposure baking, PEB), and development. If necessary, any additional steps may be added.

For pattern formation, the resist composition is first applied onto a substrate (on which an integrated circuit is to be formed, e.g., Si, SiO$_2$, SiN, SiON, TiN, WSi, BPSG, SOG, organic antireflective coating, Cr, CrO, CrON, MoSi, etc.) by a suitable coating technique such as spin coating, roll coating, flow coating, dip coating, spray coating or doctor coating. The coating is prebaked on a hot plate at a temperature of 60 to 150° C. for 1 to 10 minutes, preferably 80 to 140° C. for 1 to 5 minutes. The resulting resist film is generally 0.01 to 2.0 μm thick.

A relationship of a reduced thickness of resist film to an etch selectivity ratio between resist film and processable substrate imposes severer limits on the process. Under consideration is the tri-layer process in which a resist layer, a silicon-containing intermediate layer, an undercoat layer having a high carbon density and high etch resistance, and a processable substrate are laminated in sequence from top to bottom. On etching with oxygen gas, hydrogen gas, ammonia gas or the like, a high etch selectivity ratio is available between the silicon-containing intermediate layer and the undercoat layer, which allows for thickness reduction of the silicon-containing intermediate layer. A relatively high etch selectivity ratio is also available between the monolayer resist and the silicon-containing intermediate layer, which allows for thickness reduction of the monolayer resist. The method for forming the undercoat layer in this case includes a coating and baking method and a CVD method. In the case of coating, novolac resins and resins obtained by polymerization of fused ring-containing olefins are used. In the CVD film formation, gases such as butane, ethane, propane, ethylene and acetylene are used. For the silicon-containing intermediate layer, either a coating method or a CVD method may be employed. The coating method uses silsesquioxane, polyhedral oligomeric silsesquioxane (POSS) and the like while the CVD method uses silane gases as the reactant. The silicon-containing intermediate layer may have an antireflection function with a light absorbing ability and have photo-absorptive groups like phenyl groups, or it may be a SiON film. An organic film may be formed between the silicon-containing intermediate layer and the photoresist, and the organic film in this case may be an organic antireflective coating. After the photoresist film is formed, deionized water rinsing (or post-soaking) may be carried out for extracting the photoacid generator and the like from the film surface or washing away particles, or a protective film may be coated.

With a mask having a desired pattern placed above the resist film, the resist film is then exposed to actinic radiation such as UV, deep-UV, electron beams, x-rays, excimer laser light, γ-rays and synchrotron radiation. The exposure dose is preferably about 1 to 200 mJ/cm$^2$, more preferably about 10 to 100 mJ/cm$^2$. The film is further baked on a hot plate at 60 to 150° C. for 1 to 5 minutes, preferably 80 to 120° C. for 1 to 3 minutes (post-exposure baking=PEB). Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate. It is appreciated that the resist composition of the invention is suited for micro-patterning using such high-energy radiation as deep UV with a wavelength of 254 to 193 nm, vacuum UV with a wavelength of 157 nm, electron beams, soft x-rays, x-rays, excimer laser light, γ-rays and synchrotron radiation, and best suited for micropatterning using high-energy radiation in the wavelength range of 180 to 200 nm.

Immersion lithography can be applied to the resist composition of the invention. The ArF immersion lithography uses a liquid having a refractive index of at least 1 and highly transparent at the exposure wavelength such as deionized water or alkanes as the immersion solvent. The immersion lithography involves prebaking a resist film and exposing the resist film to light through a projection lens, with deionized water or similar liquid interposed between the resist film and the projection lens. Since this allows projection lenses to be designed to a numerical aperture (NA) of 1.0 or higher, formation of finer patterns is possible. The immersion lithography is important for the ArF lithography to survive to the 45-nm node, with a further development thereof being accelerated. In the case of immersion lithography, deionized water rinsing (or post-soaking) may be carried out after exposure for removing water droplets left on the resist film, or a protective coating may be applied onto the resist film after pre-baking for preventing any dissolution from the resist and improving water slip on the film surface.

The resist protective coating used in the immersion lithography is preferably formed from a solution of a polymer having 1,1,1,3,3,3-hexafluoro-2-propanol residue which is insoluble in water, but dissolvable in an alkaline developer liquid, in a solvent selected from alcohols of at least 4 carbon atoms, ethers of 8 to 12 carbon atoms, and mixtures thereof.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

EXAMPLE

Examples of the invention are given below by way of illustration and not by way of limitation. Mw is a weight average molecular weight as measured by gel permeation chromatography (GPC) versus polystyrene standards.

Example 1

Acetal compounds within the scope of the invention were synthesized in accordance with the formulation shown below.

Example 1-1

Synthesis of Monomer 1

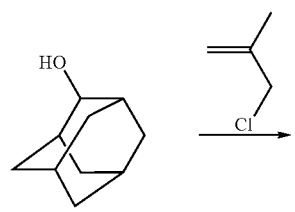

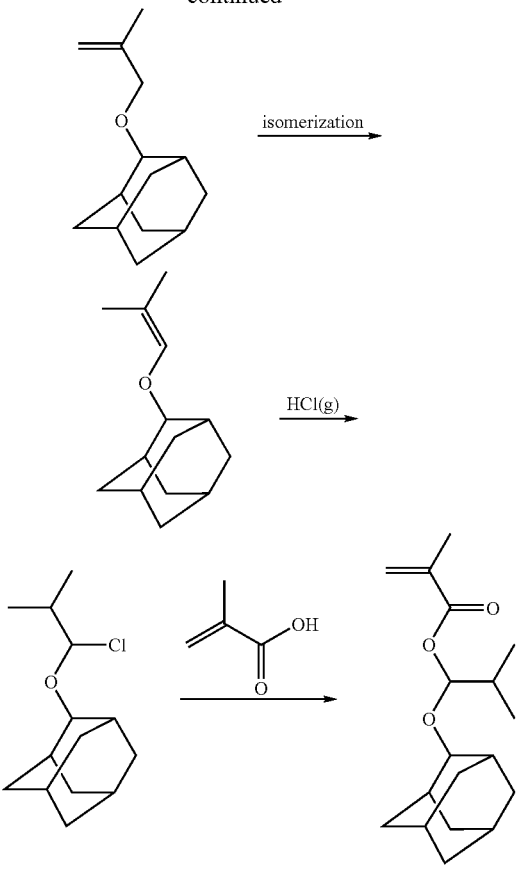

Example 1-1-1

Synthesis of 2-adamantyl-2-methyl-2-propenyl ether

In 700 ml of tetrahydrofuran was dispersed 111.6 g of 60% sodium hydride. A mixture of 404.5 g of 2-adamantanol and 700 ml of tetrahydrofuran was added dropwise to the dispersion below 50° C. The contents were stirred at 50° C. for 4 hours to form sodium alkoxide. 19.9 g of sodium iodide was added, 336.8 g of β-methacrylic chloride then added below 60° C., and stirring continued at 60° C. for 8 hours. 500 ml of water was added to quench the reaction, followed by standard work-up. Purification by distillation gave 537 g (yield 98%) of the end compound.

Boiling point: 72° C./29 Pa
IR (NaCl): ν=3074, 2904, 2852, 2672, 1652, 1450, 1361, 1106, 1079, 1043, 896 cm$^{-1}$
$^1$H-NMR (600 MHz in CDCl$_3$): δ=1.46 (2H, app d), 1.63 (2H, d), 1.69 (2H, s), 1.75 (3H, s), 1.76-1.85 (4H, m), 2.01 (2H, app s), 2.07 (2H, d), 3.43 (1H, t), 3.88 (2H, s), 4.85 (1H, m), 4.99 (1H, m) ppm Example 1-1-2

Synthesis of 2-adamantyl-2-methyl-1-propenyl ether 539.8 g of 2-adamantyl-2-methyl-2-propenyl ether which was prepared in Example 1-1-1 was mixed with 27.0 g of potassium tert-butoxide and 432 g of dimethyl sulfoxide. The mixture was stirred at 60° C. for 3 hours, and 400 ml of water was added, followed by standard work-up. Purification by distillation gave 530 g (yield 98%) of the end compound.

Boiling point: 76° C./30 Pa

IR (NaCl): ν=2906, 2852, 1689, 1467, 1450, 1382, 1332, 1272, 1182, 1160, 1101, 1085, 1054, 1012, 962, 936 cm$^{-1}$ $^1$H-NMR (600 MHz in CDCl$_3$): δ=1.48 (2H, app d), 1.54 (3H, app d), 1.63-1.68 (5H, m), 1.71 (2H, s), 1.78-1.86 (4H, m), 1.98 (2H, app s), 2.07 (2H, d), 3.68 (1H, t), 5.81 (1H, m) ppm Example 1-1-3

Synthesis of 1-(2-adamantyloxy)-2-methylpropyl methacrylate

Under ice cooling, hydrogen chloride gas was introduced over the course of 30 minutes into a mixture of 104 g of 2-adamantyl-2-methyl-1-propenyl ether which was prepared in Example 1-1-2 and 1,000 g of hexane. After the interruption of hydrogen chloride gas, nitrogen gas was introduced for 2 hours under ice cooling to remove residual hydrogen chloride in the system, yielding 2-adamantyl-1-chloro-2-methylpropyl ether, precursor to Monomer 1. Subsequently, 86.1 g of methacrylic acid, 111 g of triethylamine, and 0.1 g of 2,2'-methylenebis(6-t-butyl-p-cresol) were added to the reaction system, followed by stirring at room temperature for 4 hours. Thereafter, 1,000 g of water was added to quench the reaction, and the organic layer recovered. The organic layer was sequentially washed with water, sodium hydrogen carbonate water, and saturated brine, and concentrated. Purification by distillation gave 126 g (yield 86%) of the target compound.

Boiling point: 98-100° C./15 Pa

IR (NaCl): ν=2964, 2906, 2854, 1716, 1637, 1471, 1450, 1382, 1365, 1319, 1295, 1176, 1143, 1099, 1006, 985, 962, 937, 908, 898 cm$^{-1}$ $^1$H-NMR (600 MHz in DMSO-d$_6$): δ=0.89 (3H, d), 0.92 (3H, d), 1.41-1.47 (2H, m), 1.56-1.59 (2H, m), 1.65 (1H, app s), 1.72-1.76 (3H, m), 1.78-1.81 (2H, m), 1.87 (3H, t), 1.88-2.00 (3H, m), 3.64 (1H, t), 5.68-5.70 (1H, m), 5.74 (1H, d), 6.04 (1H, app d) ppm $^{13}$C-NMR (150 MHz in DMSO-d$_6$): δ=16.49, 16.89, 17.85, 26.46, 26.69, 30.74, 30.90, 31.05, 32.46, 32.72, 35.67, 35.93, 36.00, 36.83, 79.90, 99.68, 125.93, 135.87, 166.30 ppm Example 1-2

Synthesis of Monomer 2

By following the same procedures as in Examples 1-1-1 to 1-1-3 aside from using acrylic acid instead of methacrylic acid, 1-(2-adamantyloxy)-2-methylpropyl acrylate was produced (four step yield 77%).

Example 1-3

Synthesis of Monomer 3

By following the same procedures as in Examples 1-1-1 to 1-1-3 aside from using 2-(trifluoromethyl)acrylic acid instead of methacrylic acid, 1-(2-adamantyloxy)-2-methylpropyl 2-(trifluoromethyl)acrylate was produced (four step yield 66%).

Example 1-4

Synthesis of Monomer 4

Example 1-4-1

Synthesis of (1-adamantyl)methyl-2-methyl-2-propenyl ether

The end compound was produced by the same procedure as in Example 1-1-1 aside from using 1-adamantanemethanol instead of 2-adamantanol. Yield 97%.

Boiling point: 75° C./26 Pa

IR (NaCl): ν=3074, 2971, 2902, 2848, 2678, 2658, 1656, 1450, 1371, 1362, 1348, 1316, 1291, 1249, 1188, 1156, 1092, 1057, 1014, 997, 937, 897, 813 cm$^{-1}$ $^1$H-NMR (600 MHz in CDCl$_3$): δ=1.54-1.55 (6H, m), 1.63-1.66 (3H, m), 1.70-1.72 (6H, m), 1.95 (3H, m), 2.94 (2H, s), 3.83 (2H, s), 4.85 (1H, d), 4.93 (1H, m) ppm $^{13}$C-NMR (150 MHz in CDCl$_3$): δ=19.33, 28.31, 33.96, 37.24, 39.76, 75.21, 80.99, 111.45, 142.83 ppm GC-MS (EI): (m/z)$^+$=29, 41, 55, 67, 79, 93, 107, 121, 135, 149, 165, 177, 189, 202, 220 (M$^+$)

Example 1-4-2

Synthesis of (1-adamantyl)methyl-2-methyl-1-propenyl ether

The end compound was produced by the same procedure as in Example 1-1-2 aside from using (1-adamantyl)methyl-2-methyl-2-propenyl ether instead of 2-adamantyl-2-methyl-2-propenyl ether. Yield 97%.

Boiling point: 74° C./24 Pa

IR (NaCl): ν=2903, 2849, 2735, 2675, 1692, 1452, 1373, 1344, 1317, 1291, 1261, 1225, 1192, 1165, 1107, 1049, 1025, 988, 824 cm$^{-1}$ $^1$H-NMR (600 MHz in CDCl$_3$): δ=1.51-1.52 (3H, m), 1.54-1.53 (6H, m), 1.61 (3H, m), 1.63-1.66 (3H, m), 1.70-1.72 (3H, m), 1.96 (3H, m), 5.77 (1H, m) ppm $^{13}$C-NMR (150 MHz in CDCl$_3$): δ=14.93, 19.42, 28.21, 34.29, 37.19, 39.47, 82.64, 109.08, 141.42 ppm GC-MS (EI): (m/z)$^+$=29, 41, 55, 67, 79, 93, 107, 121, 135, 149, 165, 177, 189, 203, 220 (M$^+$)

Example 1-4-3

Synthesis of 1-[(1-adamantyl)methoxy]-2-methylpropyl methacrylate (Monomer 4)

The target compound was produced by the same procedure as in Example 1-1-3 aside from using (1-adamantyl)methyl-2-methyl-1-propenyl ether instead of 2-adamantyl-2-methyl-1-propenyl ether. Yield 91%.

Boiling point: 97-100° C./13 Pa

IR (NaCl): ν=2964, 2904, 2849, 1719, 1638, 1451, 1366, 1320, 1292, 1261, 1176, 1093, 1007, 990, 936, 908, 812 cm$^{-1}$ $^1$H-NMR (600 MHz in DMSO-d$_6$): δ=0.87 (3H, d), 0.90 (3H, d), 1.44-1.49 (6H, m), 1.57-1.59 (3H, m), 1.65-1.67 (3H, m), 1.90-1.91 (3H, m), 3.00 (1H, d), 3.13 (1H, d), 5.55 (1H, d), 5.70 (1H, m), 6.06 (1H, m) ppm $^{13}$C-NMR (150 MHz in DMSO-d$_6$): δ=16.58, 16.84, 17.86, 27.46, 32.19, 33.39, 36.57, 38.89, 79.17, 101.64, 126.04, 135.76, 166.34 ppm GC-MS (EI): (m/z)$^+$=25, 41, 69, 93, 121, 149, 177, 193, 220, 245, 263, 288, 306 (M$^+$)

Example 1-5

Synthesis of Monomer 5

By following the same procedures as in Examples 1-1-1 to 1-1-3 aside from using 1-adamantanemethanol instead of 2-adamantanol and acrylic acid instead of methacrylic acid, 1-[(1-adamantyl)methoxy]-2-methylpropyl acrylate was produced (four step yield 78%).

Example 1-6

Synthesis of Monomer 6

By following the same procedures as in Examples 1-1-1 to 1-1-3 aside from using 1-adamantanemethanol instead of 2-adamantanol and 2-(trifluoromethyl)acrylic acid instead of methacrylic acid, 1-[(1-adamantyl)methoxy]-2-methylpropyl 2-(trifluoromethyl)acrylate was produced (four step yield 67%).

Example 1-7

Synthesis of Monomer 7

Example 1-7-1

Synthesis of 1-adamantyl-2-methyl-2-propenyl ether

The end compound was produced by the same procedure as in Example 1-1-1 aside from using 1-adamantanol instead of 2-adamantanol. Yield 96%.

Boiling point: 68° C./16 Pa

IR (NaCl): ν=3074, 2908, 2852, 1654, 1452, 1369, 1353, 1315, 1305, 1184, 1120, 1105, 1089, 1049, 894 cm$^{-1}$ $^1$H-NMR (600 MHz in CDCl$_3$): δ=1.58-1.65 (6H, m), 1.72 (3H, s), 1.76 (6H, app d), 2.13 (2H, s), 3.84 (2H, s), 4.82 (1H, m), 4.98 (1H, m) ppm

Example 1-7-2

Synthesis of 1-adamantyl-2-methyl-1-propenyl ether

The end compound was produced by the same procedure as in Example 1-1-2 aside from using 1-adamantyl-2-methyl-2-propenyl ether instead of 2-adamantyl-2-methyl-2-propenyl ether. Yield 97%.

Boiling point: 72° C./25 Pa

IR (NaCl): ν=2908, 2852, 1685, 1452, 1378, 1367, 1353, 1317, 1305, 1272, 1186, 1153, 1103, 1076, 973, 937, 919 cm$^{-1}$ $^1$H-NMR (600 MHz in CDCl$_3$): δ=1.55 (3H, m), 1.57-1.66 (9H, m), 1.77 (6H, d), 2.14 (3H, s), 6.07 (1H, sept) ppm

Example 1-7-3

Synthesis of 1-(1-adamantyloxy)-2-methylpropyl methacrylate Monomer 7)

The target compound was produced by the same procedure as in Example 1-1-3 aside from using 1-adamantyl-2-methyl-1-propenyl ether instead of 2-adamantyl-2-methyl-1-propenyl ether. Yield 91%.

Boiling point: 106° C./11 Pa

IR (NaCl): ν=2963, 2909, 2853, 1712, 1637, 1471, 1453, 1394, 1365, 1355, 1321, 1295, 1177, 1141, 1104, 1083, 1005, 962, 936, 898, 858, 812, 667 cm$^{-1}$ $^1$H-NMR (600 MHz in DMSO-d$_6$): δ=0.81 (3H, d), 0.86 (3H, d), 1.51-1.61 (9H, m), 1.71-1.73 (3H, m), 1.80 (1H, m), 1.86 (3H, s), 2.07 (3H, s), 5.66-5.67 (1H, m), 5.92 (1H, d), 6.01-6.02 (1H, m) ppm $^{13}$C-NMR (150 MHz in DMSO-d$_6$): δ=16.28, 17.05, 17.85, 29.87, 32.79, 35.55, 41.60, 73.79, 94.97, 125.71, 136.20, 165.74 ppm

Example 1-8

Synthesis of Monomer 8

By following the same procedures as in Examples 1-1-1 to 1-1-3 aside from using 1-adamantanol instead of 2-adamantanol and acrylic acid instead of methacrylic acid, 1-(1-adamantyloxy)-2-methylpropyl acrylate was produced (four step yield 74%).

Example 1-9

Synthesis of Monomer 9

By following the same procedures as in Examples 1-1-1 to 1-1-3 aside from using 1-adamantanol instead of 2-adamantanol and 2-(trifluoromethyl)acrylic acid instead of methacrylic acid, 1-(1-adamantyloxy)-2-methylpropyl 2-(trifluoromethyl)acrylate was produced (four step yield 63%).

Example 1-10

Synthesis of Monomer 10

By following the same procedures as in Examples 1-1-1 to 1-1-3 aside from using 2-adamantanemethanol instead of 2-adamantanol, 1-[(2-adamantyl)methoxy]-2-methylpropyl methacrylate was produced (four step yield 75%).

Example 1-11

Synthesis of Monomer 11

By following the same procedures as in Examples 1-1-1 to 1-1-3 aside from using 2-adamantylethanol instead of 2-adamantanol, 1-[(2-adamantyl)ethoxy]-2-methylpropyl methacrylate was produced (four step yield 76%).

Example 1-12

Synthesis of Monomer 12

By following the same procedures as in Examples 1-1-1 to 1-1-3 aside from using 1-adamantylethanol instead of 2-adamantanol, 1-[(1-adamantyl)ethoxy]-2-methylpropyl methacrylate was produced (four step yield 75%).

Polymers within the scope of the invention were synthesized in accordance with the formulation shown below.

Example 2-1

Synthesis of Polymer 1

In a nitrogen atmosphere, 28.3 g of 1-(2-adamantyloxy)-2-methylpropyl methacrylate (Monomer 1), 21.7 g of 4,8- dioxatricyclo[4.2.1.0$^{3,7}$]nonan-5-on-2-yl methacrylate, and 2.23 g of dimethyl 2,2'-azobisisobutyrate were dissolved in 80.0 g of methyl ethyl ketone. With stirring under a nitrogen atmosphere, the solution was added dropwise to 36.6 g of methyl ethyl ketone at 80° C. over 4 hours. After the completion of dropwise addition, the reaction solution was stirred at 80° C. for 2 hours and cooled to room temperature. The polymerization solution was added dropwise to 500 g of n-hexane. The thus precipitated solids were filtered and dried in vacuum at 50° C. for 16 hours, obtaining a polymer in white powder solid form, designated Polymer 1. The amount was 45.5 g, and the yield was 91%.

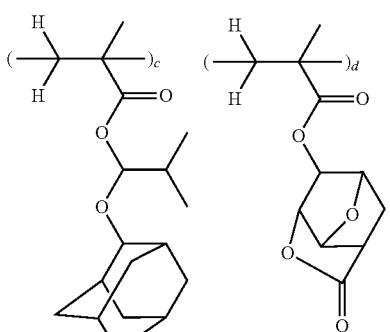

(c = 0.50, d = 0.50, Mw = 6,600)

Polymer 1

Examples 2-2 to 2-28, Comparative Examples 1-1 to 1-4

Polymers 2 to 32 were synthesized by the same procedure as Example 2-1 except that the type and proportion of monomers were changed, with their compositional proportion (in molar ratio) and Mw being shown in Table 1. The structure of the units is shown in Tables 2 to 5.

TABLE 1

| | | Resin | Unit 1 (ratio) | Unit 2 (ratio) | Unit 3 (ratio) | Unit 4 (ratio) | Mw |
|---|---|---|---|---|---|---|---|
| Example | 2-1 | Polymer 1 | Y-1M (0.50) | B-3M (0.50) | — | — | 6,600 |
| | 2-2 | Polymer 2 | Y-2M (0.50) | B-3M (0.50) | — | — | 6,800 |
| | 2-3 | Polymer 3 | Y-3M (0.50) | B-3M (0.50) | — | — | 6,500 |
| | 2-4 | Polymer 4 | Y-1M (0.30) | B-1M (0.25) | B-3M (0.45) | — | 6,500 |
| | 2-5 | Polymer 5 | Y-2M (0.30) | B-1M (0.25) | B-3M (0.45) | — | 6,600 |
| | 2-6 | Polymer 6 | Y-3M (0.30) | B-1M (0.25) | B-3M (0.45) | — | 6,300 |
| | 2-7 | Polymer 7 | Y-1M (0.30) | B-1M (0.25) | B-4M (0.45) | — | 6,600 |
| | 2-8 | Polymer 8 | Y-2M (0.30) | B-1M (0.25) | B-4M (0.45) | — | 6,800 |
| | 2-9 | Polymer 9 | Y-3M (0.30) | B-1M (0.25) | B-4M (0.45) | — | 6,500 |
| | 2-10 | Polymer 10 | Y-1M (0.30) | B-1M (0.25) | B-7M (0.45) | — | 6,200 |
| | 2-11 | Polymer 11 | Y-2M (0.30) | B-1M (0.25) | B-7M (0.45) | — | 6,300 |
| | 2-12 | Polymer 12 | Y-3M (0.30) | B-1M (0.25) | B-7M (0.45) | — | 6,000 |
| | 2-13 | Polymer 13 | Y-1M (0.30) | B-2M (0.25) | B-3M (0.45) | — | 6,500 |
| | 2-14 | Polymer 14 | Y-1M (0.30) | B-1M (0.25) | B-5M (0.45) | — | 6,400 |
| | 2-15 | Polymer 15 | Y-1M (0.30) | B-1M (0.25) | B-6M (0.45) | — | 6,100 |
| | 2-16 | Polymer 16 | Y-1M (0.30) | B-1M (0.25) | B-8M (0.45) | — | 7,200 |
| | 2-17 | Polymer 17 | Y-1M (0.30) | B-1M (0.25) | B-9M (0.45) | — | 7,400 |
| | 2-18 | Polymer 18 | Y-1M (0.30) | B-1M (0.25) | B-10M (0.45) | — | 7,000 |
| | 2-19 | Polymer 19 | Y-1M (0.25) | B-1M (0.25) | B-3M (0.40) | C-1M (0.10) | 6,000 |
| | 2-20 | Polymer 20 | Y-1M (0.25) | B-1M (0.25) | B-3M (0.40) | C-2M (0.10) | 7,100 |
| | 2-21 | Polymer 21 | Y-1M (0.25) | B-1M (0.25) | B-3M (0.40) | C-3M (0.10) | 7,300 |
| | 2-22 | Polymer 22 | Y-1M (0.25) | B-1M (0.25) | B-3M (0.40) | C-4M (0.10) | 7,100 |
| | 2-23 | Polymer 23 | Y-1M (0.20) | A-1M (0.10) | B-1M (0.25) | B-3M (0.45) | 6,600 |
| | 2-24 | Polymer 24 | Y-1M (0.20) | A-2M (0.10) | B-1M (0.25) | B-3M (0.45) | 6,300 |
| | 2-25 | Polymer 25 | Y-1M (0.20) | A-3M (0.10) | B-1M (0.25) | B-3M (0.45) | 6,500 |
| | 2-26 | Polymer 26 | Y-1M (0.20) | A-4M (0.10) | B-1M (0.25) | B-3M (0.45) | 6,200 |
| | 2-27 | Polymer 27 | Y-1M (0.20) | A-5M (0.10) | B-1M (0.25) | B-3M (0.45) | 6,400 |
| | 2-28 | Polymer 28 | Y-1M (0.20) | A-6M (0.10) | B-1M (0.25) | B-3M (0.45) | 6,600 |
| Comparative Example | 1-1 | Polymer 29 | — | A-1M (0.30) | B-1M (0.25) | B-3M (0.45) | 6,400 |
| | 1-2 | Polymer 30 | — | A-6M (0.30) | B-1M (0.25) | B-3M (0.45) | 6,600 |
| | 1-3 | Polymer 31 | — | A-7M (0.30) | B-1M (0.25) | B-3M (0.45) | 5,900 |
| | 1-4 | Polymer 32 | — | A-8M (0.30) | B-1M (0.25) | B-3M (0.45) | 6,400 |

TABLE 2

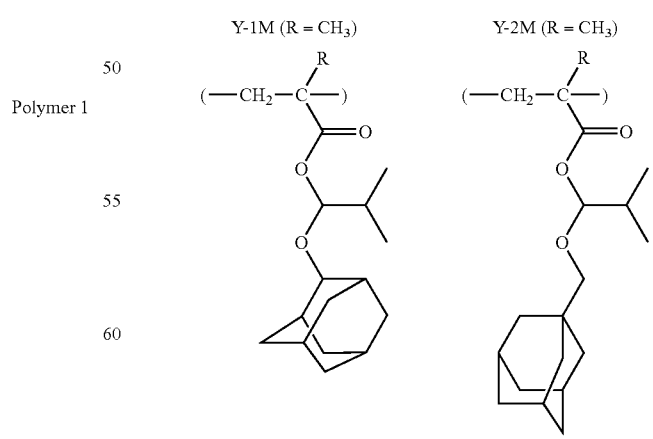

Y-1M (R = CH$_3$)  Y-2M (R = CH$_3$)

Y-3M (R = CH$_3$)

TABLE 2-continued
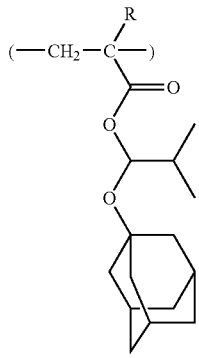
TABLE 3
A-1M (R = CH₃)     A-2M (R = CH₃)
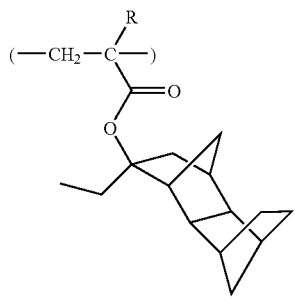
A-3M (R = CH₃)     A-4M (R = CH₃)
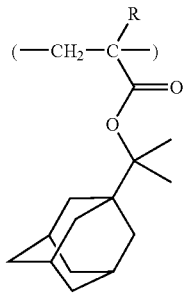     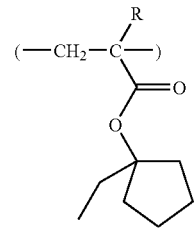
A-5M (R = CH₃)     A-6M (R = CH₃)
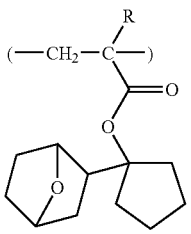     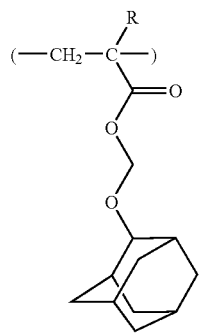
A-7M (R = CH₃)     A-8M (R = CH₃)
TABLE 3-continued
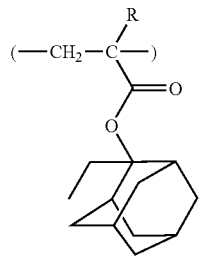
TABLE 4
B-1M (R = CH₃)     B-2M (R = CH₃)
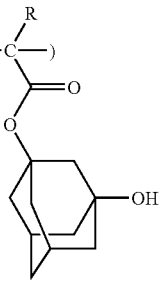     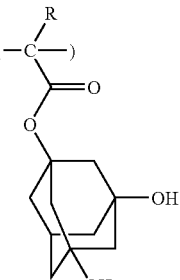
B-3M (R = CH₃)     B-4M (R = CH₃)
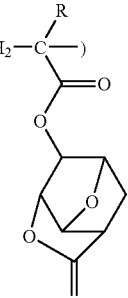     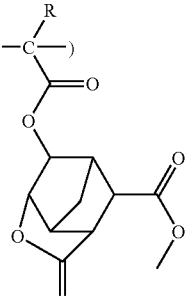
B-5M (R = CH₃)     B-6M (R = CH₃)
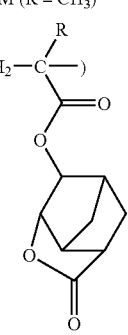     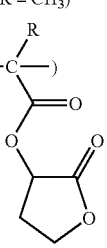
B-7M (R = CH₃)     B-8M (R = CH₃)

TABLE 4-continued

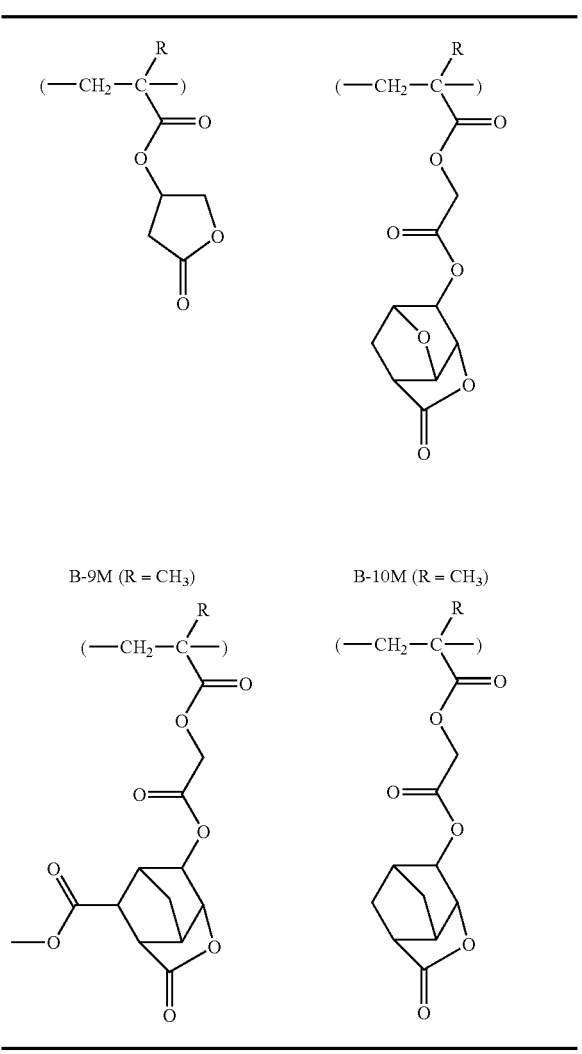

TABLE 5

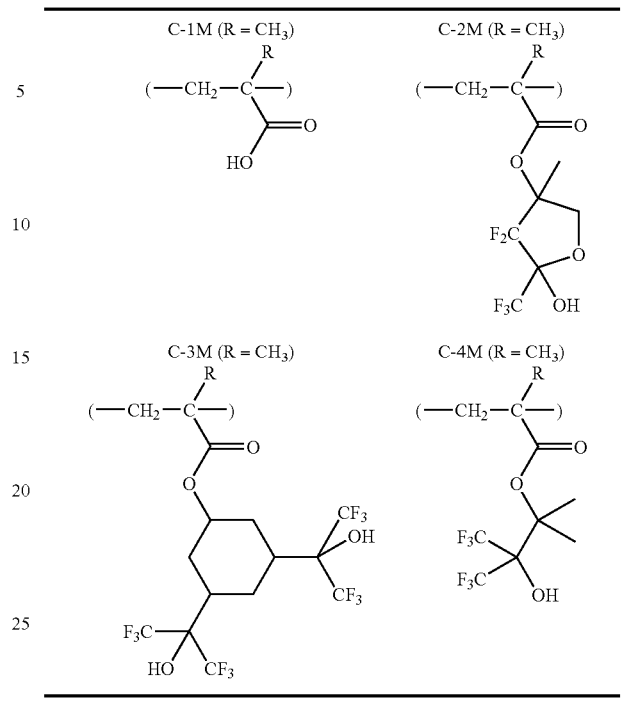

Preparation of Resist Compositions

Examples 3-1 to 3-28 & Comparative Examples 2-1 to 2-4

Resist compositions were prepared by using inventive resins (Polymer 1 to 28) or comparative resins (Polymers 29 to 32) as the base resin, and dissolving the polymer, an acid generator (PAG), and a basic compound (Base) in a solvent mixture (PGMEA and CyHO) containing 0.01 wt % of surfactant KH-20 (Asahi Glass Co., Ltd.) in accordance with the recipe shown in Table 6. These compositions were each filtered through a Teflon® filter having a pore diameter 0.2 μm, thereby giving inventive resist solutions (R-01 to 28) and comparative resist solutions (R-29 to 32).

TABLE 6

|  |  | Resist | Resin (pbw) | PAG (pbw) | Base (pbw) | Solvent 1 (pbw) | Solvent 2 (pbw) |
|---|---|---|---|---|---|---|---|
| Example | 3-1 | R-01 | Polymer 1 (80) | PAG-1 (7.6) | Base-1 (1.10) | PGMEA (1,120) | CyHO (480) |
|  | 3-2 | R-02 | Polymer 2 (80) | PAG-1 (7.6) | Base-1 (1.10) | PGMEA (1,120) | CyHO (480) |
|  | 3-3 | R-03 | Polymer 3 (80) | PAG-1 (7.6) | Base-1 (1.10) | PGMEA (1,120) | CyHO (480) |
|  | 3-4 | R-04 | Polymer 4 (80) | PAG-1 (7.6) | Base-1 (1.10) | PGMEA (1,120) | CyHO (480) |
|  | 3-5 | R-05 | Polymer 5 (80) | PAG-1 (7.6) | Base-1 (1.10) | PGMEA (1,120) | CyHO (480) |
|  | 3-6 | R-06 | Polymer 6 (80) | PAG-1 (7.6) | Base-1 (1.10) | PGMEA (1,120) | CyHO (480) |
|  | 3-7 | R-07 | Polymer 7 (80) | PAG-1 (7.6) | Base-1 (1.10) | PGMEA (1,120) | CyHO (480) |
|  | 3-8 | R-08 | Polymer 8 (80) | PAG-1 (7.6) | Base-1 (1.10) | PGMEA (1,120) | CyHO (480) |
|  | 3-9 | R-09 | Polymer 9 (80) | PAG-1 (7.6) | Base-1 (1.10) | PGMEA (1,120) | CyHO (480) |
|  | 3-10 | R-10 | Polymer 10 (80) | PAG-1 (7.6) | Base-1 (1.10) | PGMEA (1,120) | CyHO (480) |
|  | 3-11 | R-11 | Polymer 11 (80) | PAG-1 (7.6) | Base-1 (1.10) | PGMEA (1,120) | CyHO (480) |
|  | 3-12 | R-12 | Polymer 12 (80) | PAG-1 (7.6) | Base-1 (1.10) | PGMEA (1,120) | CyHO (480) |
|  | 3-13 | R-13 | Polymer 13 (80) | PAG-1 (7.6) | Base-1 (1.10) | PGMEA (1,120) | CyHO (480) |
|  | 3-14 | R-14 | Polymer 14 (80) | PAG-1 (7.6) | Base-1 (1.10) | PGMEA (1,120) | CyHO (480) |
|  | 3-15 | R-15 | Polymer 15 (80) | PAG-1 (7.6) | Base-1 (1.10) | PGMEA (1,120) | CyHO (480) |
|  | 3-16 | R-16 | Polymer 16 (80) | PAG-1 (7.6) | Base-1 (1.10) | PGMEA (1,120) | CyHO (480) |
|  | 3-17 | R-17 | Polymer 17 (80) | PAG-1 (7.6) | Base-1 (1.10) | PGMEA (1,120) | CyHO (480) |
|  | 3-18 | R-18 | Polymer 18 (80) | PAG-1 (7.6) | Base-1 (1.10) | PGMEA (1,120) | CyHO (480) |
|  | 3-19 | R-19 | Polymer 19 (80) | PAG-1 (7.6) | Base-1 (1.10) | PGMEA (1,120) | CyHO (480) |
|  | 3-20 | R-20 | Polymer 20 (80) | PAG-1 (7.6) | Base-1 (1.10) | PGMEA (1,120) | CyHO (480) |
|  | 3-21 | R-21 | Polymer 21 (80) | PAG-1 (7.6) | Base-1 (1.10) | PGMEA (1,120) | CyHO (480) |
|  | 3-22 | R-22 | Polymer 22 (60) | PAG-1 (7.6) | Base-1 (1.10) | PGMEA (1,120) | CyHO (480) |
|  | 3-23 | R-23 | Polymer 23 (80) | PAG-1 (7.6) | Base-1 (1.10) | PGMEA (1,120) | CyHO (480) |

TABLE 6-continued

|  | Resist | Resin (pbw) | PAG (pbw) | Base (pbw) | Solvent 1 (pbw) | Solvent 2 (pbw) |
|---|---|---|---|---|---|---|
|  | 3-24 R-24 | Polymer 24 (80) | PAG-1 (7.6) | Base-1 (1.10) | PGMEA (1,120) | CyHO (480) |
|  | 3-25 R-25 | Polymer 25 (80) | PAG-1 (7.6) | Base-1 (1.10) | PGMEA (1,120) | CyHO (480) |
|  | 3-26 R-26 | Polymer 26 (80) | PAG-1 (7.6) | Base-1 (1.10) | PGMEA (1,120) | CyHO (480) |
|  | 3-27 R-27 | Polymer 27 (80) | PAG-1 (7.6) | Base-1 (1.10) | PGMEA (1,120) | CyHO (480) |
|  | 3-28 R-28 | Polymer 28 (80) | PAG-1 (7.6) | Base-1 (1.10) | PGMEA (1,120) | CyHO (480) |
| Comparative Example | 2-1 R-29 | Polymer 29 (80) | PAG-1 (7.6) | Base-1 (1.10) | PGMEA (1,120) | CyHO (480) |
|  | 2-2 R-30 | Polymer 30 (80) | PAG-1 (7.6) | Base-1 (1.10) | PGMEA (1,120) | CyHO (480) |
|  | 2-3 R-31 | Polymer 31 (80) | PAG-1 (7.6) | Base-1 (1.10) | PGMEA (1,120) | CyHO (480) |
|  | 2-4 R-32 | Polymer 32 (80) | PAG-1 (7.6) | Base-1 (1.10) | PGMEA (1,120) | CyHO (480) |

The acid generator, base and solvent shown in Table 6 have the following meanings.
PAG-1: triphenylsulfonium 2-(adamantane-1-carbonyloxy)-1,1,3,3,3-pentafluoropropane-1-sulfonate
Base-1: 2-morpholinoethyl 2-[2-(2-methoxyethoxy)ethoxy]-acetate
PGMEA: propylene glycol monomethyl ether acetate
CyHO: cyclohexanone Evaluation of Resolution Example 4-1 to 4-18 & Comparative Examples 3-1 to 3-4

Each of inventive resist compositions (R-01 to 28) and comparative resist compositions (R-29 to 32) was spin coated on a silicon wafer having an antireflective coating (ARC-29A, Nissan Chemical Co., Ltd.) of 78 nm thick and baked at 100° C. for 60 seconds, forming a resist film of 120 nm thick. The wafer was exposed by means of an ArF excimer laser stepper (Nikon Corp., NA 0.85), post-exposure baked (PEB) for 60 seconds, and puddle developed with a 2.38 wt % tetramethylammonium hydroxide aqueous solution for 30 seconds, forming a 1:1 line-and-space pattern and a 1:10 isolated line pattern. During the PEB, an optimum temperature for each resist composition was employed.

The patterned wafer was observed under a top-down scanning electron microscope (TDSEM). The optimum exposure (Eop) was defined as the exposure dose (mJ/cm²) which provided a 1:1 resolution at the top and bottom of a 80-nm 1:1 line-and-space pattern. The maximum resolution of the resist was defined as the minimum line width (on-mask size, in increments of 5 nm) of a 1:1 line-and-space pattern that was resolved and separated at the optimum exposure, with smaller values indicating better resolution. The 1:10 isolated line pattern at the optimum exposure was also observed for determining an actual on-wafer size of the isolated line pattern with an on-mask size of 140 nm, which was reported as mask fidelity (on-wafer size, a larger size being better). The pattern was visually observed to see whether or not its profile was rectangular.

Table 7 tabulates the test results (maximum resolution, mask fidelity and profile) of the inventive and comparative resist compositions.

TABLE 7

|  |  | Resist | PEB temperature | Eop | Maximum resolution | Mask fidelity |
|---|---|---|---|---|---|---|
| Example | 4-1 | R-01 | 80° C. | 32.0 mJ/cm² | 75 nm | 83 nm |
|  | 4-2 | R-02 | 80° C. | 35.0 mJ/cm² | 75 nm | 81 nm |
|  | 4-3 | R-03 | 80° C. | 28.0 mJ/cm² | 75 nm | 83 nm |
|  | 4-4 | R-04 | 95° C. | 34.0 mJ/cm² | 70 nm | 90 nm |
|  | 4-5 | R-05 | 95° C. | 37.0 mJ/cm² | 70 nm | 93 nm |
|  | 4-6 | R-06 | 95° C. | 30.0 mJ/cm² | 70 nm | 88 nm |
|  | 4-7 | R-07 | 95° C. | 36.0 mJ/cm² | 70 nm | 88 nm |
|  | 4-8 | R-08 | 95° C. | 38.0 mJ/cm² | 70 nm | 91 nm |
|  | 4-9 | R-09 | 95° C. | 32.0 mJ/cm² | 70 nm | 86 nm |
|  | 4-10 | R-10 | 85° C. | 33.0 mJ/cm² | 70 nm | 92 nm |
|  | 4-11 | R-11 | 85° C. | 35.0 mJ/cm² | 70 nm | 94 nm |
|  | 4-12 | R-12 | 85° C. | 30.0 mJ/cm² | 70 nm | 90 nm |
|  | 4-13 | R-13 | 95° C. | 35.0 mJ/cm² | 70 nm | 92 nm |
|  | 4-14 | R-14 | 95° C. | 35.0 mJ/cm² | 70 nm | 87 nm |
|  | 4-15 | R-15 | 85° C. | 36.0 mJ/cm² | 70 nm | 94 nm |
|  | 4-16 | R-16 | 90° C. | 36.0 mJ/cm² | 70 nm | 95 nm |
|  | 4-17 | R-17 | 90° C. | 37.0 mJ/cm² | 70 nm | 93 nm |
|  | 4-18 | R-18 | 90° C. | 37.0 mJ/cm² | 70 nm | 93 nm |
|  | 4-19 | R-19 | 95° C. | 36.0 mJ/cm² | 70 nm | 95 nm |
|  | 4-20 | R-20 | 95° C. | 33.0 mJ/cm² | 70 nm | 92 nm |
|  | 4-21 | R-21 | 95° C. | 34.0 mJ/cm² | 70 nm | 93 nm |
|  | 4-22 | R-22 | 95° C. | 32.0 mJ/cm² | 70 nm | 91 nm |
|  | 4-23 | R-23 | 95° C. | 37.0 mJ/cm² | 70 nm | 92 nm |
|  | 4-24 | R-24 | 95° C. | 38.0 mJ/cm² | 70 nm | 93 nm |
|  | 4-25 | R-25 | 95° C. | 40.0 mJ/cm² | 75 nm | 90 nm |
|  | 4-26 | R-26 | 95° C. | 38.0 mJ/cm² | 70 nm | 91 nm |
|  | 4-27 | R-27 | 95° C. | 39.0 mJ/cm² | 70 nm | 95 nm |
|  | 4-28 | R-28 | 95° C. | 39.0 mJ/cm² | 75 nm | 91 nm |
| Comparative Example | 3-1 | R-29 | 105° C. | 36.0 mJ/cm² | 75 nm | 78 nm |
|  | 3-2 | R-30 | 120° C. | 32.0 mJ/cm² | 75 nm | 79 nm |
|  | 3-3 | R-31 | 95° C. | 32.0 mJ/cm² | 75 nm | 79 nm |
|  | 3-4 | R-32 | 95° C. | 32.0 mJ/cm² | 75 nm | 80 nm |

It is seen from the results of Table 7 that the resist compositions within the scope of the invention display improved resolution, mask fidelity, and a satisfactory pattern profile, when processed by ArF excimer laser lithography.

Japanese Patent Application No. 2008-304123 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An acetal compound having the general formula (1):

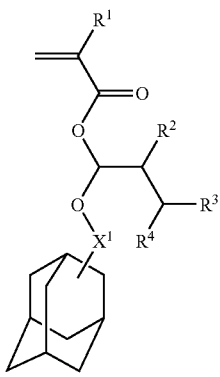
(1)

wherein $R^1$ is hydrogen, methyl or trifluoromethyl, $R^2$ is a straight, branched or cyclic monovalent $C_1$-$C_{10}$ hydrocarbon group, $R^3$ and $R^4$ are each independently hydrogen or a straight, branched or cyclic monovalent $C_1$-$C_{10}$ hydrocarbon group, $R^2$ and $R^3$ may bond together to form an aliphatic hydrocarbon ring with the carbon atoms to which they are attached, and $X^1$ is a single bond or a straight or branched divalent $C_1$-$C_4$ hydrocarbon group.

2. The acetal compound of claim 1, wherein said acetal compound is one selected from the group consisting of:

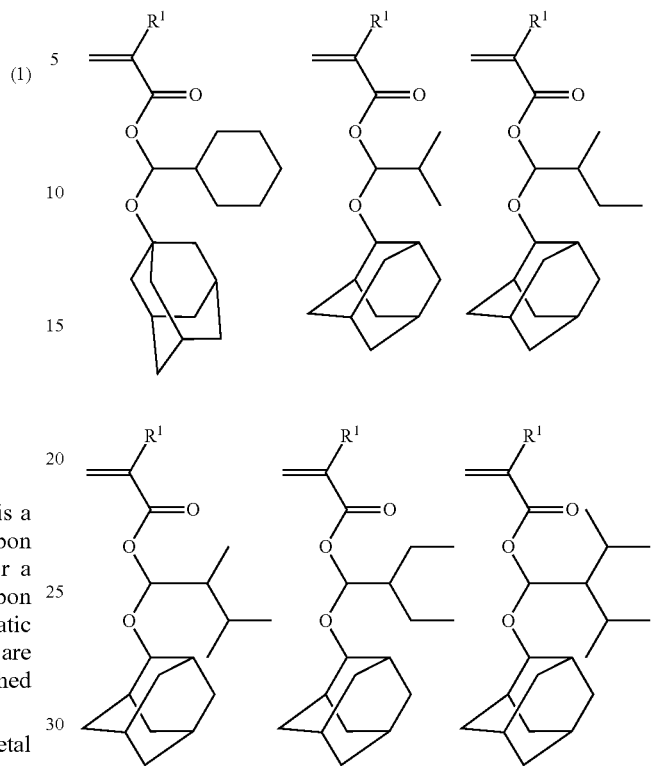

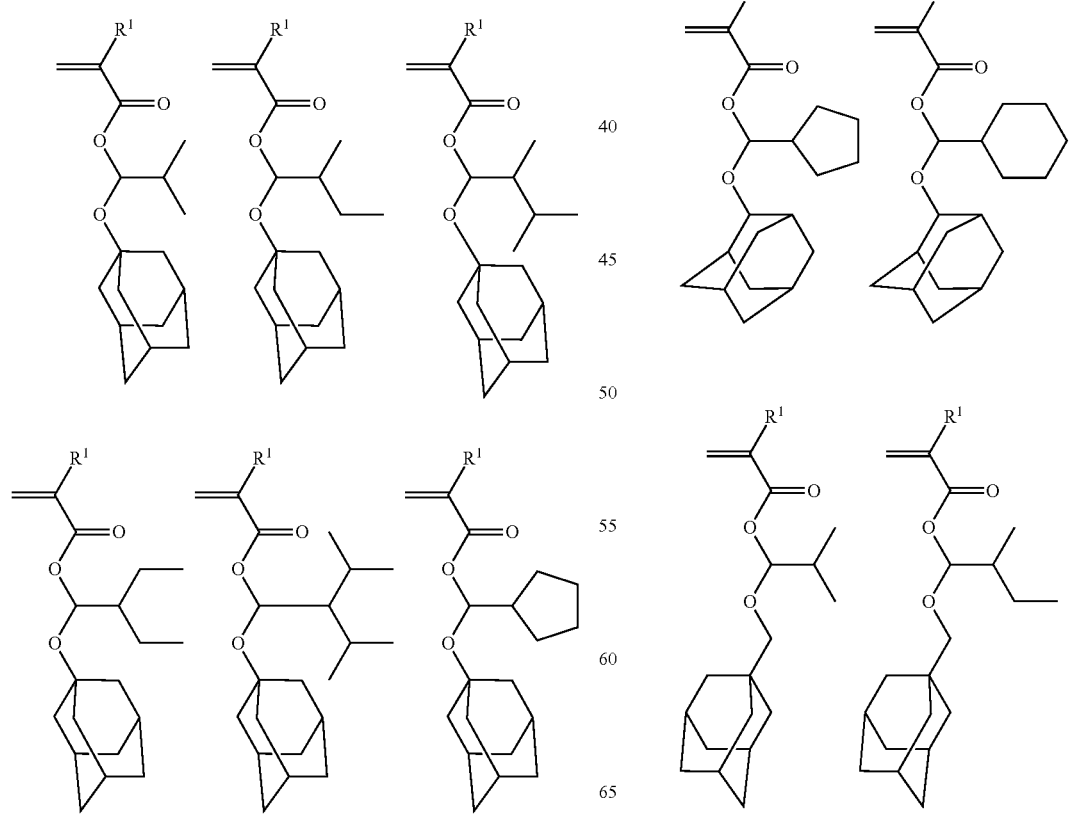

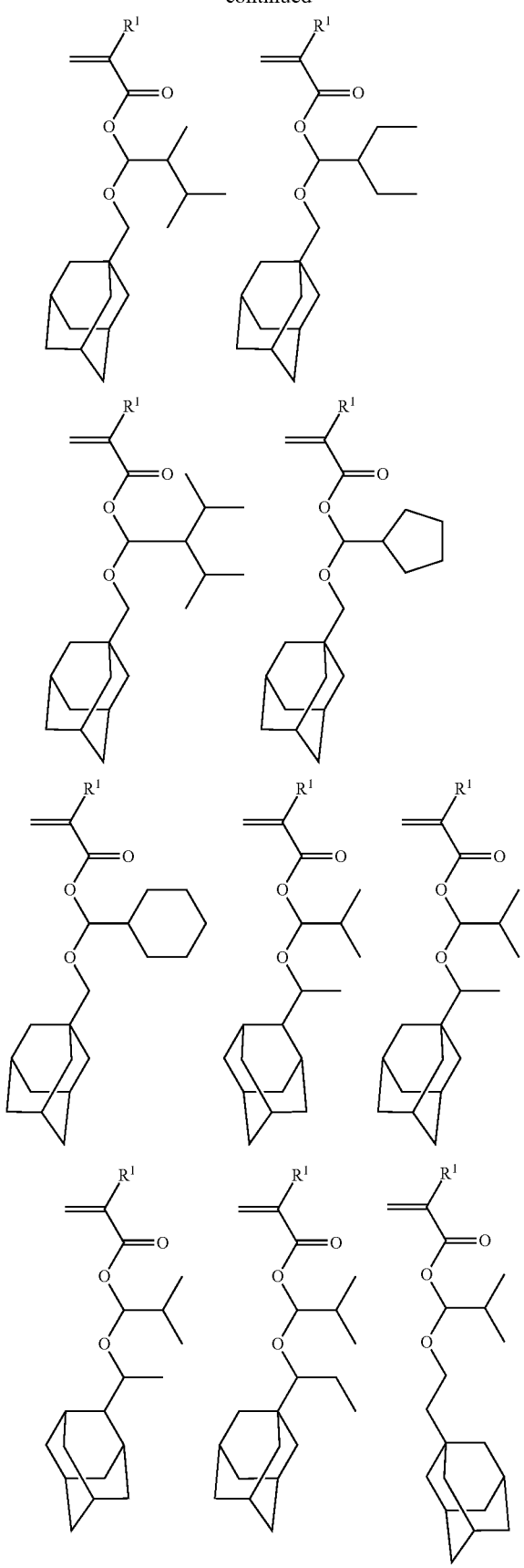
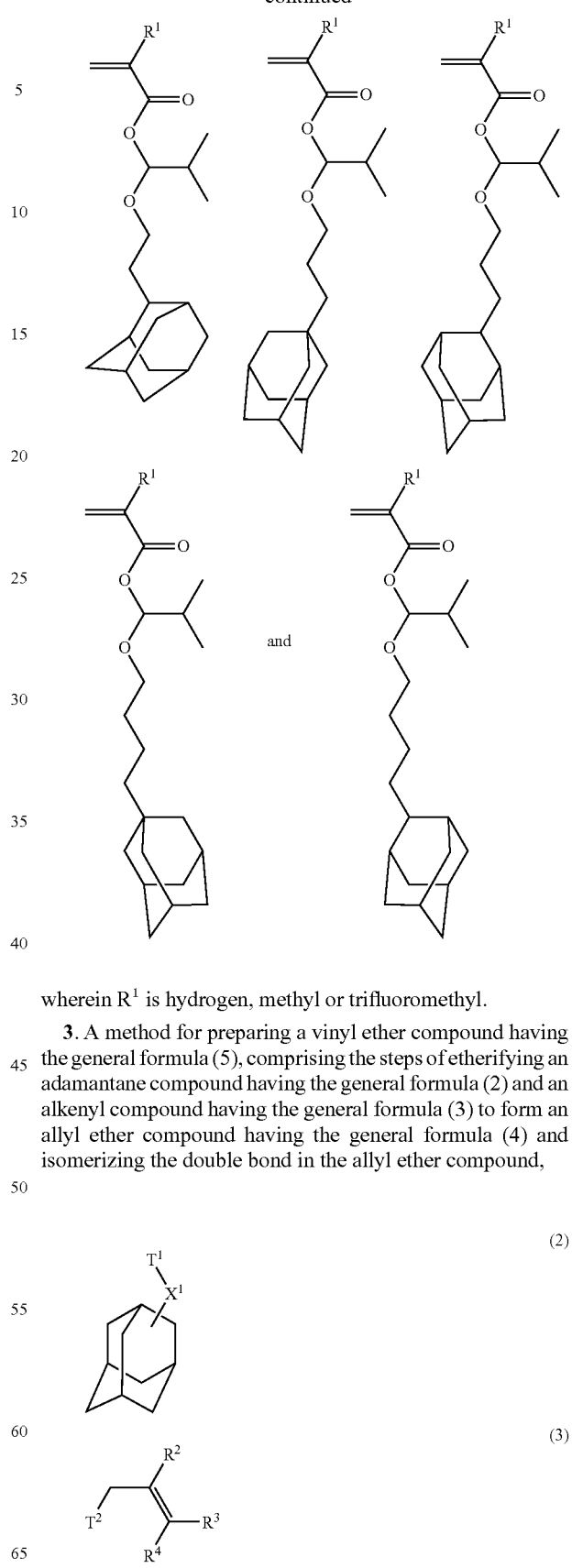

wherein R¹ is hydrogen, methyl or trifluoromethyl.

3. A method for preparing a vinyl ether compound having the general formula (5), comprising the steps of etherifying an adamantane compound having the general formula (2) and an alkenyl compound having the general formula (3) to form an allyl ether compound having the general formula (4) and isomerizing the double bond in the allyl ether compound,

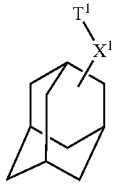
(2)

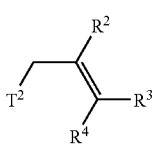
(3)

(4)

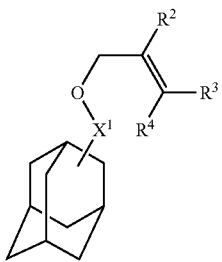

(5)

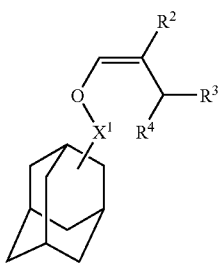

wherein R² is a straight, branched or cyclic monovalent C₁-C₁₀ hydrocarbon group, R³ and R⁴ are each independently hydrogen or a straight, branched or cyclic monovalent C₁-C₁₀ hydrocarbon group, R² and R³ may bond together to form an aliphatic hydrocarbon ring with the carbon atoms to which they are attached, X¹ is a single bond or a straight or branched divalent C₁-C₄ hydrocarbon group, T¹ and T² are each independently a hydroxyl group, halogen atom, alkanesulfonyloxy or arenesulfonyloxy group.

4. A method for preparing an acetal compound having the general formula (1), comprising the steps of effecting addition reaction of a hydrogen halide to a vinyl ether compound having the general formula (5) to form a halogenated alkyl ether compound having the general formula (6), and esterifying the halogenated alkyl ether compound with a corresponding carboxylic acid salt having the general formula (7), (5)

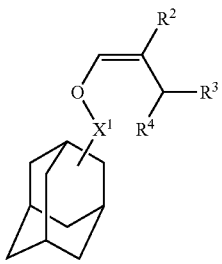

(6)

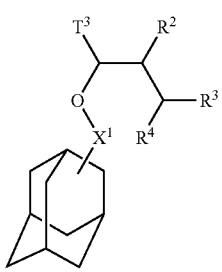

(7)

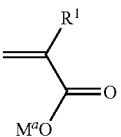

(1)

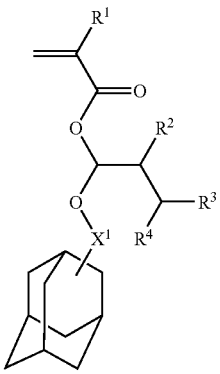

wherein R¹ is hydrogen, methyl or trifluoromethyl, R² is a straight, branched or cyclic C₁-C₁₀ hydrocarbon group, R³ and R⁴ are each independently hydrogen or a straight, branched or cyclic C₁-C₁₀ hydrocarbon group, R² and R³ may bond together to form an aliphatic hydrocarbon ring with the carbon atoms to which they are attached, X¹ is a single bond or a straight or branched divalent C₁-C₄ hydrocarbon group, T³ is a halogen atom, and Mᵃ is Li, Na, K, Mg₁/₂, Ca₁/₂ or substituted or unsubstituted ammonium.

5. A polymer comprising recurring units of the general formula (8):

(8)

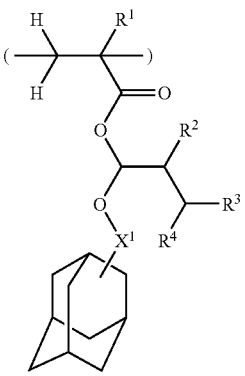

wherein R¹ is hydrogen, methyl or trifluoromethyl, R² is a straight, branched or cyclic monovalent C₁-C₁₀ hydrocarbon group, R³ and R⁴ are each independently hydrogen or a straight, branched or cyclic monovalent C₁-C₁₀ hydrocarbon group, R² and R³ may bond together to form an aliphatic hydrocarbon ring with the carbon atoms to which they are attached, and X¹ is a single bond or a straight or branched divalent C₁-C₄ hydrocarbon group.

6. The polymer of claim 5, further comprising recurring units of at least one type selected from the general formulae (9) to (12):

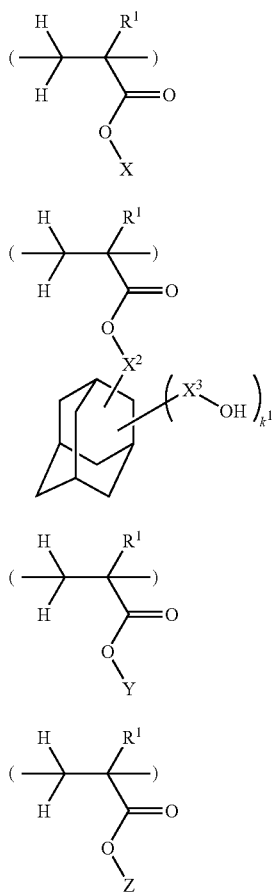

wherein $R^1$ is as defined above, X is an acid labile group different from formula (8), Y is a substituent group having lactone structure, Z is hydrogen, $C_1$-$C_{15}$ fluoroalkyl or $C_1$-$C_{15}$ fluoroalcohol-containing substituent group, $X^2$ and $X^3$ are each independently a single bond or a straight or branched divalent $C_1$-$C_4$ hydrocarbon group, and $k^1$ is an integer of 1 to 3.

7. The polymer of claim 6, wherein the acid labile group represented by X is selected from the group consisting of groups of the following general formulae (L1) to (L4), tertiary alkyl groups of 4 to 20 carbon atoms, trialkylsilyl groups in which each alkyl moiety has 1 to 6 carbon atoms, and oxoalkyl groups of 4 to 20 carbon atoms:

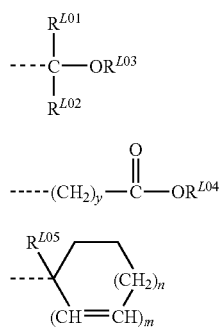

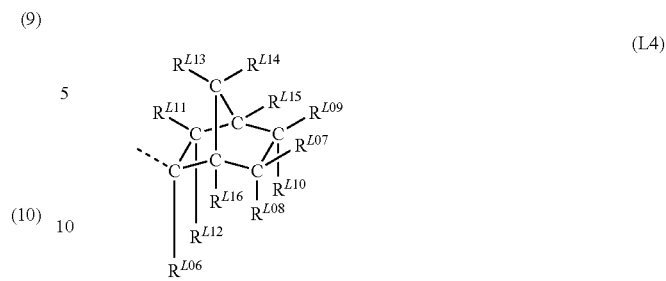

wherein the broken line denotes a valence bond;

$R^{L01}$ and $R^{L02}$ are hydrogen or straight, branched or cyclic alkyl groups of 1 to 18 carbon atoms; $R^{L03}$ is an unsubstituted straight, branched or cyclic alkyl group of 1 to 18 carbon atoms, and substituted forms of such alkyl groups in which some hydrogen atoms are replaced by hydroxyl, alkoxy, oxo, amino, or alkylamino; a pair of $R^{L01}$ and $R^{L02}$, $R^{L01}$ and $R^{L03}$, or $R^{L02}$ and $R^{L03}$ may bond together to form a ring with the carbon and oxygen atoms to which they are attached, $R^{L01}$, $R^{L02}$ and $R^{L03}$ is a straight or branched alkylene group of 1 to 18 carbon atoms when they form a ring;

$R^{L04}$ is a tertiary alkyl group of 4 to 20 carbon atoms, a trialkylsilyl group in which each alkyl moiety has 1 to 6 carbon atoms, an oxoalkyl group of 4 to 20 carbon atoms, or a group of formula (L1);

$R^{L05}$ is a substituted or unsubstituted, straight, branched or cyclic $C_1$-$C_8$ alkyl group or a substituted or unsubstituted $C_6$-$C_{20}$ aryl group; letter m is equal to 0 or 1, n is equal to 0, 1, 2 or 3, and 2m+n is equal to 2 or 3;

$R^{L06}$ is a substituted or unsubstituted, straight, branched or cyclic $C_1$-$C_8$ alkyl group or a substituted or unsubstituted $C_6$-$C_{20}$ aryl group;

$R^{L07}$ to $R^{L16}$ independently represent hydrogen or monovalent $C_1$-$C_{15}$ hydrocarbon groups; $R^{L07}$ to $R^{L16}$, taken together, form a ring with the carbon atom to which they are attached, each of $R^{L07}$ to $R^{L16}$ represents a divalent $C_1$-$C_{15}$ hydrocarbon group when they form a ring; and two of $R^{L07}$ to $R^{L16}$ which are attached to vicinal carbon atoms may bond together directly to form a double bond.

8. The polymer of claim 6, wherein the unit of the general formula (9) is selected form the group consisting of:

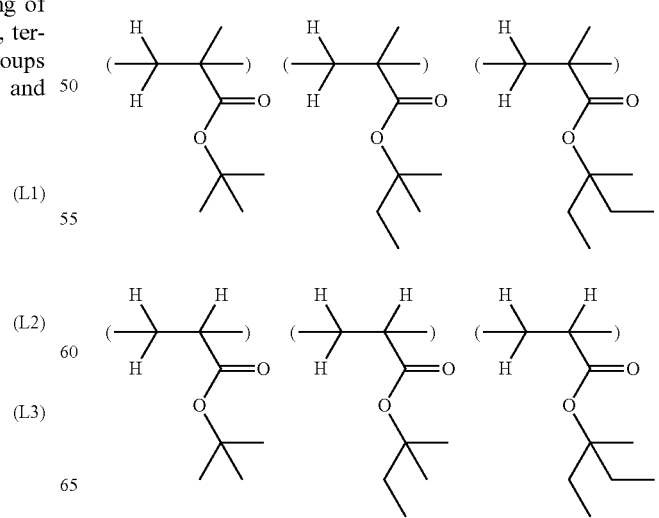

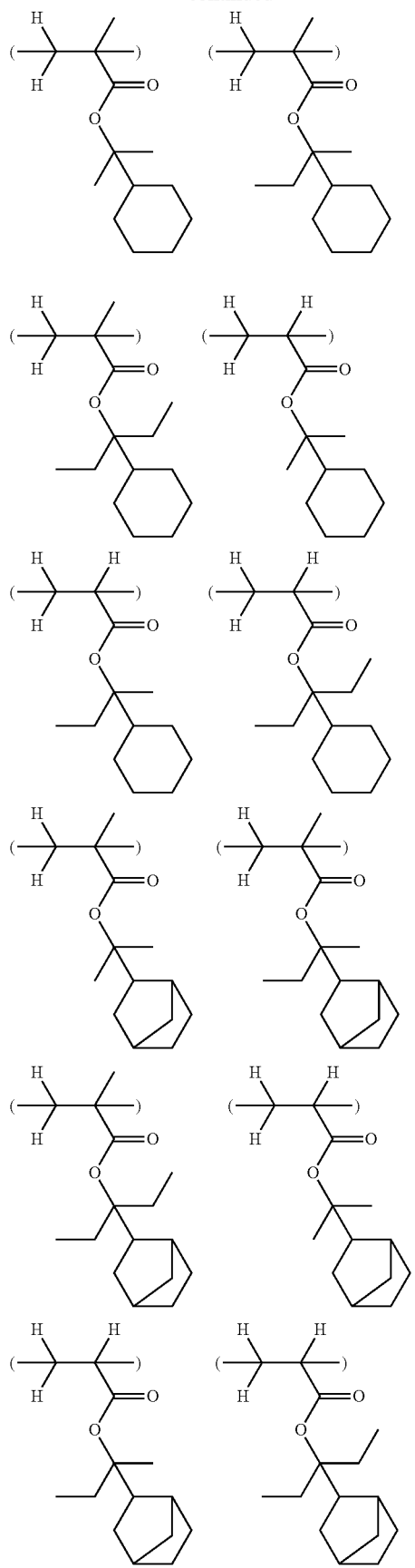
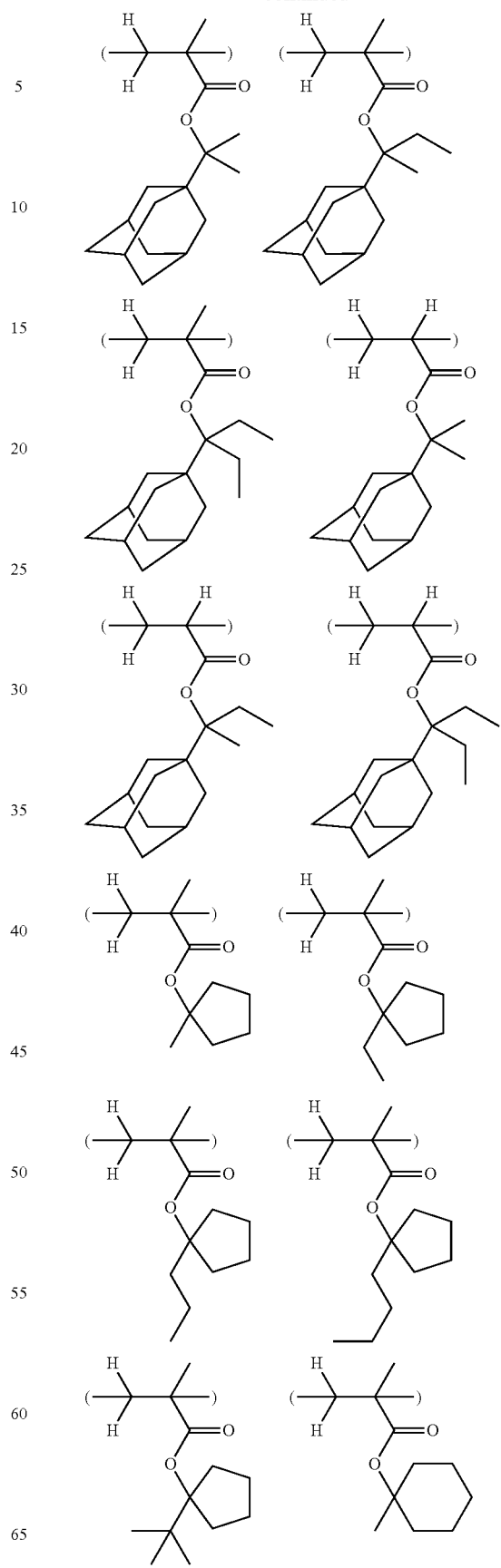

121
-continued
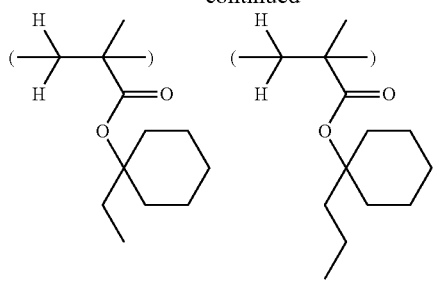
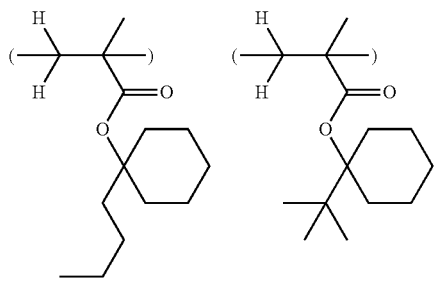
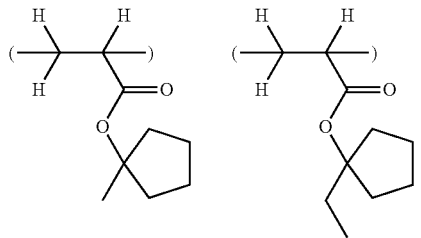
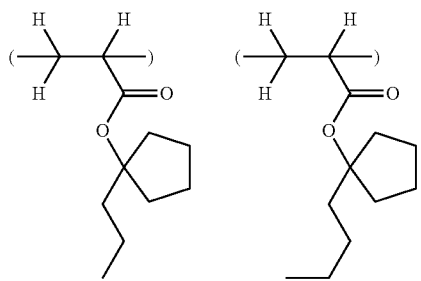
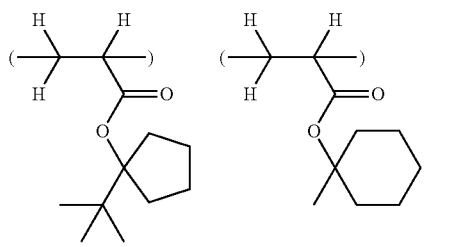
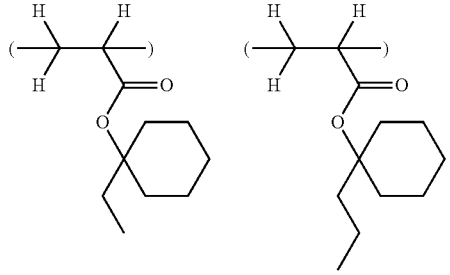
122
-continued
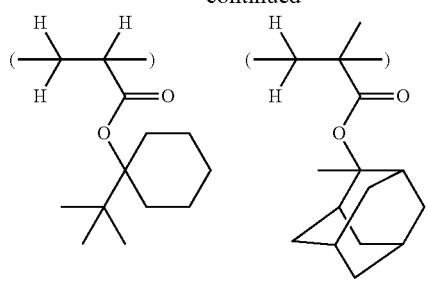
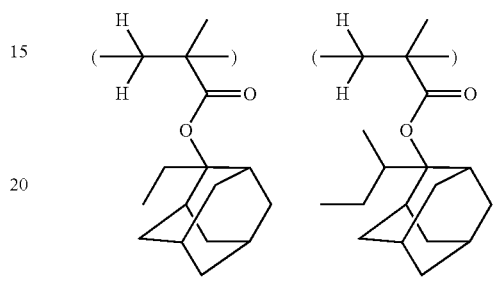
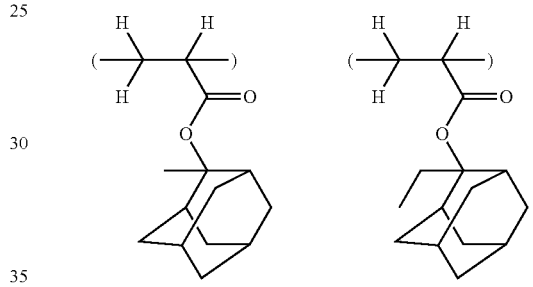
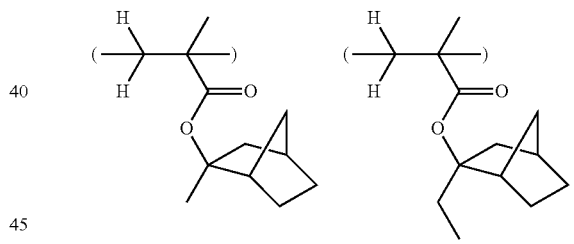
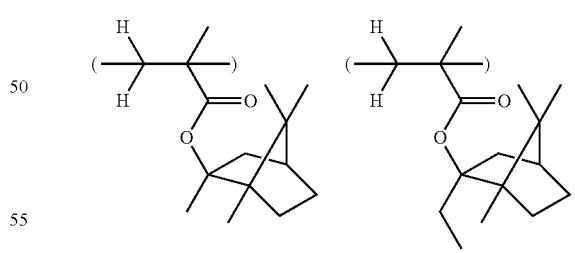
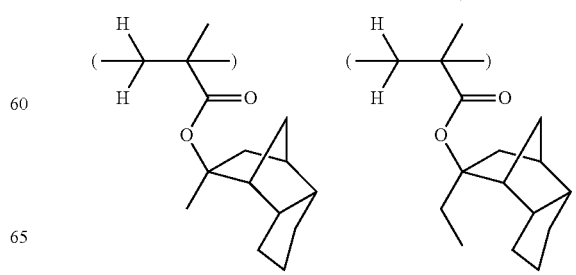

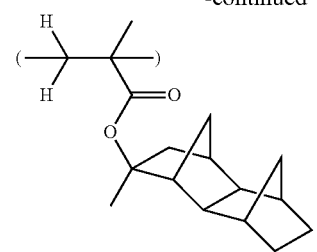
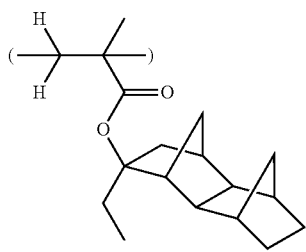
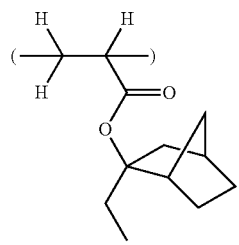
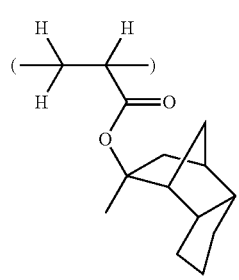
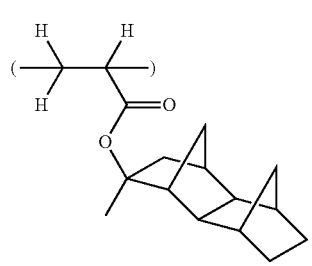
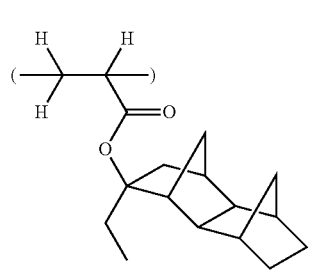
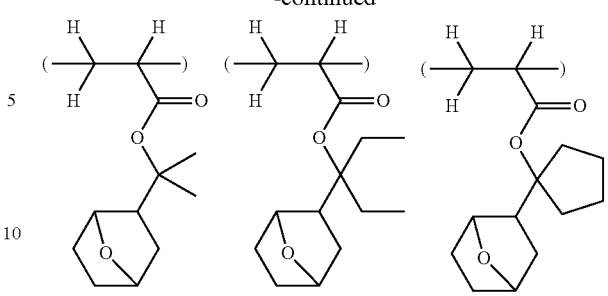
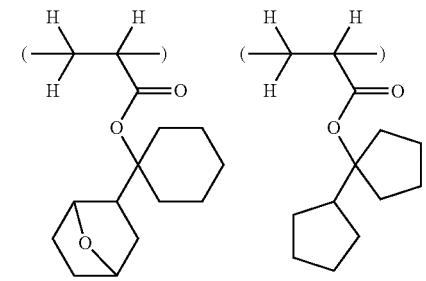
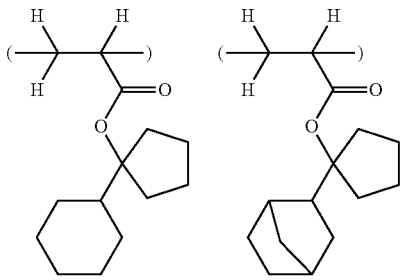
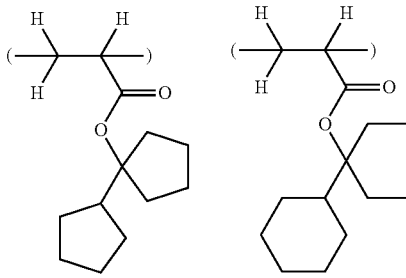
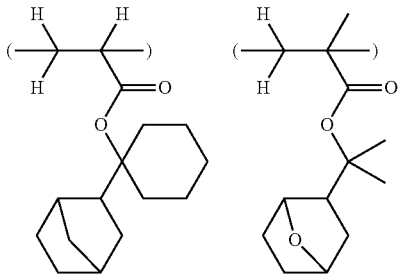
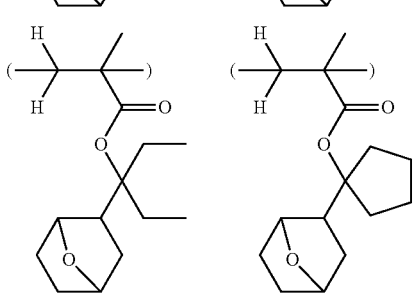

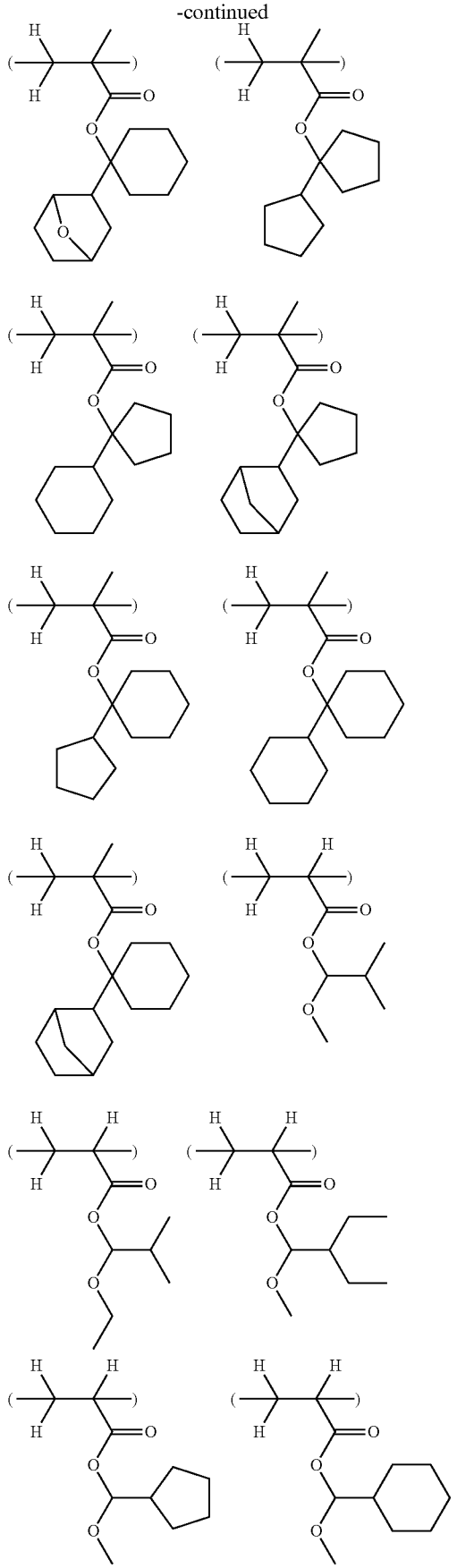
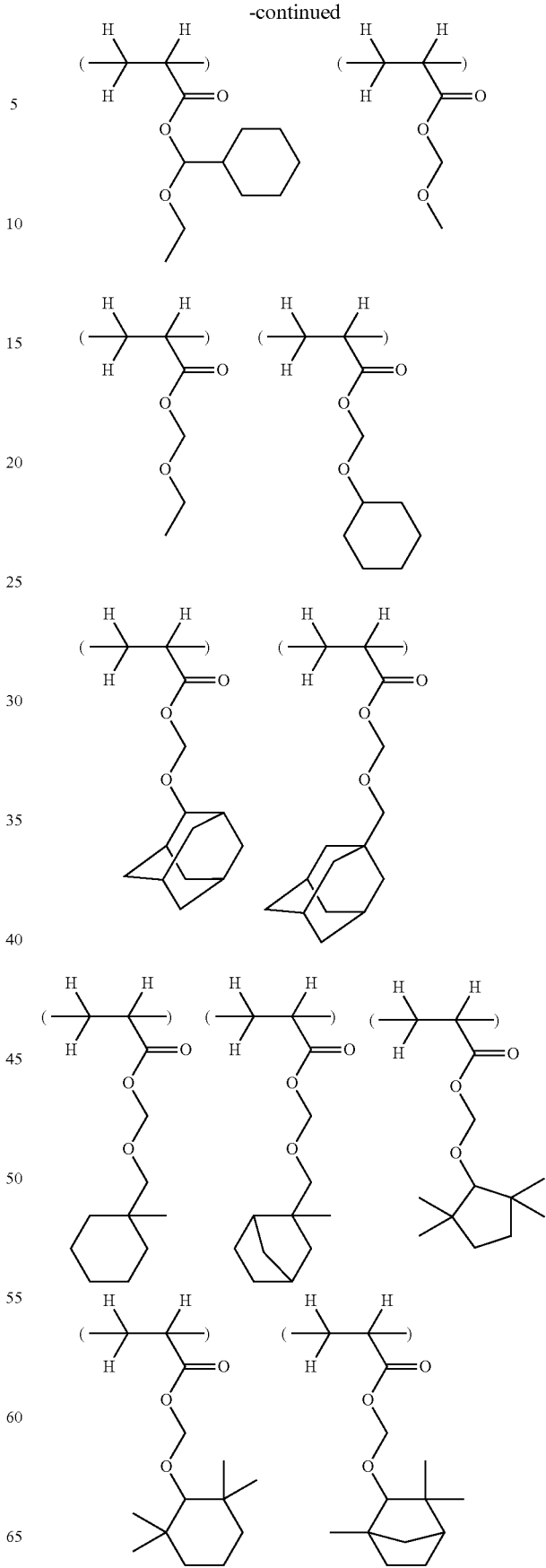

127
-continued
128
-continued
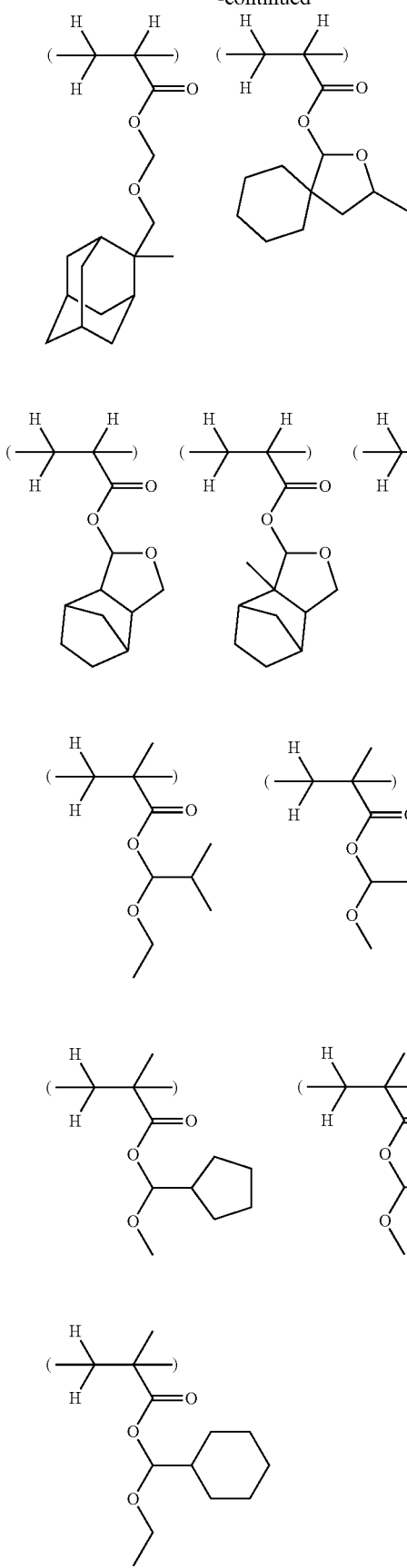
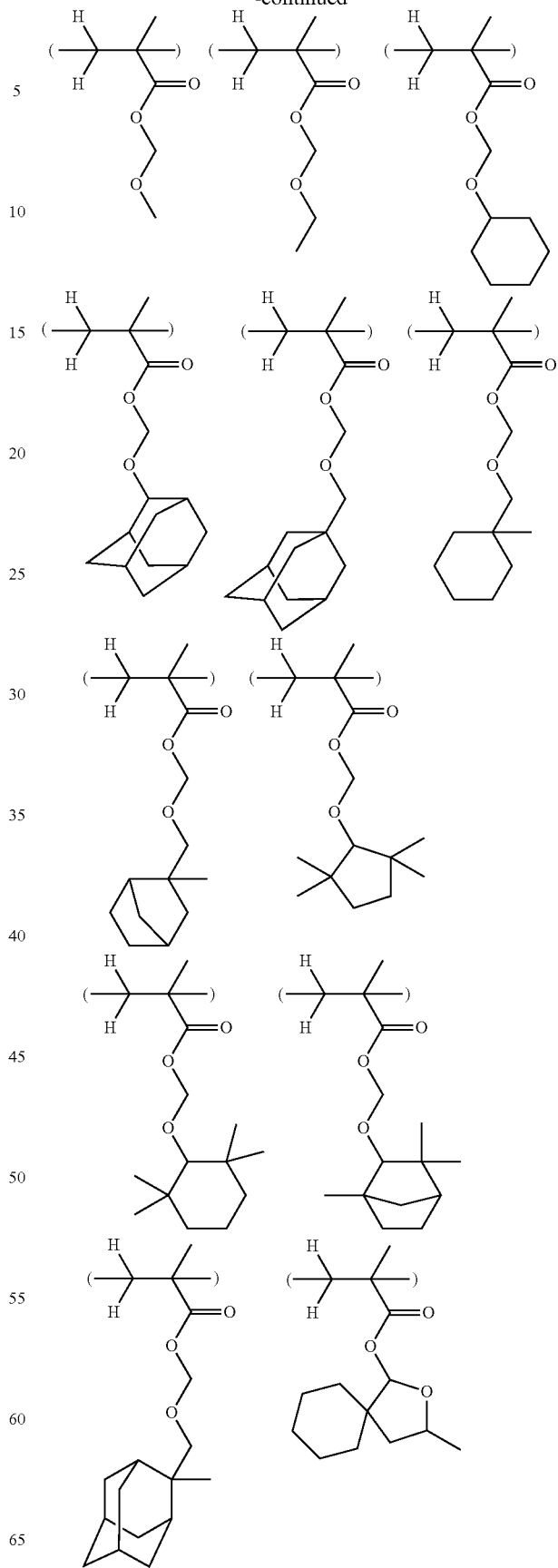

-continued
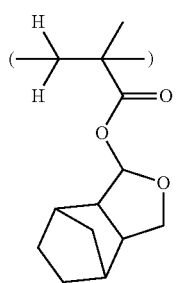 and 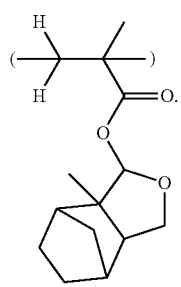
9. The polymer of claim 6, wherein the unit of general formula (10) is selected form the group consisting of:
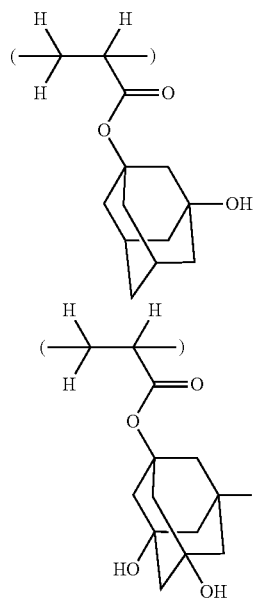
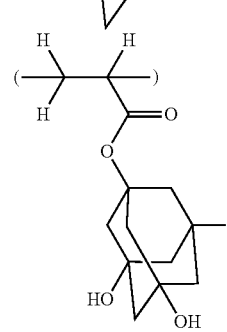
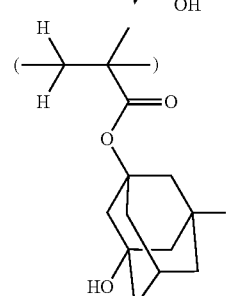
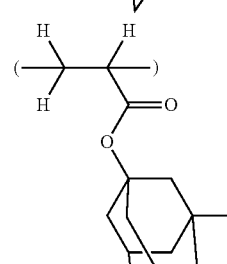
-continued
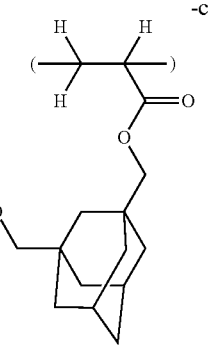 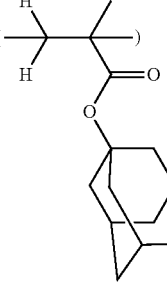
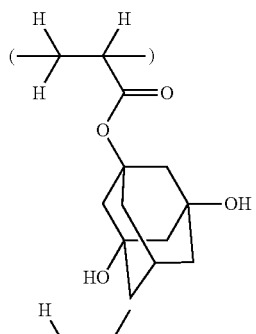
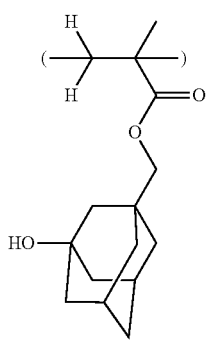 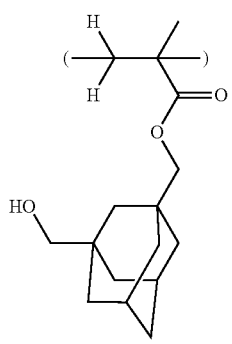
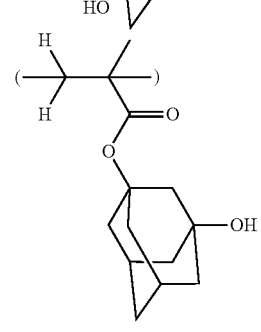
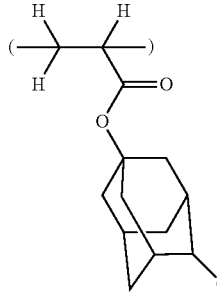 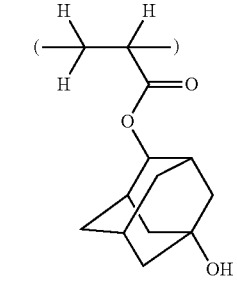
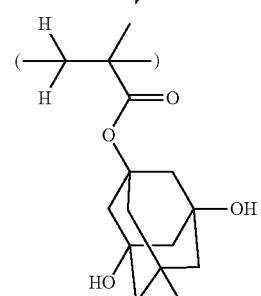
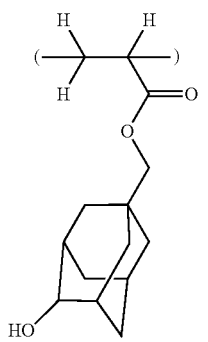 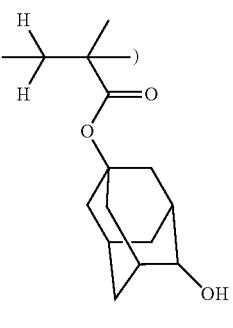
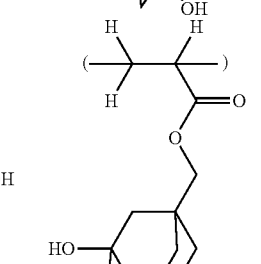
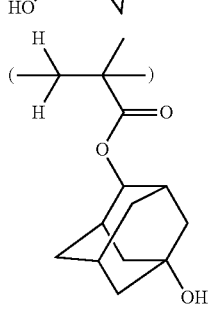 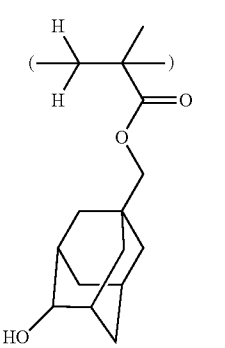

-continued
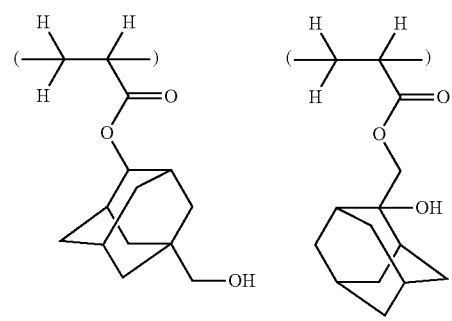
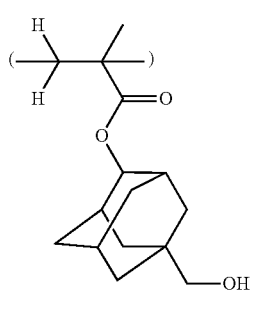
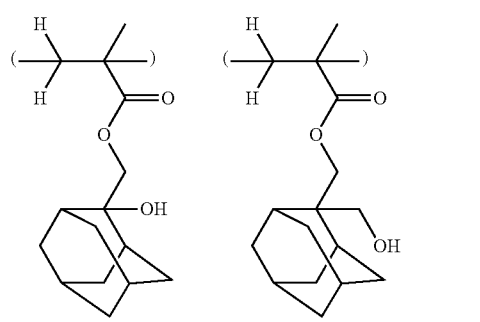
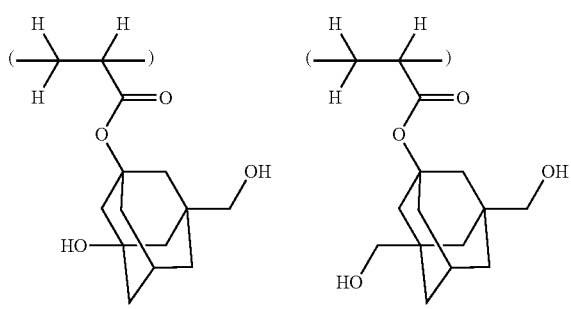
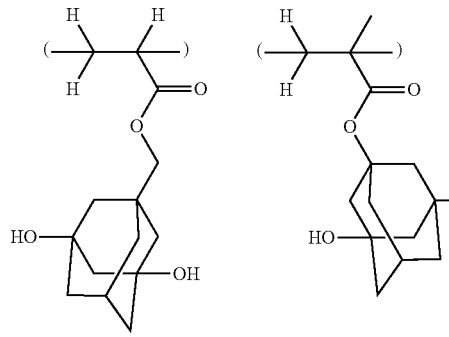
-continued
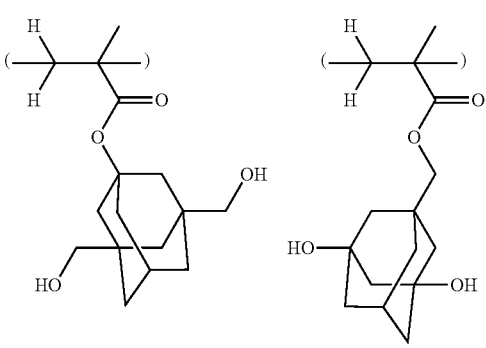
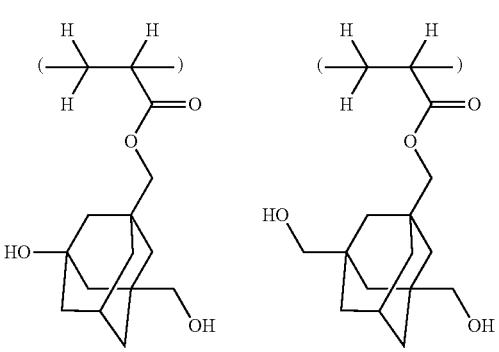
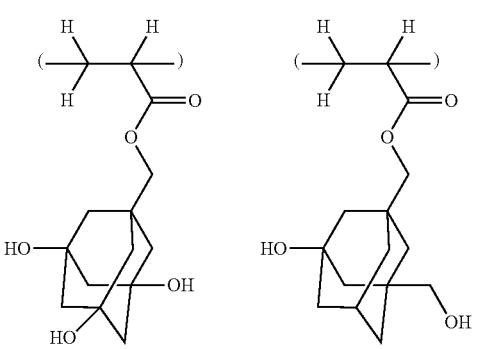
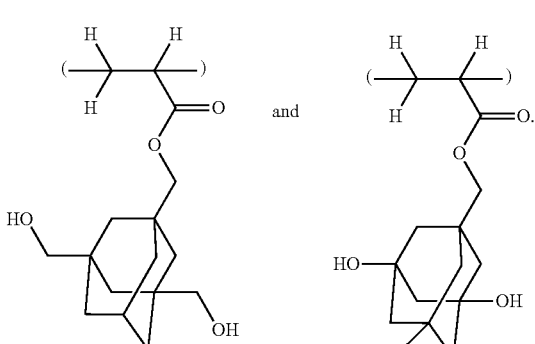
10. The polymer of claim 6, wherein the unit of general formula (11) is selected form the group consisting of:

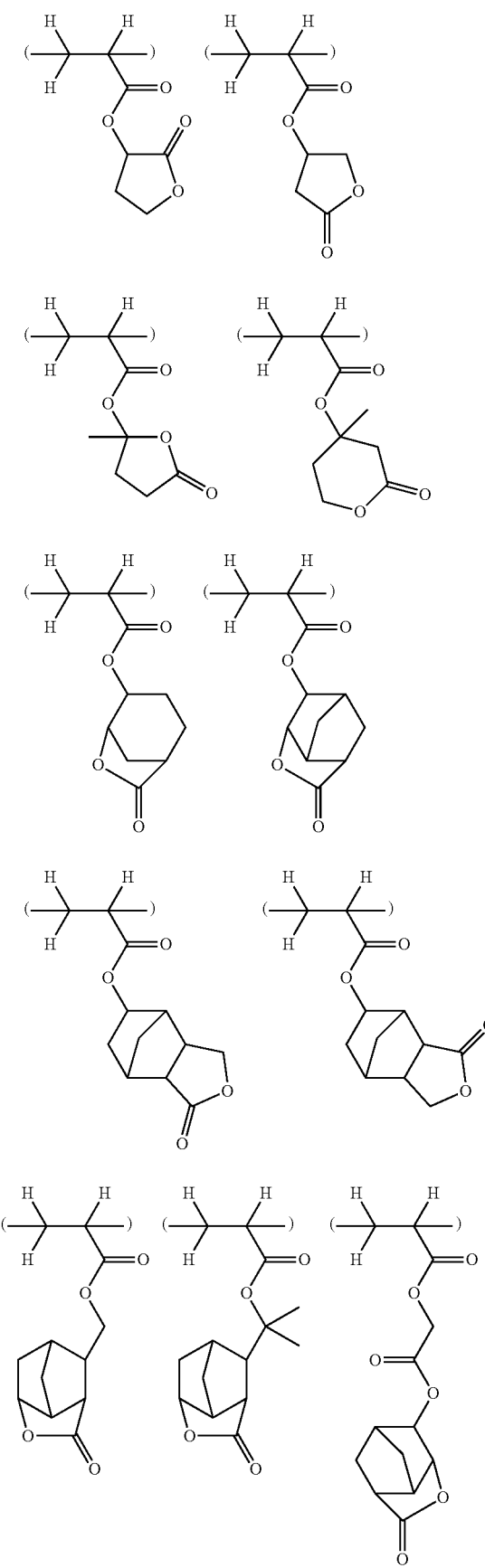
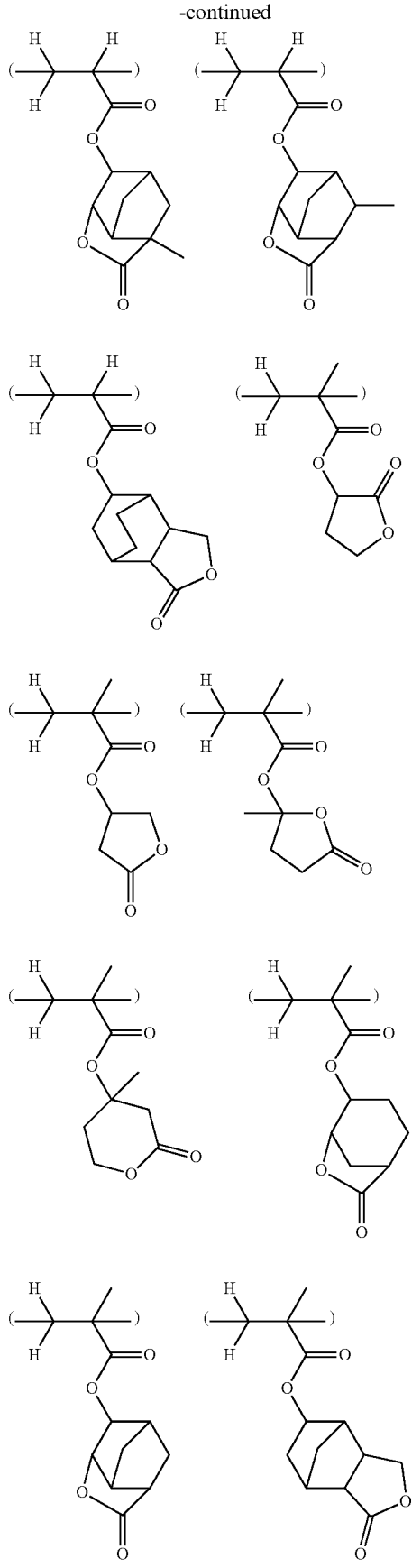

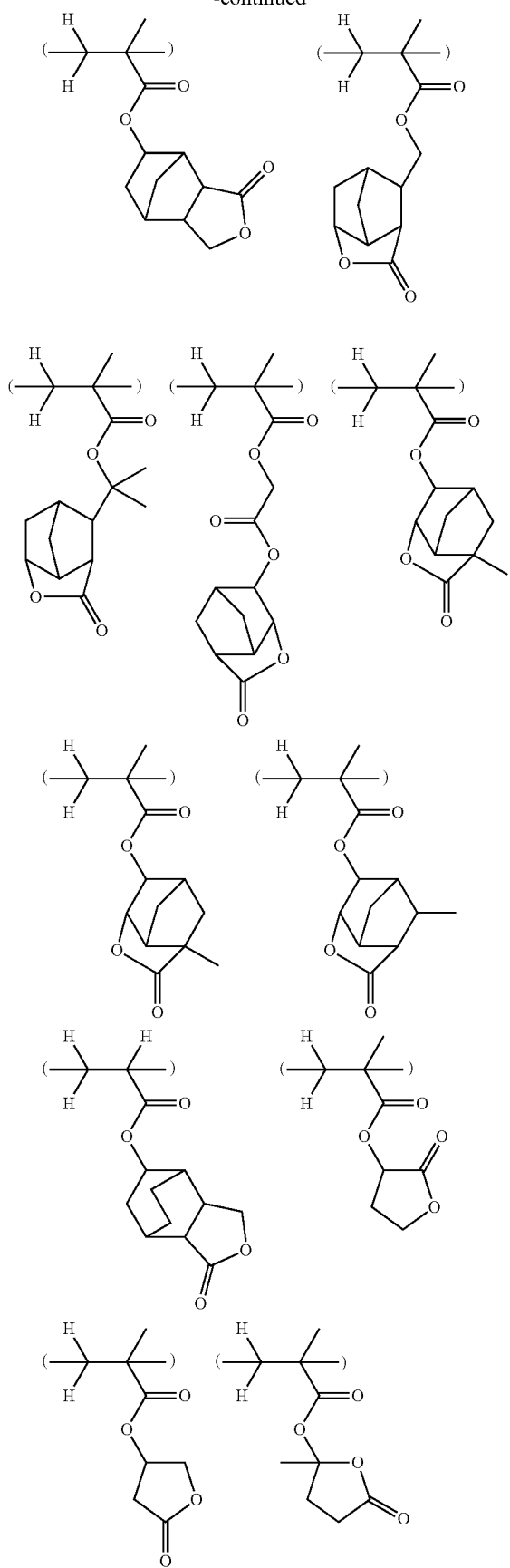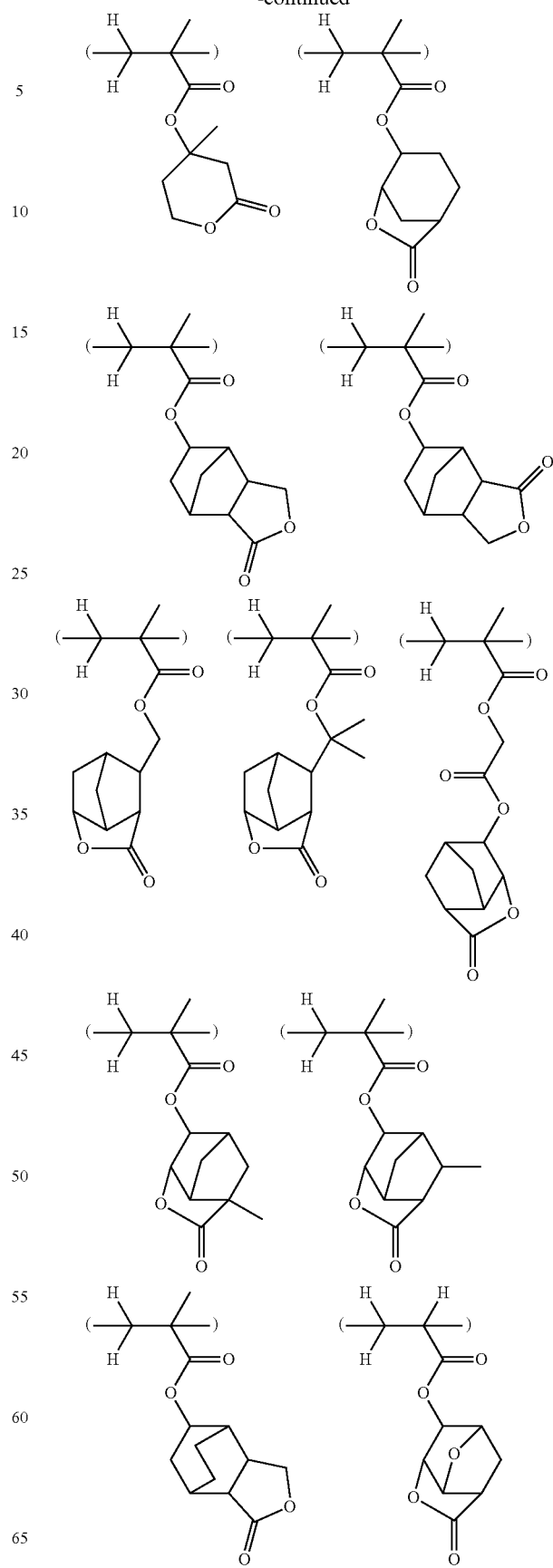

137
-continued
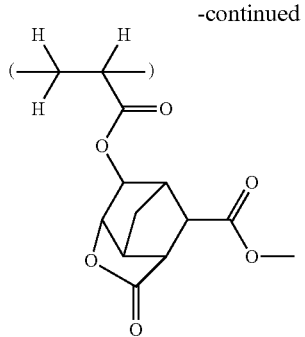
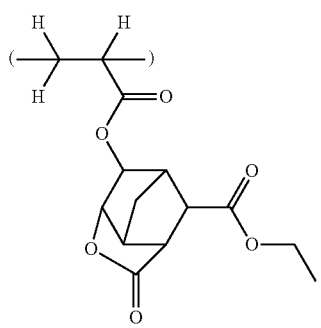
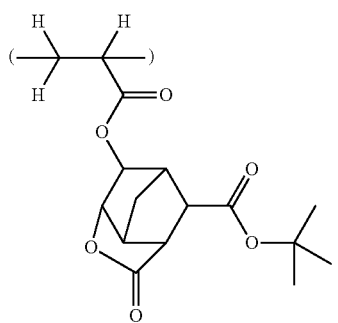
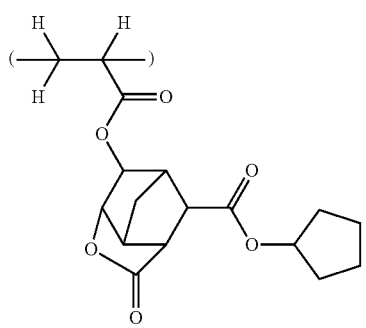
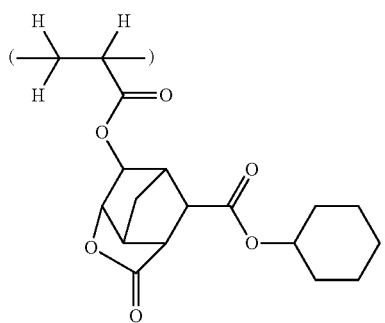
138
-continued
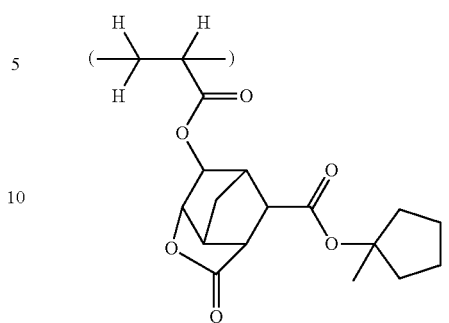
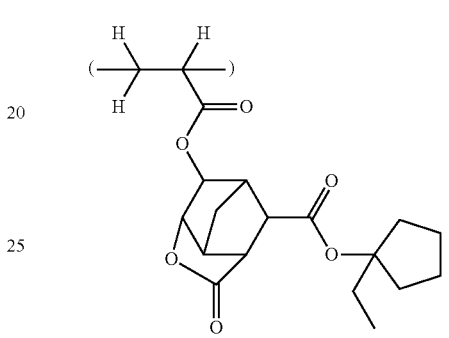
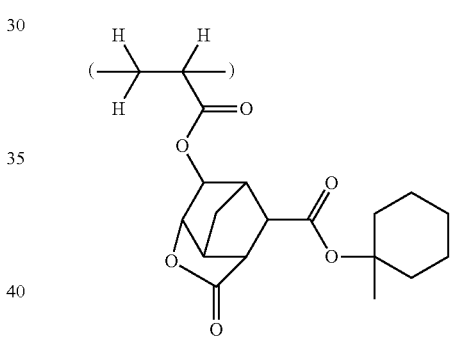
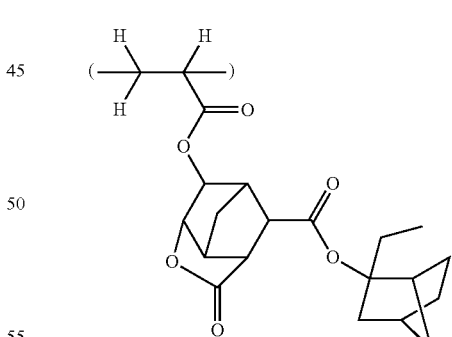
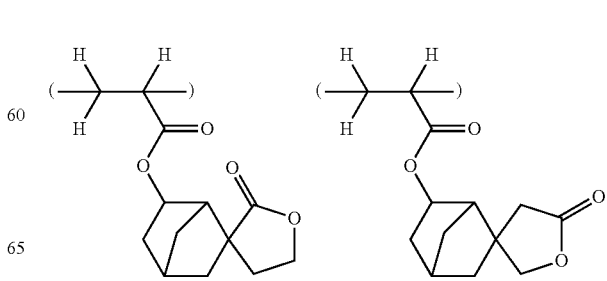

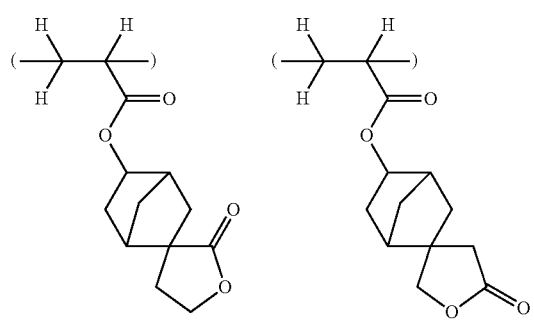
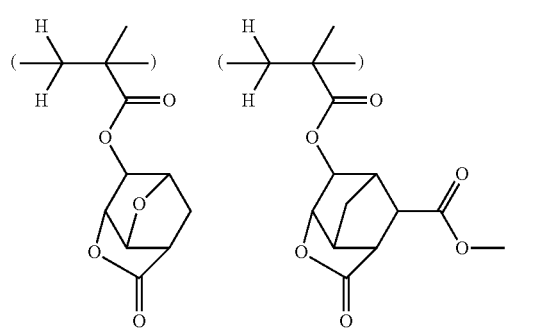
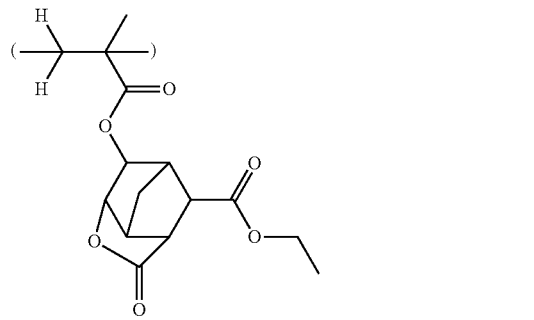
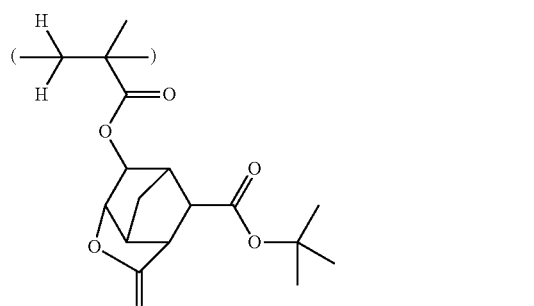
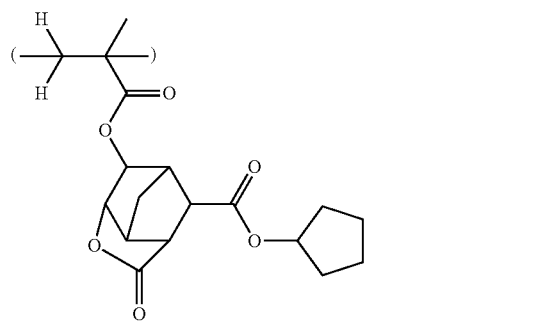
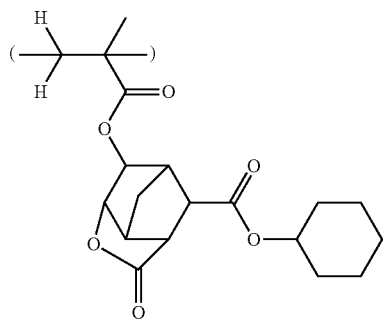
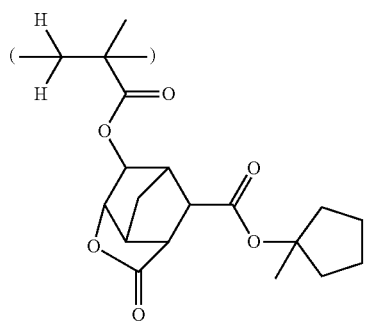
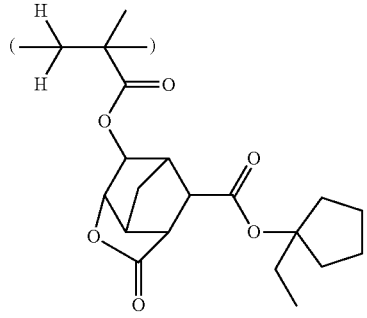
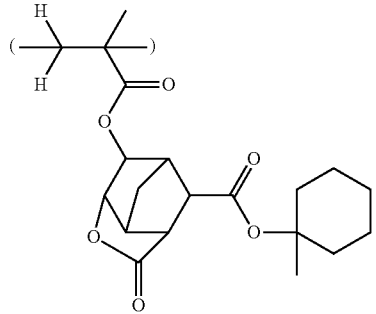
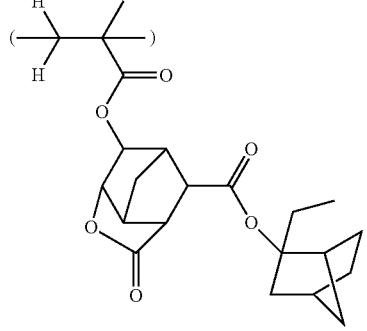

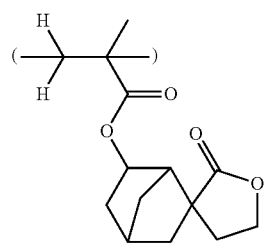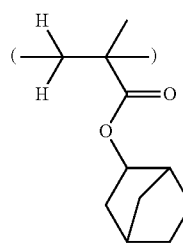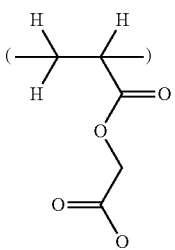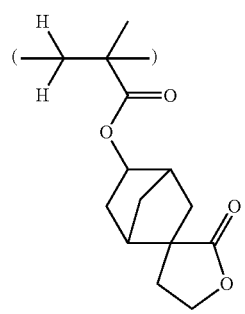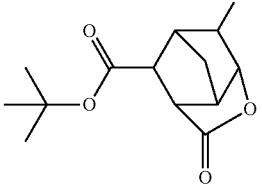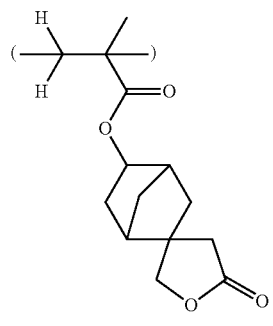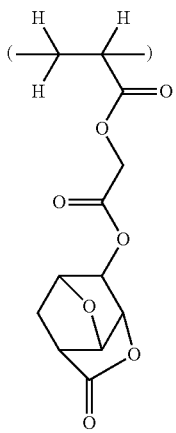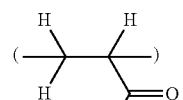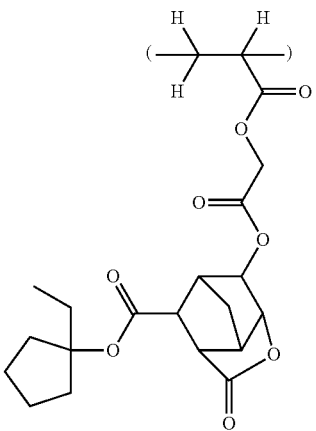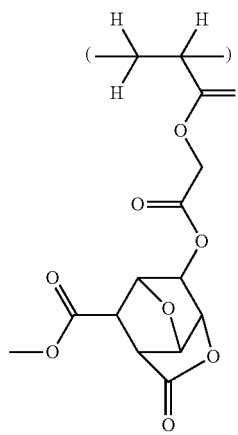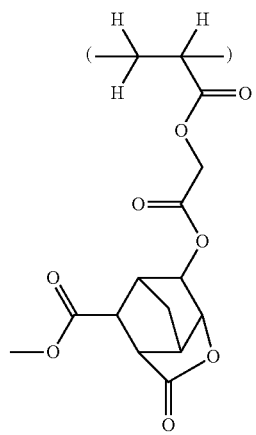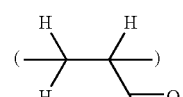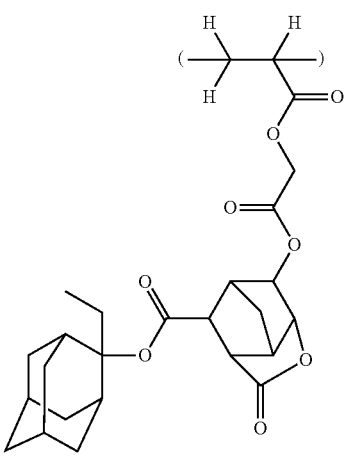

143
-continued
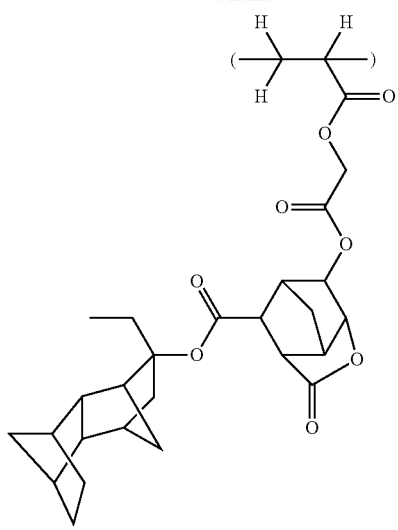
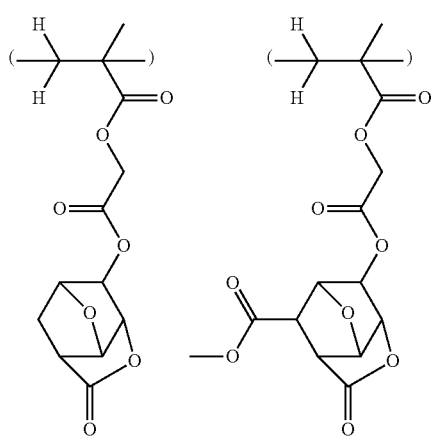
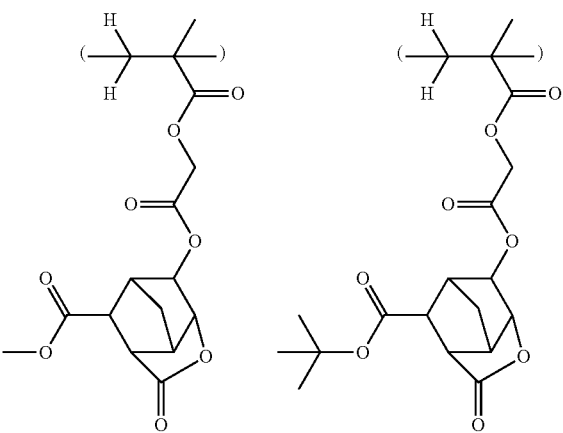
144
-continued
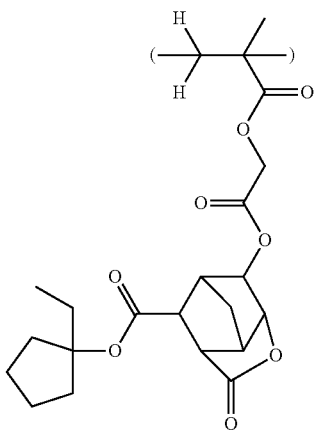
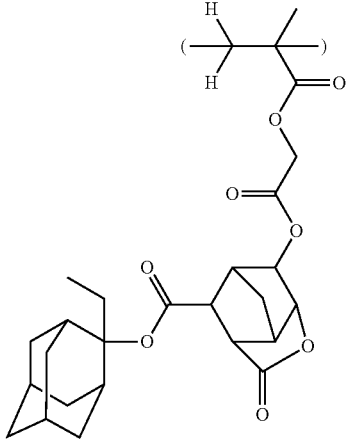
and
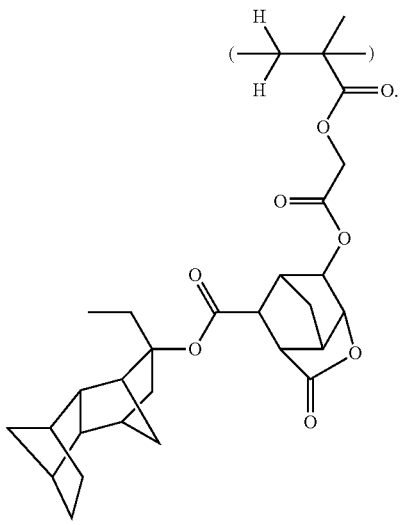 [SMILES: CCC(C)(C)C(=O)OCC(=O)OC1C2CC3C1OC(=O)C3C2C(=O)OC1(CC)CC2CC1C1C3CCC(C3)C21]
11. The polymer of claim 6, wherein the unit of general formula (12) is selected form the group consisting of:

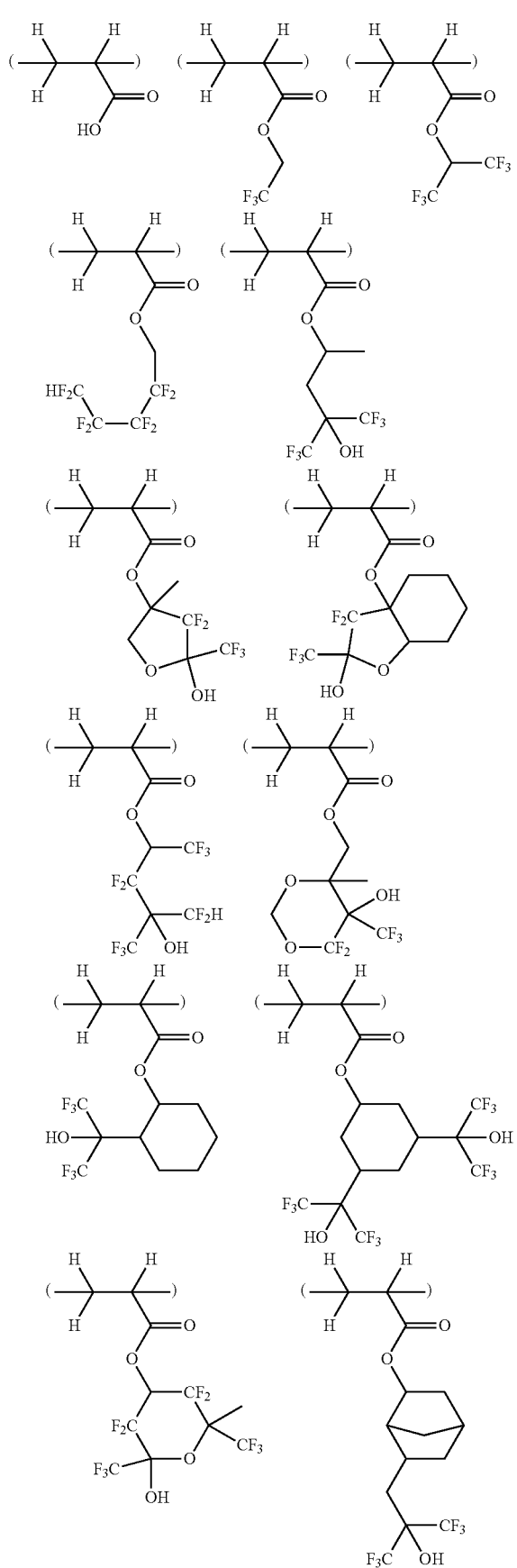
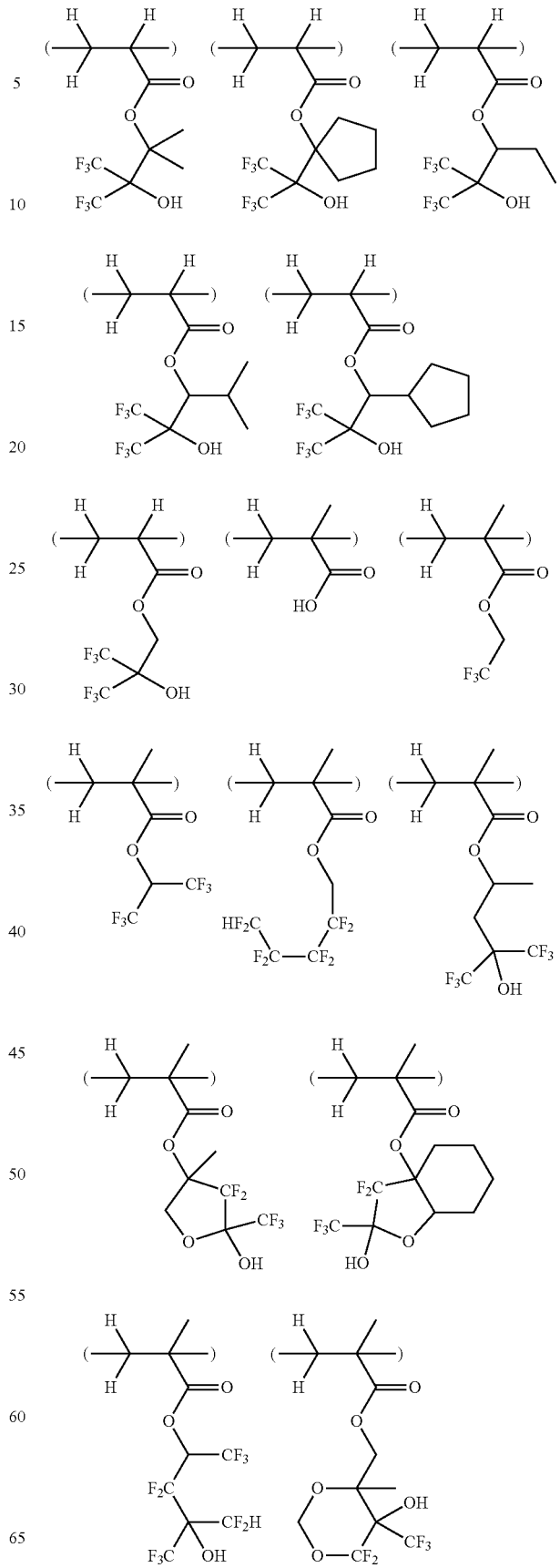

-continued

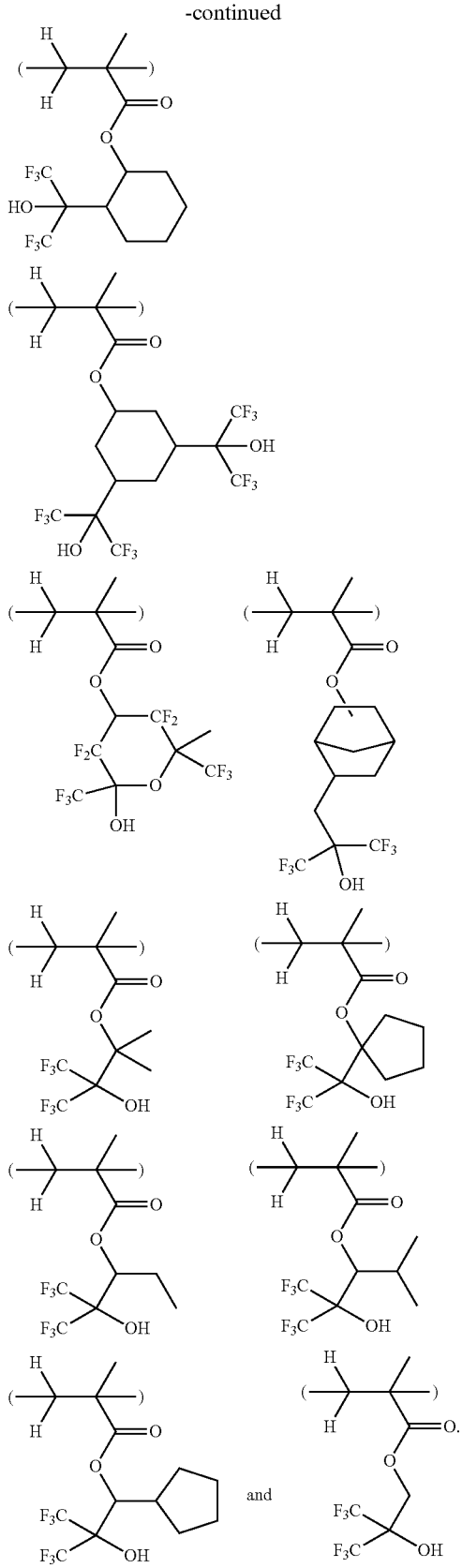

12. A resist composition comprising the polymer of claim 6 as a base resin.

13. A resist composition comprising the polymer of claim 5 as a base resin.

14. A process for forming a pattern, comprising the steps of applying the resist composition of claim 13 onto a substrate to form a resist coating; heat treating the resist coating and exposing to high-energy radiation or electron beam through a photomask; and heat treating the exposed coating and developing with a developer.

15. A process for forming a pattern, comprising the steps of applying the resist composition of claim 13 onto a substrate to form a resist coating; heat treating the resist coating and exposing to high-energy radiation or electron beam through a photomask; and heat treating the exposed coating and developing with a developer, said exposing step being performed by immersion lithography including holding a high refractive index liquid having a refractive index of at least 1.0 between the resist coating and a projection lens.

16. A process for forming a pattern, comprising the steps of applying the resist composition of claim 13 onto a substrate to form a resist coating, heat treating the resist coating, forming a protective film on the resist coating, exposing the resist coating to high-energy radiation or electron beam through a photomask, heat treating the exposed coating, and developing it with a developer, said exposing step being performed by immersion lithography including holding a high refractive index liquid having a refractive index of at least 1.0 between the protective film and a projection lens.

17. The polymer of claim 5, wherein the recurring units having the general formula (8) are derived from an acetal compound selected from the group consisting of:

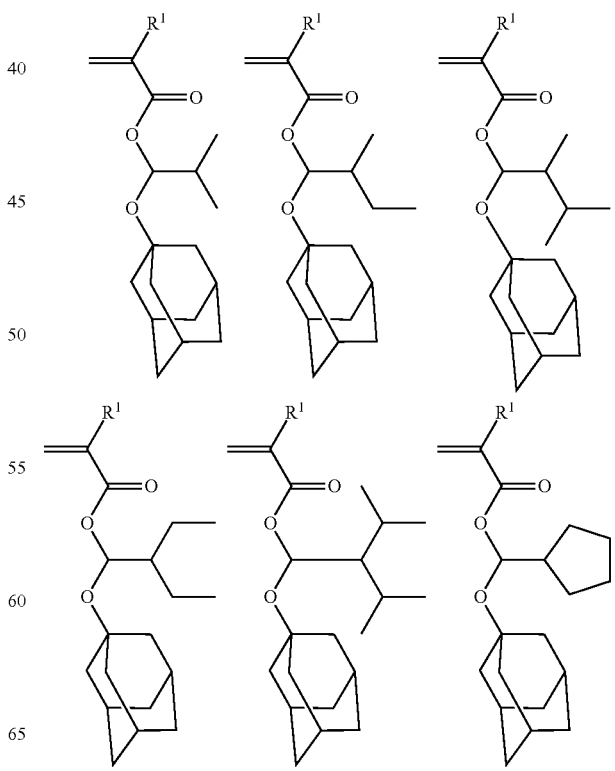

149
-continued
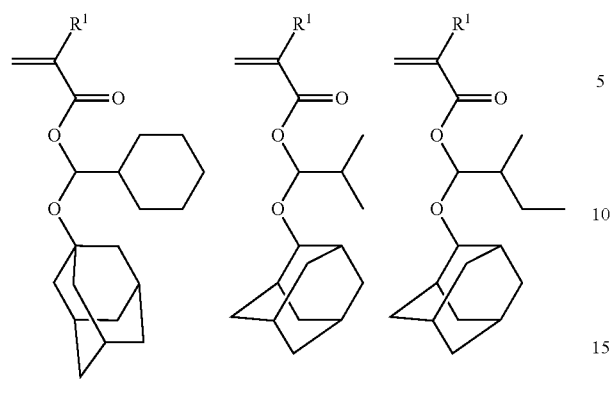
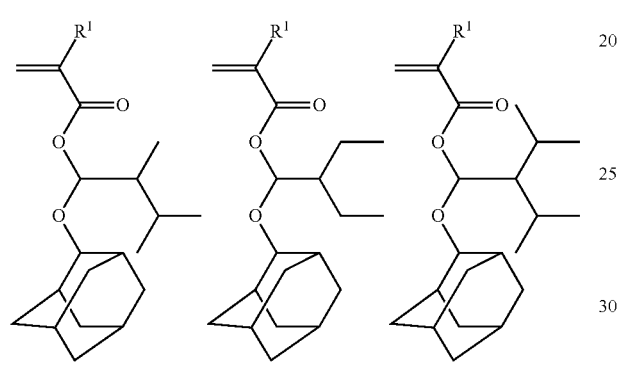
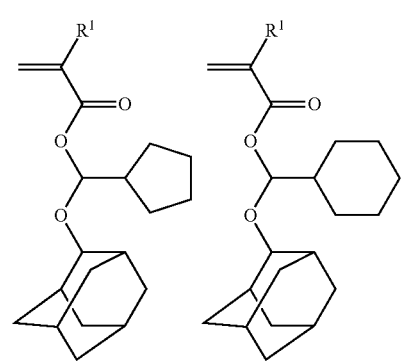
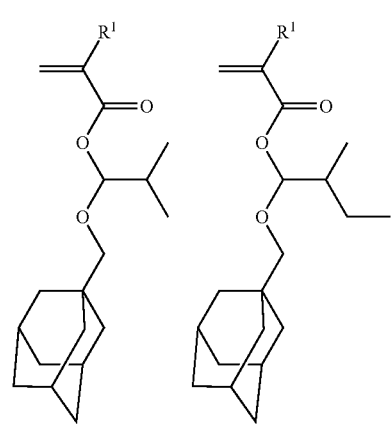
150
-continued
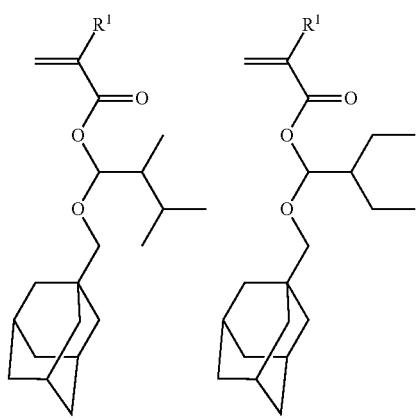
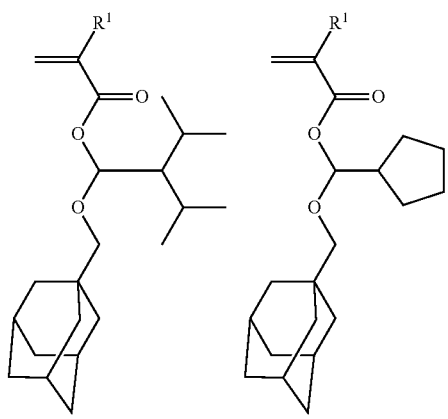
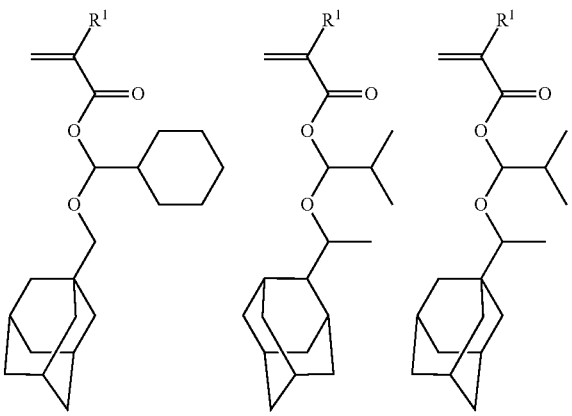
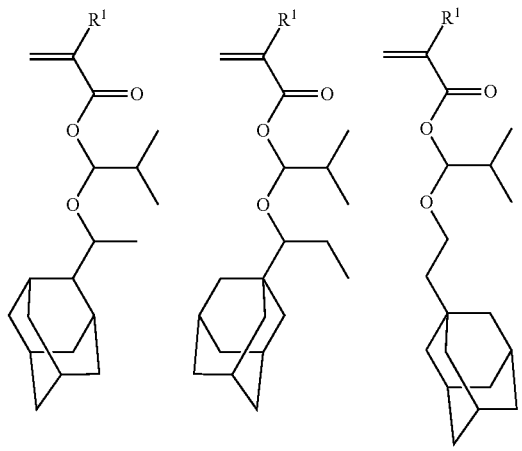

-continued
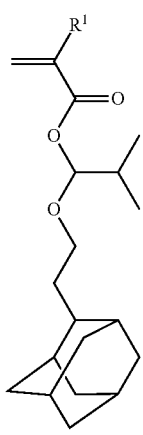 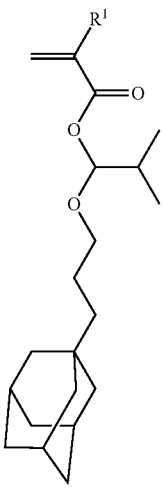  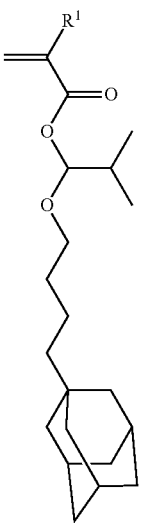 and 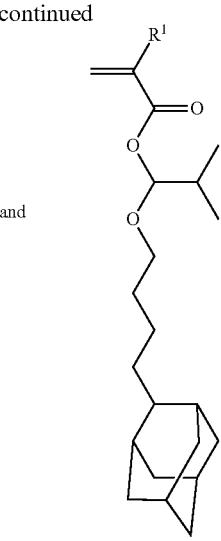
wherein R¹ is hydrogen, methyl or trifluoromethyl.
* * * * *